US008404845B2

(12) United States Patent
Anilkumar et al.

(10) Patent No.: US 8,404,845 B2
(45) Date of Patent: Mar. 26, 2013

(54) 2,3-SUBSTITUTED AZAINDOLE DERIVATIVES FOR TREATING VIRAL INFECTIONS

(75) Inventors: Gopinadhan N. Anilkumar, Edison, NJ (US); Stuart B. Rosenblum, West Orange, NJ (US); Srikanth Venkatraman, Edison, NJ (US); F. George Njoroge, Warren, NJ (US); Joseph A. Kozlowski, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 262 days.

(21) Appl. No.: 12/675,270

(22) PCT Filed: Aug. 27, 2008

(86) PCT No.: PCT/US2008/010149
§ 371 (c)(1),
(2), (4) Date: May 7, 2010

(87) PCT Pub. No.: WO2009/032125
PCT Pub. Date: Mar. 12, 2009

(65) Prior Publication Data
US 2010/0239527 A1 Sep. 23, 2010

Related U.S. Application Data

(60) Provisional application No. 60/968,707, filed on Aug. 29, 2007.

(51) Int. Cl.
C07D 471/04 (2006.01)
A61K 31/437 (2006.01)
(52) U.S. Cl. ........................................ 546/113; 514/300
(58) Field of Classification Search .................. 546/113; 514/300
See application file for complete search history.

(56) References Cited

U.S. PATENT DOCUMENTS

| | | | |
|---|---|---|---|
| 3,632,805 A | 1/1972 | Yamamoto et al. | |
| 4,634,697 A | 1/1987 | Hamashima | |
| 4,812,561 A | 3/1989 | Hamashima et al. | |
| 4,933,443 A | 6/1990 | Hamashima et al. | |
| 5,017,380 A | 5/1991 | Hamashima et al. | |
| 6,800,434 B2 | 10/2004 | Saksena et al. | |
| 6,838,475 B2 | 1/2005 | Arasappan et al. | |
| 6,846,802 B2 | 1/2005 | Chen et al. | |
| 6,911,428 B2 | 6/2005 | Zhu et al. | |
| 6,914,122 B2 | 7/2005 | Venkatraman et al. | |
| 7,012,066 B2 | 3/2006 | Saksena et al. | |
| 2002/0160962 A1 | 10/2002 | Saksena et al. | |
| 2004/0077704 A1 | 4/2004 | Beight et al. | |
| 2005/0075331 A1 | 4/2005 | Pratt et al. | |
| 2005/0101770 A1 | 5/2005 | Presta | |
| 2005/0176648 A1 | 8/2005 | Saksena et al. | |
| 2005/0249702 A1 | 11/2005 | Njoroge et al. | |
| 2007/0274951 A1 | 11/2007 | Tong et al. | |
| 2010/0098661 A1 | 4/2010 | Chen et al. | |
| 2010/0196319 A1 | 8/2010 | Anilkumar et al. | |
| 2010/0239527 A1 | 9/2010 | Anilkumar et al. | |
| 2010/0260711 A1 | 10/2010 | Chen et al. | |
| 2010/0322901 A1 | 12/2010 | Bennett et al. | |
| 2011/0033417 A1 | 2/2011 | Anilkumar et al. | |
| 2011/0104109 A1 | 5/2011 | Bennett et al. | |
| 2011/0104110 A1 | 5/2011 | Anikumar et al. | |
| 2011/0165118 A1 | 7/2011 | Chan et al. | |

FOREIGN PATENT DOCUMENTS

| | | |
|---|---|---|
| AU | 2002313410 B2 | 7/2002 |
| DE | 648639 C | 8/1937 |
| EP | 0449196 A2 | 10/1991 |
| FR | 2768146 A1 | 3/1999 |
| JP | 4-149429 | 5/2004 |
| WO | 96/37619 A1 | 11/1996 |
| WO | 98/14181 A1 | 4/1998 |
| WO | 98/17679 A1 | 4/1998 |
| WO | 98/22496 A2 | 5/1998 |
| WO | 99/07734 A2 | 2/1999 |
| WO | 02/30895 A1 | 4/2002 |
| WO | 02/068412 A1 | 9/2002 |
| WO | 2004/035571 A1 | 4/2004 |
| WO | 2004/106328 A1 | 12/2004 |
| WO | 2005/034941 A1 | 4/2005 |
| WO | 2005/084315 A2 | 9/2005 |
| WO | 2005/087731 A1 | 9/2005 |
| WO | 2005/111018 A1 | 11/2005 |
| WO | 2006/020082 A1 | 2/2006 |
| WO | 2006/032541 A1 | 3/2006 |
| WO | 2006/034337 A2 | 3/2006 |
| WO | 2006/046030 A2 | 5/2006 |
| WO | 2006/076529 A1 | 7/2006 |
| WO | 2007/029029 A2 | 3/2007 |
| WO | 2007/038209 A2 | 4/2007 |
| WO | 2007/084413 A2 | 7/2007 |
| WO | 2007/084435 A2 | 7/2007 |
| WO | 2008/082484 A1 | 7/2008 |

OTHER PUBLICATIONS

West, Anthony R., Solid State Chemistry and its Applications, Wiley, New York, 1988, pp. 358 & 365.*
Banker (Modern Pharmaceutics) Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Tan et al., "Hepatitis C Therapeutics: Current Status and Emerging Strategies", Nature Reviews, 2002, vol. 1, pp. 867-881.
Beaulieu et al., "Inhibitors of the HCV NS5B polymerase: New hope for the treatment of hepatitis C infections", Current Opinion in Investigational Drugs, 2004, vol. 5, pp. 838-850, No. 8.

(Continued)

Primary Examiner — David K O'Dell
(74) Attorney, Agent, or Firm — Melissa B. Wenk; Sheldon O. Heber

(57) ABSTRACT

The present invention relates to 2,3-Substituted Azaindole Derivatives, compositions comprising at least one 2,3-Substituted Azaindole Derivatives, and methods of using the 2,3-Substituted Azaindole Derivatives for treating or preventing a viral infection or a virus-related disorder in a patient.

15 Claims, No Drawings

OTHER PUBLICATIONS

Behrens et al., "Identification and properties of the RNA-dependent RNA polymerase of hepatitis C virus", The EMBO Journal, 1996, vol. 15, pp. 12-22, No. 1.

Bioworld Today, 9 (217):4 Nov. 10, 1998, pp. 1-5.

Birnbock et al., "Sulfate Derivatives of 2-Phenylindols as Novel Steroid Sulfatase Inhibitors", Biochemical Pharmacology, 1990, vol. 39, pp. 1709-1713, No. 11.

Bunker et al., "1,3-Diaryl-2-Carboxyindoles as Potent Non-Peptide Endothelin Antagonists", Bioorganic & Medicinal Chemistry Letters, 1996, vol. 6, pp. 1061-1066, No. 9.

Chemical and Pharmaceutical Bulletin, vol. 19, 1971, p. 263-270.

Denmark et al., "Palladium-Catalyzed Cross-Coupling Reactions of Silanolates: A Paradigm Shift in Silicon-Based Cross-Coupling Reactions", Chem. Eur. J., 2006, vol. 12, pp. 4954-4963.

Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997, vol. 71, pp. 7461-7469, No. 10.

Elzouki et al., "Serine protease inhibitors in patients with chronic viral hepatitis", Journal of Hepatology, 1997, vol. 27, pp. 42-48.

Ferrari et al., "Characterization of Soluble Hepatitis C Virus RNA-Dependent RNA Polymerase Expressed in *Escherichia coli*", Journal of Virology, 1999, vol. 73, pp. 1649-1654, No. 2.

Fonseca et al., "Synthesis and antiviral evaluation of benzimidazoles, quinoxalines and indoles from dehydroabietic acid", Bioorganic & Medicinal Chemistry, 2004, vol. 12, pp. 103-112.

Forbes et al., "Synthesis, Biological Activity, and Molecular Modeling Studies of Selective 5-HT2C/2B Receptor Antagonists", J. Med. Chem., 1996, vol. 39, pp. 4966-4977, No. 25.

Goldsmith et al., "Studies in the Benzindole Series", J. Org. Chem, 1952, vol. 18, pp. 507-514.

Gopalsamy et al., "Design and synthesis of 2,3,4,9-tetrahydro-1H-carbazole and 1,2,3,4-tetrahydro-cyclopenta[b] indole derivatives as non-nucleoside inhibitors of hepatitis C virus NS5B RNA-dependent RNA polymerase", Bioorganic & Medicinal Chemistry Letters, 2006, vol. 16, pp. 2532-2534.

Humphrey et al., "Practical Methodologies for the Synthesis of Indoles", Chem. Rev., 2006, vol. 106, pp. 2875-2911.

International Search Report for International Application No. PCT/US2007/025754, mailed May 13, 2008, (4 pages).

Written Opinion for PCT/US2007/025754, filed Dec. 17, 2007, (7 pages).

International Search Report for International Application No. PCT/US2007/025765, mailed May 13, 2008, (6 pages).

Written Opinion for PCT/US2007/025765, filed Dec. 17, 2007, (8 pages).

International Search Report for International Application No. PCT/US2007/025757, mailed Mar. 6, 2009, (8 pages).

Written Opinion for PCT/US2007/025757, filed Dec. 17, 2007 (12 pages).

International Search Report for International Application No. PCT/US2008/010130, mailed Jan. 22, 2009, (5 pages).

Written Opinion for PCT/US2008/010130, filed Aug. 27, 2008 (9 pages).

International Search Report for International Application No. PCT/US2008/010149, mailed Feb. 2, 2009, (5 pages).

Written Opinion for PCT/US2008/010149, filed Aug. 27, 2008 (6 pages).

International Search Report for International Application No. PCT/US2008/083351, mailed Feb. 27, 2009, (3 pages).

Written Opinion for PCT/US2008/083351, filed Nov. 13, 2008 (5 pages).

International Search Report for International Application No. PCT/US2008/010147, mailed May 4, 2009, (3 pages).

Written Opinion for PCT/US2008/010147, filed Aug. 27, 2008 (6 pages).

International Search Report for International Application No. PCT/US2008/083358, mailed Mar. 6, 2009, (2 pages).

Written Opinion for PCT/US2008/083358, filed Nov. 13, 2008 (5 pages).

International Search Report for International Application No. PCT/US2008/010148, mailed Dec. 9, 2008, (3 pages).

Written Opinion for PCT/US2008/010148, filed Aug. 27, 2008 (7 pages).

International Search Report for International Application No. PCT/US2009/046822, mailed Oct. 7, 2009, (5 pages).

Written Opinion for PCT/US2009/046822, filed Jun. 10, 2009 (8 pages).

Ingallinella et al., "Potent Peptide Inhibitors of Human Hepatitis C Virus NS3 Protease are Obtained by Optimizing the Cleavage Products", Biochemistry, 1998, vol. 37, pp. 8906-8914.

Journal of Heterocyclic Chemistry, vol. 12, 1975, pp. 351-358.

Journal of Medicinal Chemistry, vol. 23, No. 7, 1980, pp. 764-773.

Journal of Organic Chemistry, vol. 27, 1962, pp. 3782-3786.

Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1997, vol. 36, pp. 9340-9348.

Lindsay et al., "SmI2-Promoted Radical Addition Reactions with N-(2-Indolylacyl)oxazolidinones: Synthesis of Bisindole Compounds", Journal of Organic Chemistry, 2007, vol. 72, pp. 4181-4188, No. 11.

Llinas-Brunet et al., "Peptide-Based Inhibitors of the Hepatitis C Virus Serine Protease", Bioorganic & Medicinal Chemistry Letters, 1998, vol. 8, pp. 1713-1718.

Malcolm et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, vol. 50, pp. 1013-1020, No. 3.

Martin, et al., "Affinity selection of a camelized VH domain antibody inhibitor of hepatitis C virus NS3 protease", Protein Engineering, 1997, vol. 10, pp. 607-614, No. 5.

Martin et al., "Design of Selective Eglin Inhibitors of HCV NS3 Proteinase", Biochemistry, 1998, vol. 37, pp. 11459-11468.

Muratake et al., "Synthesis of Duocarmycin SA by Way of Methyl 4-(Methoxycarbonyl)oxy-3H-pyrrolo[3,2-f] quinoline-2-carboxylate as a Tricyclic Heteroaromatic Intermediate", Chem. Pharm. Bulletin, 1998, vol. 46, pp. 400-412, No. 3.

Ni et al., "Progress and development of small molecule HCV antivirals", Current Opinion in Drug Discovery & Development, 2004, vol. 7, pp. 446-459, No. 4.

Rawal et al., "Photocyclization of Pyrrole Analogues of Stilbene: an Expedient Approach to Anti-tumour Agent CC-1065", Journal Chem. Soc., Chem. Commun., 1984, pp. 1526-1527.

Sechi et al., "Design and Synthesis of Novel Indole β-Diketo Acid Derivatives as HIV-1 Integrase Inhibitors", J. Med. Chem., 2004, vol. 47, pp. 5298-5310, No. 21.

Silvestri et al., "Synthesis and biological evaluation of 5H-indolo [3,2-b][1,5]benzothiazepine derivatives, designed as conformationally constrained analogues of the human immunodeficiency virus type 1 reverse transcriptase inhibitor L-737,126", Antiviral Chemistry & Chemotherapy, 1998, vol. 9, pp. 139-148.

\* cited by examiner

2,3-SUBSTITUTED AZAINDOLE DERIVATIVES FOR TREATING VIRAL INFECTIONS

FIELD OF THE INVENTION

The present invention relates to 2,3-Substituted Azaindole Derivatives, compositions comprising at least one 2,3-Substituted Azaindole Derivative, and methods of using the 2,3-Substituted Azaindole Derivatives for treating or preventing a viral infection or a virus-related disorder in a patient.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a five-year survival rate of less than 1%.

HCV is an enveloped RNA virus containing a single-stranded positive-sense RNA genome approximately 9.5 kb in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$—C-E1-E2-p7-NS2-NS3-NS4A-NS4B-NS5A-NS5B—COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase has provided important structural insights that should assist in the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)(3-L-2',3'-dideoxy-3'-thiacytidine 5'-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

In one aspect, the present invention provides compounds of formula (I):

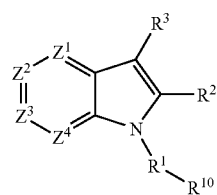

and pharmaceutically acceptable salts, solvates, esters and prodrugs thereof,
wherein:
$Z^1$ is —N—; —N(O)— or —C($R^4$)—;
$Z^2$ is —N—, —N(O)— or —C($R^5$)—;
$Z^3$ is —N—, —N(O)— or —C($R^6$)—;
$Z^4$ is —N—, —N(O)— or —C($R^7$)—, such that at least one of $Z^1$, $Z^2$, $Z^3$ and $Z^4$ is —N— or —N(O)—;
$R^1$ is a bond, —[C($R^{12}$)$_2$]$_r$—, —[C($R^{12}$)$_2$]$_r$—O—[C($R^{12}$)$_2$]$_q$, —[C($R^{12}$)$_2$]$_r$—N($R^9$)—[C($R^{12}$)$_2$]$_q$—, —[C($R^{12}$)$_2$]$_q$—CH=CH—[C($R^{12}$)$_2$]$_q$, —[C($R^{12}$)$_2$]$_q$—C≡C—[C($R^{12}$)$_2$]$_q$—, or —[C($R^{12}$)$_2$]$_q$—SO$_2$—[C($R^{12}$)$_2$]$_q$—;

$R^2$ is —[C($R^{12}$)$_2$]$_q$—C(O)N($R^9$)SOR$^{11}$, —[C($R^{12}$)$_2$]$_q$—C(O)N($R^9$)SO$_2$R$^{11}$, —[C($R^{12}$)$_2$]$_q$—C(O)N($R^9$)SO$_2$N($R^{11}$)$_2$,

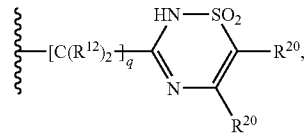

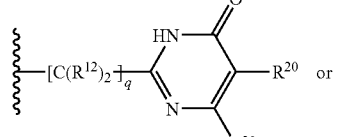

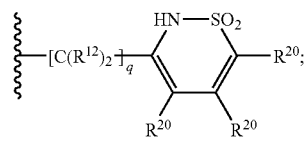

$R^3$ is:

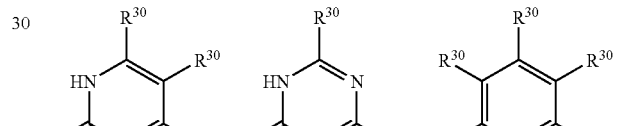

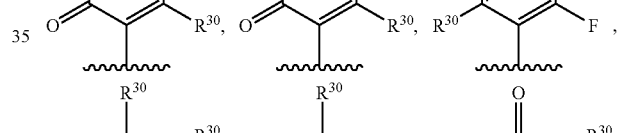

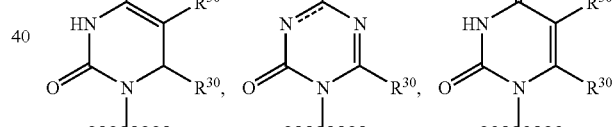

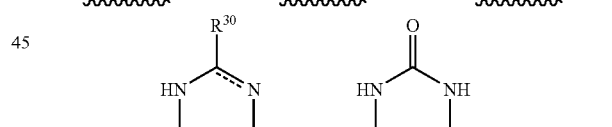

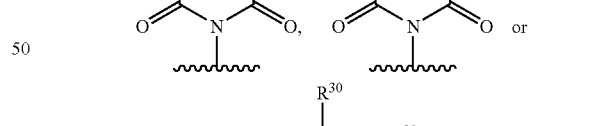

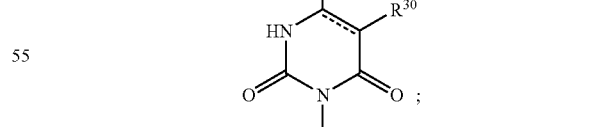

$R^4$, $R^5$, $R^6$ and $R^7$ are each, independently, H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —OR$^9$, —CN, —[C($R^{12}$)$_2$]$_q$—C(O)R$^8$, —[C($R^{12}$)$_2$]$_q$—C(O)OR$^9$, —[C($R^{12}$)$_2$]$_q$—C(O)N($R^9$)$_2$, —[C($R^{12}$)$_2$]$_q$—OR$^9$, —[C(R$^{12}$)$_2$]$_q$N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$;

each occurrence of R$^8$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

each occurrence of R$^9$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

R$^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, such that when R$^1$ is a bond, R$^{10}$ is not H;

each occurrence of R$^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, [C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$ alkyl, —[C(R$^{12}$)$_2$]$_q$—NHSO$_2$ cycloalkyl, —[C(R$^{12}$)$_2$]$_q$—NHSO$_2$ aryl, —[C(R$^{12}$)$_2$]$_q$—SO$_2$N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$ alkyl, —SO$_2$ alkyl or —SO$_2$NH-alkyl, or two R$^{12}$ groups, together with the carbon atoms to which they are attached, join to form a cycloalkyl, heterocycloalkyl or C=O group;

each occurrence of R$^{20}$ is independently alkyl, aryl, cycloalkyl, heterocycloalkyl or heteroaryl, or both R$^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, hydroxy, —OR$^9$, —CN, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-haloalkyl, —[C(R$^{12}$)$_2$]$_q$-hydroxyalkyl, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

each occurrence of R$^{30}$ is independently H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$, or two adjacent R$^{30}$ groups, together with the carbon atoms to which they are attached, join to form a –3- to 7-membered ring selected from aryl, cycloalkyl, heteroaryl and heterocycloalkyl;

each occurrence of p is independently 0, 1 or 2;

each occurrence of q is independently an integer ranging from 0 to 4; and each occurrence of r is independently an integer ranging from 1 to 4.

In another aspect, the invention provides compounds of formula (II):

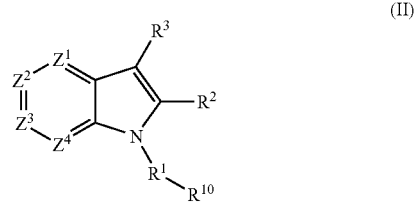

and pharmaceutically acceptable salts, solvates, esters and prodrugs thereof,
wherein:

Z$^1$ is —N—, —N(O)— or —C(R$^4$)—;

Z$^2$ is —N—, —N(O)— or —C(R$^5$)—;

Z$^3$ is —N—, —N(O)— or —C(R$^6$)—;

Z$^4$ is —N—, —N(O)— or —C(R$^7$)—, such that at least one of Z$^1$, Z$^2$, Z$^3$ and Z$^4$ is —N— or —N(O)—;

R$^1$ is a bond, —[C(R$^{12}$)$_2$]$_r$—, —[C(R$^{12}$)$_2$]$_r$—O—[C(R$^{12}$)$_2$]$_q$, —[C(R$^{12}$)$_2$]$_r$—N(R$^9$)—[C(R$^{12}$)$_2$]$_q$—, —[C(R$^{12}$)$_2$]$_q$—CH=CH—[C(R$^{12}$)$_2$]$_q$—, —[C(R$^{12}$)$_2$]$_q$—C=C—[C(R$^{12}$)$_2$]$_q$—, or —[C(R$^{12}$)$_2$]$_q$—SO$_2$—[C(R$^{12}$)$_2$]$_q$;

R$^2$ is —C(O)R$^9$, —C(O)OR$^9$, —C(O)OCH$_2$OR$^9$, —C(O)N(R$^9$)$_2$, —[C(R$^{12}$)$_2$]$_q$—C(O)OR$^9$, —[C(R$^{12}$)$_2$]$_q$—C(O)N(R$^9$)$_2$, -alkyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heteroaryl or —[C(R$^{12}$)$_2$]$_q$-heterocycloalkenyl, wherein an aryl, cycloalkyl, cycloalkenyl, heterocycloalkyl, heterocycloalkenyl or heteroaryl group can be optionally substituted with up to 4 substituents, which are the same or different, and are selected from alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)

$OR^9)_2$, $-[C(R^{12})_2]_q-C(O)N(R^9)_2$, $-[C(R^{12})_2]^q-OR^9$, $-[C(R^{12})_2]_q-N(R^9)_2$, $-[C(R^{12})_2]^q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ and $-SO_2N(R^9)C(O)N(R^9)_2$;

$R^3$ is:

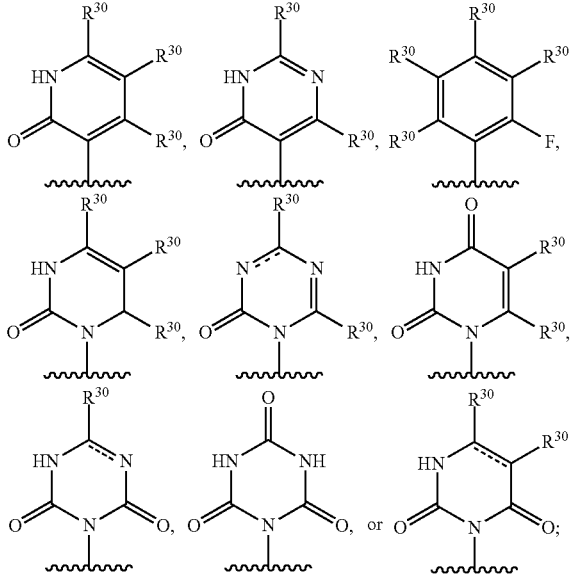

$R^4$, $R^5$, $R^6$ and $R^7$ are each, independently, H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]^q$-hydroxyalkyl, halo, hydroxy, $-OR^9$, $-CN$, $-[C(R^{12})_2]_q-C(O)R^9$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_qNR^8C(O)N(R^9)_2$, $-[C(R^{12})_2]_q-NHSO_2R^{11}$, $-[C(R^{12})_2]_q-S(O)R^9$, $-[C(R^{12})_2]_q-SO_2N(R^9)_2$ or $-SO_2N(R^9)C(O)N(R^9)_2$;

each occurrence of $R^8$ is independently H, alkyl, alkenyl, alkynyl, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, haloalkyl or hydroxyalkyl;

each occurrence of $R^9$ is independently H, alkyl, alkenyl, alkynyl, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, haloalkyl or hydroxyalkyl;

$R^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ and $-SO_2N(R^9)C(O)N(R^9)_2$, such that when $R^1$ is a bond, $R^{10}$ is not H;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_qN(R^9)_2$, $-[C(R^{12})_2]_q-NHC(O)R^8$, $-[C(R^{12})_2]_qNR^8C(O)N(R^9)_2$, $-[C(R^{12})_2]_q-NHSO_2$alkyl, $-[C(R^{12})_2]_q-NHSO_2$ cycloalkyl, $-[C(R^{12})_2]_q-NHSO_2$aryl, $-[C(R^{12})_2]_q-SO_2N(R^9)_2$ and $-SO_2N(R^9)C(O)N(R^9)_2$;

each occurrence of $R^{12}$ is independently H, halo, $-N(R^9)_2$, $-OR^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, —CN, —C(O) alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O) alkyl, —NHSO$_2$ alkyl, —SO$_2$ alkyl or —SO$_2$NH-alkyl, or two $R^{12}$ groups, together with the carbon atoms to which they are attached, join to form a cycloalkyl, heterocycloalkyl or C=O group;

each occurrence of $R^{20}$ is independently alkyl, aryl, cycloalkyl, heterocycloalkyl or heteroaryl, or both $R^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, hydroxy, $-OR^9$, $-CN$, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-haloalkyl, $-[C(R^{12})_2]_q$-hydroxyalkyl, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-S(O)_pR^{11}$, $-[C(R^{12})_2]_q-SO_2N(R^9)_2$ and $-SO_2N(R^9)C(O)N(R^9)_2$;

each occurrence of $R^{30}$ is independently H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ or $-SO_2N(R^9)C(O)N(R^9)_2$, or two adjacent $R^{30}$ groups, together with the carbon atoms to which they are attached, join to form a –3- to 7-membered ring selected from aryl, cycloalkyl, heteroaryl and heterocycloalkyl;

each occurrence of p is independently 0, 1 or 2;

each occurrence of q is independently an integer ranging from 0 to 4; and each occurrence of r is independently an integer ranging from 1 to 4.

The compounds of formulas (I) and (I) (herein referred to collectively as the "2,3-Substituted Azaindole Derivatives") and pharmaceutically acceptable salts, solvates, esters and prodrugs thereof can be useful for treating or preventing a viral infection or a virus-related disorder in a patient.

Also provided by the invention are methods for treating or preventing a viral infection or a virus-related disorder in a patient, comprising administering to the patient an effective amount of at least one 2,3-Substituted Azaindole Derivative.

The present invention further provides pharmaceutical compositions comprising an effective amount of at least one 2,3-Substituted Azaindole Derivative or a pharmaceutically acceptable salt, solvate thereof, and a pharmaceutically acceptable carrier. The compositions can be useful for treating or preventing a viral infection or a virus-related disorder in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides 2,3-Substituted Azaindole Derivatives, pharmaceutical compositions comprising at least one 2,3-Substituted Azaindole Derivative, and methods of using the 2,3-Substituted Azaindole Derivatives for treating or preventing a viral infection or in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "alkyl" as used herein, refers to an aliphatic hydrocarbon group, wherein one of the aliphatic hydrocarbon group's hydrogen atoms is replaced with a single bond. An alkyl group can be straight or branched and can contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or optionally substituted by one or more substituents which may be the same or different, each substituent being independently selected from the group consisting of halo, alkenyl, alkynyl, —O-aryl, aryl, heteroaryl, cycloalkyl, cycloalkenyl, cyano, hydroxy, —O-alkyl, —O-haloalkyl, -alkylene-O-alkyl, alkylthio, —$NH_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkyl group is unsubstituted. In another embodiment, an alkyl group is a straight chain alkyl group. In another embodiment, an alkyl group is a branched alkyl group.

The term "alkenyl" as used herein, refers to an aliphatic hydrocarbon group having at least one carbon-carbon double bond, wherein one of the aliphatic hydrocarbon group's hydrogen atoms is replaced with a single bond. An alkenyl group can be straight or branched and can contain from about 2 to about 15 carbon atoms. In one embodiment, an alkenyl group contains from about 2 to about 10 carbon atoms. In another embodiment, an alkenyl group contains from about 2 to about 6 carbon atoms. Non-limiting examples of illustrative alkenyl groups include ethenyl, propenyl, n-butenyl, 3-methylbut-2-enyl, n-pentenyl, octenyl and decenyl. An alkenyl group may be unsubstituted or optionally substituted by one or more substituents which may be the same or different, each substituent being independently selected from the group consisting of halo, alkyl, alkynyl, —O-aryl, aryl, cycloalkyl, cycloalkenyl, cyano, hydroxy, —O-alkyl, —O-haloalkyl, -alkylene-O-alkyl, alkylthio, —$NH_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)— cycloalkyl, —C(O)alkyl, —C(O)NH$_2$, —C(O)NH-alkyl, —C(O)OH and —C(O)O-alkyl. In one embodiment, an alkenyl group is unsubstituted. In another embodiment, an alkenyl group is a straight chain alkenyl group. In another embodiment, an alkyl group is a branched alkenyl group.

The term "alkynyl" as used herein, refers to an aliphatic hydrocarbon group having at least one carbon-carbon triple bond, wherein one of the aliphatic hydrocarbon group's hydrogen atoms is replaced with a single bond. An alkynyl group can be straight or branched and can contain from about 2 to about 15 carbon atoms. In one embodiment, an alkynyl group contains from about 2 to about 10 carbon atoms. In another embodiment, an alkynyl group contains from about 2 to about 6 carbon atoms. Non-limiting examples of illustrative alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of halo, alkyl, alkenyl, —O-aryl, aryl, cycloalkyl, cycloalkenyl, cyano, hydroxy, —O-alkyl, -alkylene-O-alkyl, —O-haloalkyl, -alkylthio, —$NH_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)- cycloalkyl, —C(O)alkyl, —C(O)NH$_2$, —C(O)NH-alkyl, —C(O)OH and —C(O)O-alkyl. In one embodiment, an alkynyl group is unsubstituted. In another embodiment, an alkynyl group is a straight chain alkynyl group. In another embodiment, an alkynyl group is a branched alkynyl group.

The term "alkylene" as used herein, refers to an alkyl group, as defined above, wherein one of the alkyl group's hydrogen atoms is replaced with a bond. Illustrative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH$_2$CH(CH$_3$)CH$_2$— and —CH$_2$CH$_2$CH(CH$_3$)—. In one embodiment, an alkylene group is a straight chain alkylene group. In another embodiment, an alkylene group is a branched alkylene group.

"Aryl" means an aromatic monocyclic or multicyclic ring system having from about 6 to about 14 ring carbon atoms. In one embodiment, an aryl group has from about 6 to about 10 ring carbon atoms. An aryl group can be optionally substituted with one or more "ring system substituents" which may be the same or different, and are as defined herein below. Non-limiting examples of illustrative aryl groups include phenyl and naphthyl. In one embodiment, an aryl group is unsubstituted. In another embodiment, an aryl group is a phenyl group.

The term "cycloalkyl" as used herein, refers to a non-aromatic mono- or multicyclic ring system having from about 3 to about 10 ring carbon atoms. In one embodiment, a cycloalkyl has from about 5 to about 10 ring carbon atoms. In another embodiment, a cycloalkyl has from about 5 to about 7 ring carbon atoms. Non-limiting examples of illustrative monocyclic cycloalkyls include cyclopropyl, cyclopentyl, cyclohexyl, cycloheptyl and the like. Non-limiting examples of illustrative multicyclic cycloalkyls include 1-decalinyl, norbornyl, adamantyl and the like. A cycloalkyl group can be optionally substituted with one or more "ring system substituents" which may be the same or different, and are as defined herein below. In one embodiment, a cycloalkyl group is unsubstituted.

The term "cycloalkenyl" as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring carbon atoms. Non-limiting examples of illustrative monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted.

The term "halo" as used herein, means —F, —Cl, —Br or —I. In one embodiment, halo refers to —Cl or —F.

The term "haloalkyl" as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of illustrative haloalkyl groups include —CH$_2$F, —CHF$_2$, —CF$_3$, —CH$_2$Cl and —CCl$_3$.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of illustrative hydroxyalkyl groups include hydroxymethyl, 2-hydroxyethyl, 3-hydroxypropyl, 4-hydroxybutyl and —CH(OH)CH$_2$CH$_3$.

The term "heteroaryl" as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group can be optionally substituted by one or more "ring system substituents" which may be the same or different, and are as defined herein below. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring. Non-limiting examples of illustrative heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is a 6-membered heteroaryl group. In another embodiment, a heteroaryl group is a 5-membered heteroaryl group.

The term "heterocycloalkyl" as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(Boc), —N(CBz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of illustrative monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

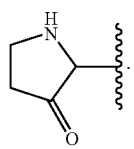 [SMILES: *C1NCCC1=O]

In one embodiment, a heterocycloalkyl group is a 6-membered heterocycloalkyl group. In another embodiment, a heterocycloalkyl group is a 5-membered heterocycloalkyl group.

The term "heterocycloalkenyl" as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of illustrative heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. A ring carbon atom of a heterocyclenyl group may be functionalized as a carbonyl group. An illustrative example of such a heterocyclenyl group is:

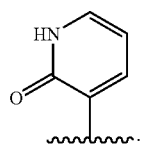

In one embodiment, a heterocycloalkenyl group is a 6-membered heterocycloalkenyl group. In another embodiment, a heterocycloalkenyl group is a 5-membered heterocycloalkenyl group.

The term "ring system substituent" as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, —O-alkyl, -alkylene-O-alkyl, —O-aryl, aralkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —OC(O)-alkyl, —OC(O)-aryl, —OC(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkylene-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

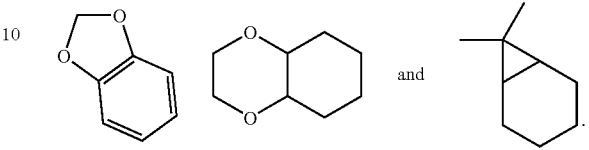

The term "substituted," as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" as used herein, means optional substitution with the specified groups, radicals or moieties.

The terms "purified", "in purified form" or "in isolated and purified form" as used herein, for a compound refers to the physical state of said compound after being isolated from a synthetic process (e.g. from a reaction mixture), or natural source or combination thereof.

Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R$^{11}$, etc.) occurs more than one time in any constituent or in Formula (I) or (II), its definition on each occurrence is independent of its definition at every other occurrence, unless otherwise noted.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as used herein, refers to a compound (e.g, a drug precursor) that is transformed in vivo to yield a 2,3-Substituted Azaindole Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a 2,3-Substituted Azaindole Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as (3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$) alkyl, and the like.

Similarly, if a 2,3-Substituted Azaindole Derivative contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$ alkyl$)_2$ or glycosyl (the radical resulting from the removal of a hydroxyl group of the hemiacetal form of a carbohydrate), and the like.

If a 2,3-Substituted Azaindole Derivative incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —$C(OH)C(O)OY^1$ wherein $Y^1$ is H, ($C_1$-$C_6$)alkyl or benzyl, —$C(OY^2)Y^3$ wherein $Y^2$ is ($C_1$-$C_4$) alkyl and $Y^3$ is ($C_1$-$C_6$)alkyl, carboxy ($C_1$-$C_6$)alkyl, amino($C_1$-$C_4$)alkyl or mono-N—or di-N,N—($C_1$-$C_6$)alkylaminoalkyl, —$C(Y^4)Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective amount" or "therapeutically effective amount" is meant to describe an amount of compound or a composition of the present invention that is effective to treat or prevent a viral infection or a virus-related disorder.

Metabolic conjugates, such as glucuronides and sulfates which can undergo reversible conversion to the 2,3-Substituted Azaindole Derivatives are contemplated in the present invention.

The 2,3-Substituted Azaindole Derivatives may form salts, and all such salts are contemplated within the scope of this invention. Reference to a 2,3-Substituted Azaindole Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 2,3-Substituted Azaindole Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a 2,3-Substituted Azaindole Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food &

Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, choline, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

The 2,3-Substituted Azaindole Derivatives may contain asymmetric or chiral centers, and, therefore, exist in different stereoisomeric forms. It is intended that all stereoisomeric forms of the 2,3-Substituted Azaindole Derivatives as well as mixtures thereof, including racemic mixtures, form part of the present invention. In addition, the present invention embraces all geometric and positional isomers. For example, if a 2,3-Substituted Azaindole Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the 2,3-Substituted Azaindole Derivatives may be atropisomers (e.g., substituted biaryls) and are considered as part of this invention. Enantiomers can also be separated by use of chiral HPLC column.

The straight line ——— as a bond generally indicates a mixture of, or either of, the possible isomers, non-limiting example(s) include, containing (R)- and (S)-stereochemistry. For example,

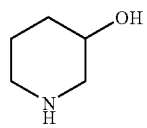

means containing both

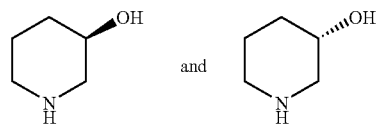 [SMILES: O[C@@H]1CCCNC1 ; O[C@H]1CCCNC1]

A dashed line ----- represents an optional bond.
Lines drawn into the ring systems, such as, for example:

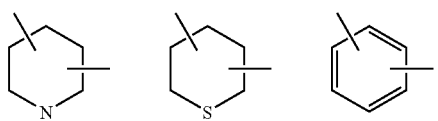

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

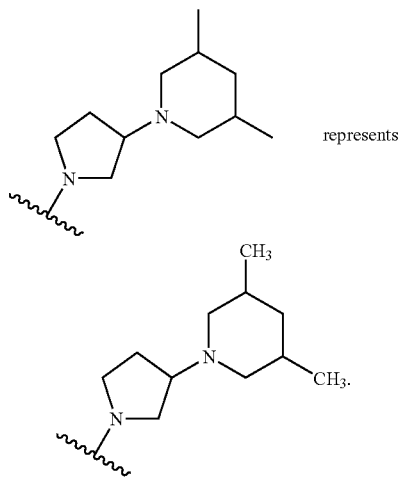

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a 2,3-Substituted Azaindole Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Such compounds are useful as therapeutic, diagnostic or research reagents. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled 2,3-Substituted Azaindole Derivatives (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled 2,3-Substituted Azaindole Derivatives can generally be prepared by following procedures analogous to those disclosed in the Schemes and/or in the Examples herein below, by substituting an appropriate isotopically labelled reagent for a non-isotopically labelled reagent.

Polymorphic forms of the 2,3-Substituted Azaindole Derivatives, and of the salts, solvates, hydrates, esters and prodrugs of the 2,3-Substituted Azaindole Derivatives, are intended to be included in the present invention.

The following abbreviations are used below and have the following meanings: ATP is adenosine-5'-triphosphate; BSA is bovine serum albumin; CDCl$_3$ is deuterated chloroform; CDI is N,N'-carbonyl diimidazole; CTP is cytidine-5'-triphosphate; DABCO is 1,4-diazabicyclo[2.2.2]octane; dba is dibenzylideneacetone; DBU is 1,8-diazabicyclo[5.4.0]undec-7-ene; DME is dimethoxyethane; DMF is N,N-dimethylformamide; DMSO is dimethylsulfoxide; dppf is 1,1'-bis(diphenylphosphino)ferrocene; DTT is 1,4-dithio-threitol; EDCI is 1-(3-dimethylaminopropyl)-3-ethylcarbodiimide; EDTA is ethylenediaminetetraacetic acid; Et$_3$N is triethylamine; EtOAc is ethyl acetate; GTP is guanosine-5'-triphosphate; HPLC is high performance liquid chromatography; MeOH is methanol; NBS is N-bromosuccinimide; NIS is N-iodosuccinimide; PPA is polyphosphoric acid; TBAF is tetrabutylammonium fluoride; THF is tetrahydrofuran; TLC is thin-layer chromatography; TMS is trimethylsilyl; and UTP is uridine-5'-triphosphate.

The 2,3-Substituted Azaindole Derivatives of Formula (I)

The present invention provides 2,3-Substituted Azaindole Derivatives having the formula:

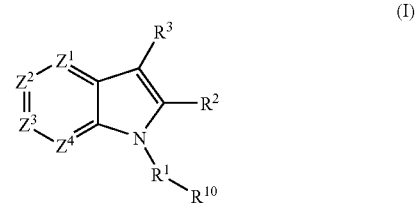

(I)

and pharmaceutically acceptable salts, solvates, esters and prodrugs thereof, wherein $Z^1$, $Z^2$, $Z^3$, $Z^4$, $R^1$, $R^2$, $R^3$ and $R^{10}$ are defined above for the compounds of formula (I).

In one embodiment $Z^1$ is —N—.
In another embodiment $Z^1$ is —N(O)—.
In another embodiment $Z^1$ is —C(R$^4$)—.
In another embodiment $Z^1$ is —CH—.
In one embodiment $Z^2$ is —N—.
In another embodiment $Z^2$ is —N(O)—.
In another embodiment $Z^2$ is —C(R$^5$)—.
In another embodiment $Z^2$ is —CH—.
In one embodiment $Z^3$ is —N—.
In another embodiment $Z^3$ is —N(O)—.
In another embodiment $Z^3$ is —C(R$^6$)—.
In another embodiment $Z^3$ is —CH—.
In one embodiment $Z^4$ is —N—.
In another embodiment $Z^4$ is —N(O)—.
In another embodiment $Z^4$ is —C(R$^7$)—.
In another embodiment $Z^4$ is —CH—.
In another embodiment, one of $Z^1$ and $Z^4$ is —N—; $Z^2$ is —C(R$^5$)—; $Z^3$ is —C(R$^6$)—; and R$^5$ and R$^6$ are each independently selected from H, —O-alkyl and halo.
In another embodiment, $Z^1$ is —N—; $Z^2$ is —C(R$^5$)—; $Z^3$ is —C(R$^6$)—; and R$^5$ and R$^6$ are each independently selected from H, —O-alkyl and halo.
In another embodiment, $Z^4$ is —N—; $Z^2$ is —C(R$^5$)—; $Z^3$ is —C(R$^6$)—; and R$^5$ and R$^6$ are each independently selected from H, —O-alkyl and halo.
In another embodiment, one of $Z^1$, $Z^2$, $Z^3$ and $Z^4$ is —N— and the others are—other than —N— or —N(O)—.
In still another embodiment, one of $Z^1$, $Z^2$, $Z^3$ and $Z^4$ is —N— and the others are —CH—.
In another embodiment, two of $Z^1$, $Z^2$, $Z^3$ and $Z^4$ are —N—.
In another embodiment, three of $Z^1$, $Z^2$, $Z^3$ and $Z^4$ are —N—.
In still another embodiment, $Z^1$, $Z^2$, $Z^3$ and $Z^4$ are each —N—
In one embodiment, $Z^1$ is —N— and $Z^2$, $Z^3$ and $Z^4$ are each —CH—.
In another embodiment, $Z^2$ is —N— and $Z^1$, $Z^3$ and $Z^4$ are each —CH—.
In still another embodiment, $Z^3$ is —N— and $Z^1$, $Z^2$ and $Z^4$ are each —CH—.
In another embodiment, $Z^4$ is —N— and $Z^1$, $Z^2$ and $Z^3$ are each —CH—.
In one embodiment, $Z^2$ is —N— and $Z^2$ is —C(R$^6$)—.
In another embodiment, $Z^3$ is —N— and $Z^2$ is —C(R$^5$)—.
In another embodiment, $Z^4$ is —N— and $Z^2$ is —C(R$^5$)—.
In one embodiment, $Z^1$ is —N— and $Z^3$ is —C(R$^6$)—.

In another embodiment, $Z^2$ is —N— and $Z^3$ is —C($R^6$)—.
In another embodiment, $Z^4$ is —N— and $Z^3$ is —C($R^6$)—.
In another embodiment, $R^4$ and $R^5$, or $R^5$ and $R^6$, or $R^6$ and $R^7$, together with the carbon atoms to which they are attached, combine to form a heterocycloalkyl or heteroaryl group.

In one embodiment, $R^1$ is bond.
In another embodiment, $R^1$ is —[C($R^{12}$)$_2$]$_r$—.
In another embodiment, $R^1$ is —[C($R^{12}$)$_2$]$_r$—O—[C($R^{12}$)$_2$]$_q$—.
In still another embodiment, $R^1$ is —[C($R^{12}$)$_2$]$_r$—N($R^9$)—[C($R^{12}$)$_2$]$_q$—.
In yet another embodiment, $R^1$ is —[C($R^{12}$)$_2$]$_q$—CH=CH—[C($R^{12}$)$_2$]$_q$—.
In another embodiment, $R^1$ is —[C($R^{12}$)$_2$]$_q$—C≡C—[C($R^{12}$)$_2$]$_q$.
In a further embodiment, $R^1$ is —[C($R^{12}$)$_2$]$_q$—SO$_2$—[C($R^{12}$)$_2$]$_q$—.
In another embodiment, $R^1$ is —CH$_2$— or

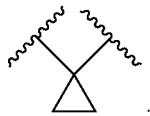 [SMILES: *C1(*)CC1]

In another embodiment, $R^1$ is —CH$_2$—.
In one embodiment, $R^{10}$ is —H and $R^1$ is other than a bond.
In another embodiment, $R^{10}$ is aryl.
In another embodiment, $R^{10}$ is cycloalkyl.
In another embodiment, $R^{10}$ is cycloalkenyl.
In still another embodiment, $R^{10}$ is heterocycloalkenyl.
In another embodiment, $R^{10}$ is heteroaryl.
In another embodiment, $R^{10}$ is heterocycloalkyl.
In another embodiment, $R^{10}$ is aryl or heteroaryl.
In another embodiment, —$R^{10}$ is:

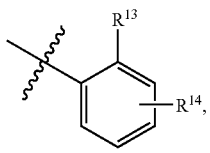 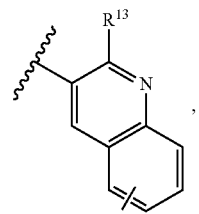

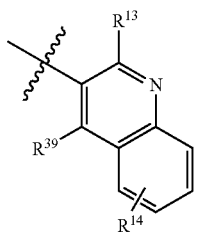 or 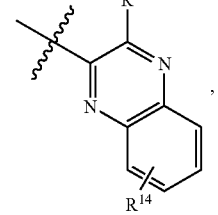, wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, —$R^{10}$ is:

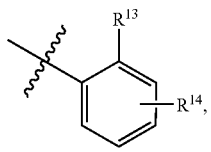

wherein $R^{13}$ is H or F, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In still another embodiment, $R^{10}$ is phenyl which can be optionally substituted as set forth in formula (I).

In another embodiment, $R^{10}$ is phenyl, which is substituted with from 1-4 groups independently selected from: halo, —NH$_2$, —NHSO$_2$-alkyl, haloalkyl, methoxy, —O-haloalkyl, -alkylene-NHC(O)NH-alkyl, alkyl, hydroxy, —CN, —C(O)NH$_2$ or -alkylene-NH$_2$.

In still another embodiment, $R^{10}$ is phenyl, which is substituted with from 1-4 F atoms.

In another embodiment, $R^{10}$ is phenyl, which is substituted with 2 F atoms.

In yet another embodiment, $R^{10}$ is phenyl, which is substituted with one F atoms.

In another embodiment, —$R^{10}$ is:

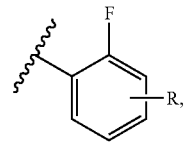

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In another embodiment, $R^{10}$ is:

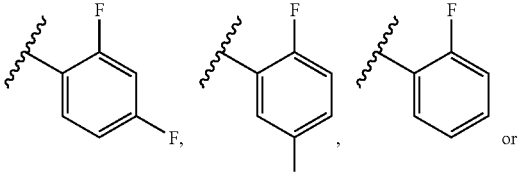

In another embodiment, R$^1$ is —CH$_2$— and —R$^{10}$ is:

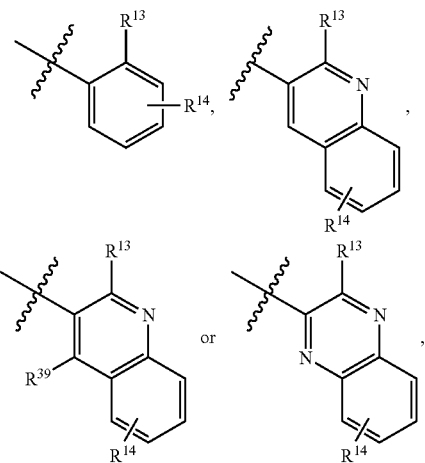

wherein R$^{13}$ is H or F and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, —R$^1$ is —CH$_2$— and R$^{10}$ is:

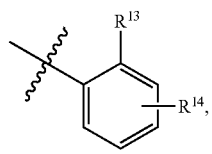

wherein R$^{13}$ is H or F and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In one embodiment, —R$^1$-R$^{10}$ is benzyl.

In another embodiment, —R$^1$-R$^{10}$ is benzyl, wherein the phenyl moiety of the benzyl group is substituted with from 1-4 groups independently selected from: halo, —NH$_2$, —NHSO$_2$-alkyl, haloalkyl, methoxy, —O-haloalkyl, -alkylene-NHC(O)NH-alkyl, alkyl, hydroxy, —CN, —C(O)NH$_2$ or -alkylene-NH$_2$.

In still another embodiment, —R$^1$-R$^{10}$ is

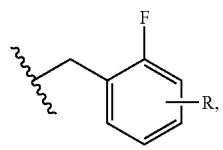

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In still another embodiment, —R$^1$-R$^{10}$ is alkyl.

In yet another embodiment, —R$^1$-R$^{10}$ is benzyl, wherein the phenyl moiety of the benzyl group is substituted with 1 or 2 fluorine atoms.

In yet another embodiment, —R$^1$-R$^{10}$ is benzyl, wherein the phenyl moiety of the benzyl group is substituted with 1 or 2 methyl groups.

In another embodiment, —R$^1$ is —CH$_2$— and R$^{10}$ is:

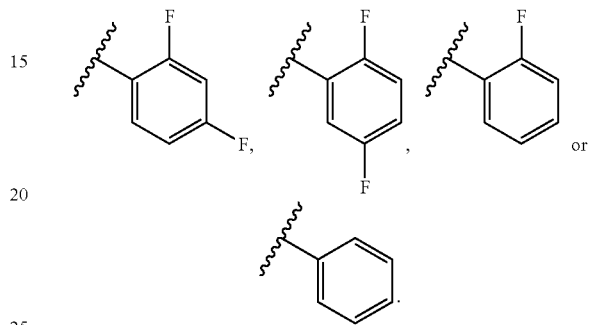

In a further embodiment, —R$^1$-R$^{10}$ is —CH$_2$-cycloalkyl.

In one embodiment, R$^2$ is —[C(R$^{12}$)$_2$]$_q$—C(O)N(R$^9$)SO$_2$R$^{11}$.

In another embodiment, R$^2$ is —[C(R$^{12}$)$_2$]$_q$—C(O)N(R$^9$)SOR$^{11}$.

In another embodiment, R$^2$ is —[C(R$^{12}$)$_2$]$_q$—C(O)N(R$^9$)SO$_2$N(R$^{11}$)$_2$.

In still another embodiment, R$^2$ is

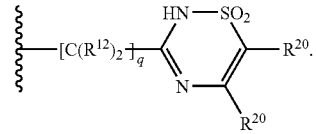

In another embodiment, R$^2$ is —C(O)N(R$^9$)SO$_2$R$^{11}$.
In another embodiment, R$^2$ is —C(O)NHSO$_2$R$^{11}$.
In another embodiment, R$^2$ is —C(O)NHSO$_2$R$^{11}$ and R$^{11}$ is —[C(R$^{12}$)$_2$]$_q$-alkyl.
In yet another embodiment, R$^2$ is —C(O)NHSO$_2$R$^{11}$ and R$^{11}$ is —[C(R$^{12}$)$_2$]$_q$-aryl.
In another embodiment, R$^2$ is —C(O)NHSO$_2$R$^{11}$ and R$^{11}$ is —[C(R$^{12}$)$_2$]$_q$-cycloalkyl.
In a further embodiment, R$^2$ is —C(O)NHSO$_2$R$^{11}$ and R$^{11}$ is —[C(R$^{12}$)$_2$]$_q$-heterocycloalkyl.
In another embodiment, R$^2$ is —C(O)NHSO$_2$R$^{11}$ and R$^{11}$ is —[C(R$^{12}$)$_2$]$_q$-heteroaryl.
In another embodiment, R$^2$ is —C(O)NHSO$_2$R$^{11}$ and R$^{11}$ is —[C(R$^{12}$)$_2$]$_q$-haloalkyl.
In still another embodiment, R$^2$ is —C(O)NHSO$_2$R$^{11}$ and R$^{11}$ is —[C(R$^{12}$)$_2$]$_q$-hydroxyalkyl.
In still another embodiment, R$^2$ is —C(O)NHSO$_2$R$^{11}$ and R$^{11}$ is alkyl.
In yet another embodiment, R$^2$ is —C(O)NHSO$_2$R$^{11}$ and R$^{11}$ is aryl.
In another embodiment, R$^2$ is —C(O)NHSO$_2$R$^{11}$ and R$^{11}$ is cycloalkyl.
In a further embodiment, R$^2$ is —C(O)NHSO$_2$R$^{11}$ and R$^{11}$ is heterocycloalkyl.

In another embodiment, $R^2$ is —C(O)NHSO$_2$R$^{11}$ and $R^{11}$ is heteroaryl.

In another embodiment, $R^2$ is —C(O)NHSO$_2$R$^{11}$ and $R^{11}$ is haloalkyl.

In still another embodiment, $R^2$ is —C(O)NHSO$_2$R$^{11}$ and $R^{11}$ is hydroxyalkyl.

In another embodiment, $R^2$ is —C(O)NHSO$_2$R$^{11}$ and $R^{11}$ is alkyl or cycloalkyl.

In another embodiment, $R^2$ is —C(O)NHSO$_2$R$^{11}$ and $R^{11}$ is —[C(R$^{12}$)$_2$]$_q$-phenyl.

In a further embodiment, $R^2$ is —C(O)NHSO$_2$R$^{11}$ and $R^{11}$ is benzyl.

In another embodiment, $R^2$ is —C(O)NHSO$_2$R$^{11}$ and $R^{11}$ is naphthyl.

In yet another embodiment, $R^2$ is —C(O)NHSO$_2$R$^{11}$ and $R^{11}$ is —NH$_2$ or —N(CH$_3$)$_2$.

In another embodiment, $R^2$ is —C(O)NHSO$_2$R$^{11}$ and $R^{11}$ is alkyl aryl, cycloalkyl, haloalkyl, heteroaryl or heterocycloalkyl.

In another embodiment, $R^2$ is —C(O)NHSO$_2$R$^{11}$ and $R^{11}$ is methyl, cyclopropyl or phenyl.

In one embodiment, $R^2$ is —C(O)NHSO$_2$R$^{11}$ and $R^{11}$ is alkyl or cycloalkyl.

In another embodiment, $R^2$ is —C(O)NHSO$_2$N(R$^9$)$_2$ and $R^9$ is H, alkyl or cycloalkyl.

In another embodiment, $R^2$ is —C(O)NHSO$_2$N(R$^9$)$_2$ and $R^9$ is alkyl or cycloalkyl.

In a further embodiment, $R^2$ is —C(O)NHSO$_2$R$^{11}$ and $R^{11}$ is H, methyl, ethyl, or cyclopropyl.

In another embodiment, $R^2$ is —C(O)NHSO$_2$R$^{11}$ and $R^{11}$ is methyl or cyclopropyl.

In still another embodiment, $R^2$ is —C(O)NHSO$_2$R$^{11}$ and $R^{11}$ is cyclopropyl.

In another embodiment, $R^2$ is —C(O)NHSO$_2$R$^{11}$ and $R^{11}$ is methyl.

In one embodiment, $R^2$ is —C(O)NHSO$_2$N(R$^9$)$_2$ and $R^9$ is H, methyl, ethyl or cyclopropyl.

In another embodiment, $R^2$ is —C(O)NHSO$_2$N(R$^9$)$_2$ and $R^9$ is H or methyl.

In still another embodiment, $R^2$ is —C(O)NHSO$_2$R$^{11}$ and $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, hydroxy, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$.

In yet another embodiment, $R^2$ is —C(O)NHSO$_2$R$^{11}$ and $R^{11}$ is —[C(R$^{12}$)$_2$]$_q$—NHSO$_2$-alkyl, —[C(R$^{12}$)$_2$]-O-alkyl, or —[C(R$^{12}$)$_2$]-alkyl.

In another embodiment, $R^3$ is

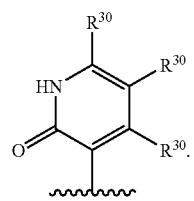

In another embodiment, $R^3$ is

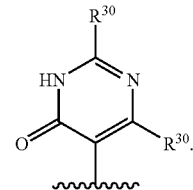

In still another embodiment, $R^3$ is

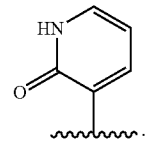

In another embodiment, $R^3$ is

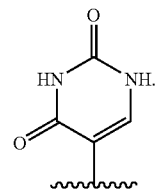 [SMILES: *c1c[nH]c(=O)[nH]c1=O]

In another embodiment, $R^1$ is —CH$_2$—, —CH$_2$CH$_2$— or —CH(CH$_3$)—, and $R^2$ is —C(O)NHSO$_2$R$^{11}$.

In another embodiment, $R^1$ is —CH$_2$—, —CH$_2$CH$_2$— or —CH(CH$_3$)—, and $R^{10}$ is

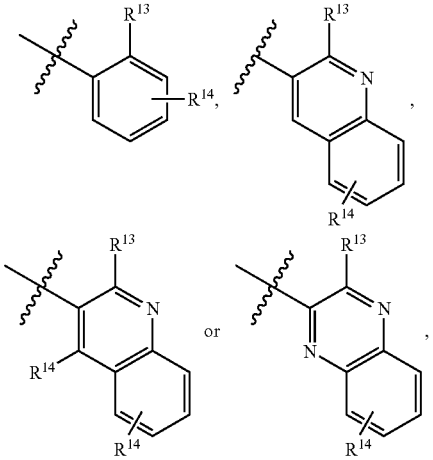

wherein $R^{13}$ is H, F, Br or Cl, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, $R^1$ is —CH$_2$—, —CH$_2$CH$_2$— or —CH(CH$_3$)—; $R^2$ is —C(O)NHSO$_2$R$^{11}$; and $R^{10}$ is

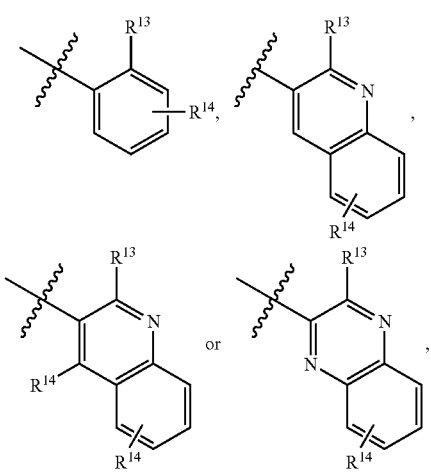

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In another embodiment, $R^1$ is —$CH_2$—, —$CH_2CH_2$— or —$CH(CH_3)$—; $R^2$ is —C(O)$NHSO_2R^{11}$; and $R^{10}$ is

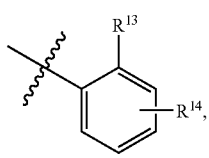

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In another embodiment, $R^1$ is —$CH_2$—, —$CH_2CH_2$— or —$CH(CH_3)$—; $R^2$ is —C(O)$NHSO_2R^{11}$; and $R^{10}$ is

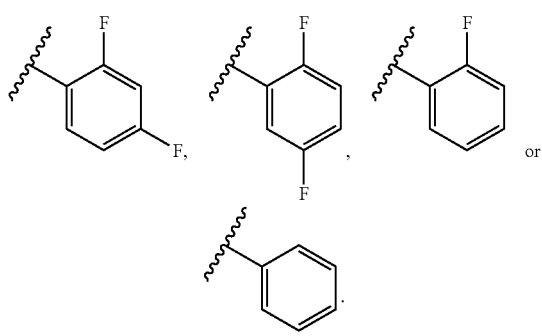

In another embodiment, $R^1$ is —$CH_2$—, —$CH_2CH_2$— or —$CH(CH_3)$—; $R^2$ is —C(O)$NHSO_2R^{11}$; one of $Z^1$, $Z^2$, $Z^3$ and $Z^4$ is —N— and the others are not —N— or —N(O)—; and $R^{10}$ is

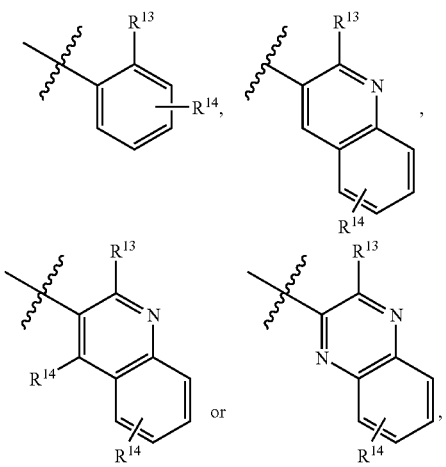

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In another embodiment, $R^1$ is —$CH_2$—, —$CH_2CH_2$— or —$CH(CH_3)$—; $R^2$ is —C(O)$NHSO_2R^{11}$;

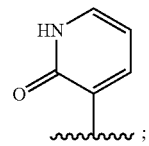 [SMILES: *c1ccc[nH]c1=O]

one of $Z^1$, $Z^2$, $Z^3$ and $Z^4$ is —N— and the others are not —N— or —N(O)—; and $R^{10}$ is

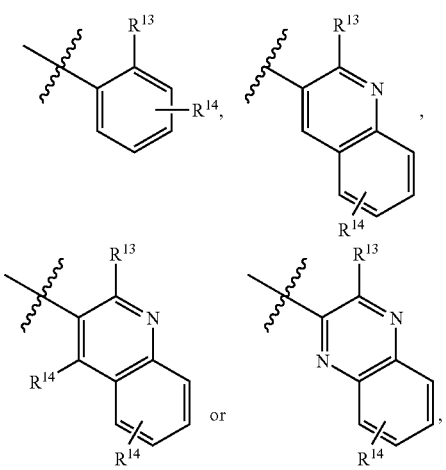

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In another embodiment, $R^1$ is —$CH_2$—, —$CH_2CH_2$— or —$CH(CH_3)$—; $R^2$ is —$C(O)NHSO_2R^{11}$; $R^3$ is

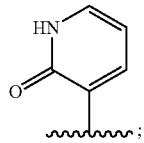

one of $Z^1$, $Z^2$, $Z^3$ and $Z^4$ is —N— and the others are not —N— or —N(O)—; and $R^{10}$ is

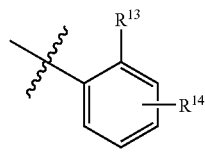

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In another embodiment, $R^1$ is —$CH_2$—, —$CH_2CH_2$— or —$CH(CH_3)$—; $R^2$ is —$C(O)NHSO_2R^{11}$; $R^3$ is

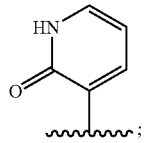

one of $Z^1$, $Z^2$, $Z^3$ and $Z^4$ is —N— and the others are not —N— or —N(O)—; and $R^{10}$ is

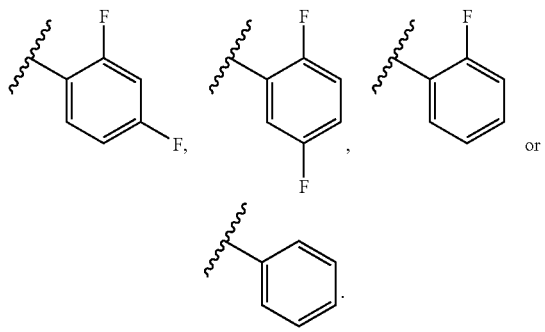

In another embodiment, $R^1$ is —$CH_2$—, —$CH_2CH_2$— or —$CH(CH_3)$—; $R^2$ is —$C(O)NHSO_2R^{11}$; $R^3$ is

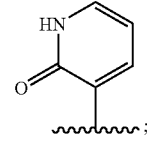 [SMILES: *c1ccc[nH]c1=O]

one of $Z^1$, $Z^2$, $Z^3$ and $Z^4$ is —N— and the others are not —N— or —N(O)—; $R^{10}$ is

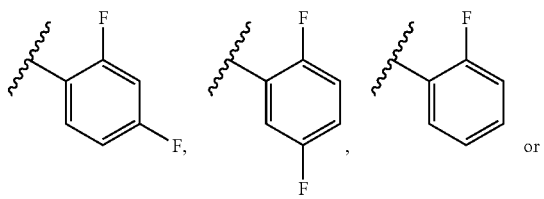

and $R^{11}$ is alkyl or cycloalkyl.

In another embodiment, $R^1$ is —$CH_2$—, —$CH_2CH_2$— or —$CH(CH_3)$—; $R^2$ is —$C(O)NHSO_2R^{11}$; $R^3$ is

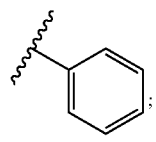

one of $Z^1$, $Z^2$, $Z^3$ and $Z^4$ is —N— and the others are not —N— or —N(O)—; $R^{10}$ is

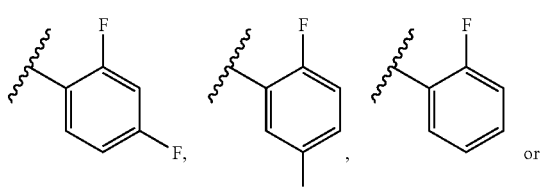

and $R^{11}$ is methyl or cyclopropyl.

In another embodiment, $R^2$ is —C(O)NHSO$_2$R$^{11}$, and $R^{10}$ is

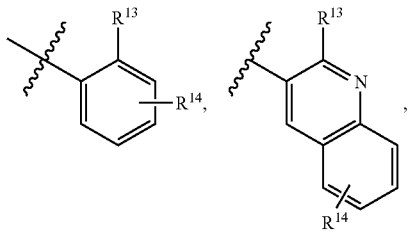

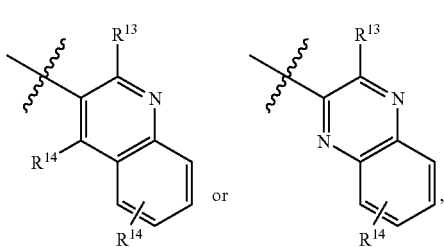 or wherein $R^{13}$ is H, F, Br or Cl, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In one embodiment, $R^2$ is —C(O)NHSO$_2$R$^{11}$ and $R^3$ is

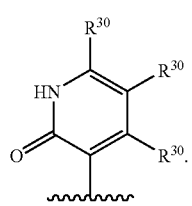

In another embodiment, $R^2$ is —C(O)NHSO$_2$R$^{11}$; $R^{11}$ is alkyl or cycloalkyl; and $R^3$ is

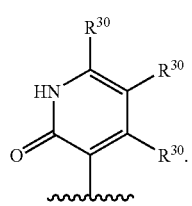

In another embodiment, $R^2$ is —C(O)NHSO$_2$R$^{11}$; $R^{11}$ is methyl or cyclopropyl; and $R^3$ is

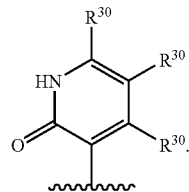

In one embodiment, $R^1$ is —CH$_2$—; $R^2$ is —C(O)NHSO$_2$R$^{11}$ and $R^{10}$ is

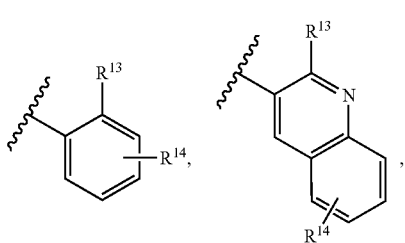

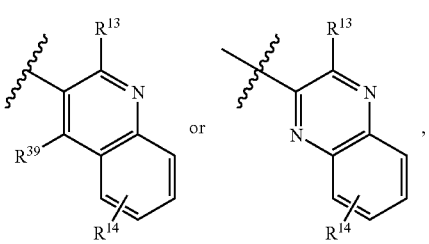 or wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, $R^1$ is —CH$_2$—; $R^2$ is —C(O)NHSO$_2$R$^{11}$ and $R^{10}$ is

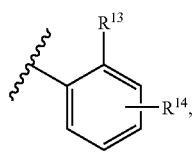

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, $R^1$ is —CH$_2$—; $R^2$ is —C(O)NHSO$_2R^{11}$ and $R^{10}$ is

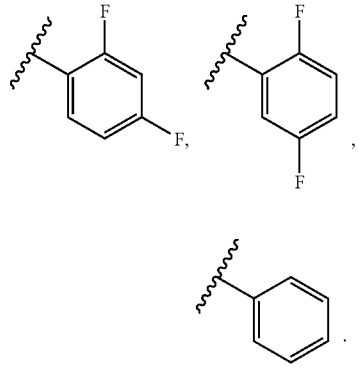

In one embodiment, $R^1$ is —CH$_2$—; $R^2$ is —C(O)NHSO$_2R^{11}$ and $R^3$ is

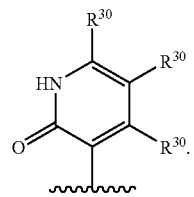

In another embodiment, $R^1$ is —CH$_2$—; $R^2$ is —C(O)NHSO$_2R^{11}$; $R^1$ is alkyl or cycloalkyl; and $R^3$ is

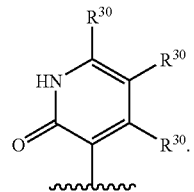

In another embodiment, $R^1$ is —CH$_2$—; $R^2$ is —C(O)NHSO$_2R^{11}$; $R^{11}$ is methyl or cyclopropyl; and $R^3$ is

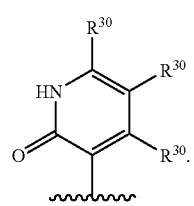

In one embodiment, $R^1$ is —CH$_2$—; $R^{11}$ is

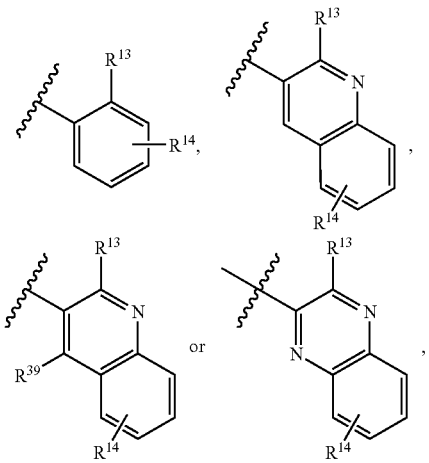

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; $R^2$ is —C(O)NHSO$_2R^{11}$ and $R^3$ is

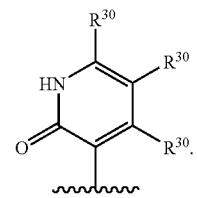

In another embodiment, $R^1$ is —CH$_2$—; $R^{10}$ is

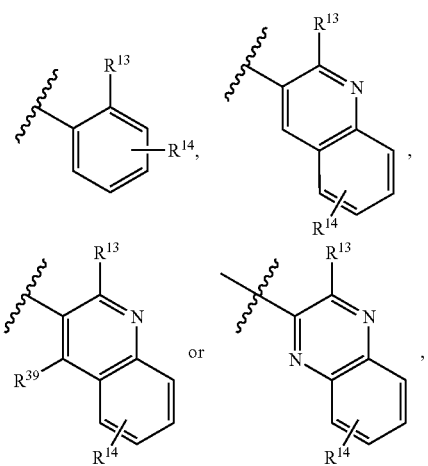

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; R$^2$ is —C(O)NHSO$_2$R$^{11}$; R$^{11}$ is alkyl or cycloalkyl; and R$^3$ is

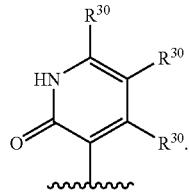

In another embodiment, R$^1$ is —CH$_2$—; R$^{10}$ is

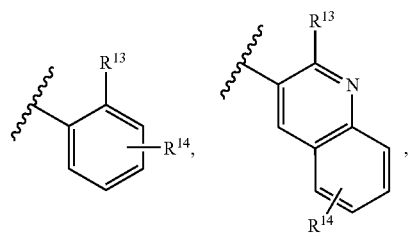

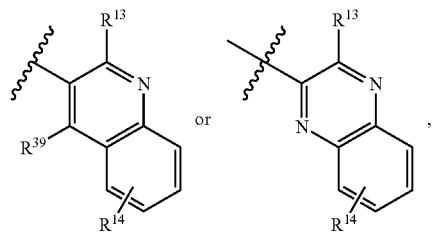

wherein R$^{13}$ is H or F and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; R$^2$ is —C(O)NHSO$_2$R$^{11}$; R$^{11}$ is methyl or cyclopropyl; and R$^3$ is

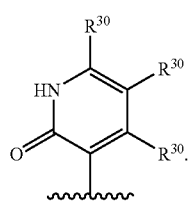

In one embodiment, R$^1$ is —CH$_2$—; R$^{10}$ is phenyl, which can be optionally substituted as set forth in formula (I); R$^2$ is —C(O)NHSO$_2$R$^{11}$ and R$^3$ is

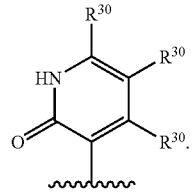

In another embodiment, R$^1$ is —CH$_2$—; R$^{10}$ is phenyl, which can be optionally substituted as set forth in formula (I); R$^2$ is —C(O)NHSO$_2$R$^{11}$; R$^{11}$ is alkyl or cycloalkyl; and R$^3$ is

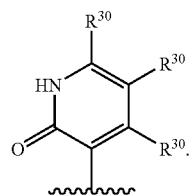

In another embodiment, R$^1$ is —CH$_2$—; R$^{10}$ is phenyl, which can be optionally substituted as set forth in formula (I); R$^2$ is —C(O)NHSO$_2$R$^{11}$; R$^{11}$ is methyl or cyclopropyl; and R$^3$ is

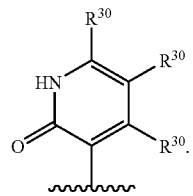

In one embodiment, R$^1$ is —CH$_2$—; R$^{10}$ is

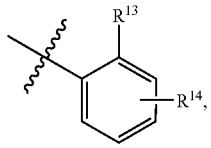

wherein R$^{13}$ is H or F and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; R$^2$ is —C(O)NHSO$_2$R$^{11}$ and R$^3$ is

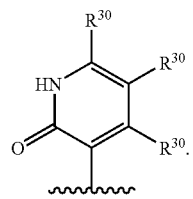

In another embodiment, $R^1$ is —$CH_2$—; $R^{10}$ is

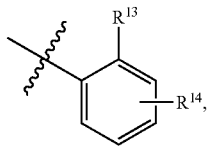

wherein $R^{13}$ is H or F and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; $R^2$ is —C(O)$NHSO_2R^{11}$; $R^{11}$ is alkyl or cycloalkyl; and $R^3$ is

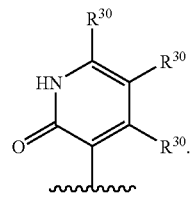

In another embodiment, $R^1$ is —$CH_2$—; $R^{10}$ is

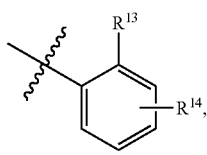

wherein $R^{13}$ is H or F and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; $R^2$ is —C(O)$NHSO_2R^{11}$; $R^{11}$ is methyl or cyclopropyl; and $R^3$ is

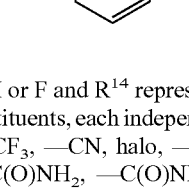

In one embodiment, $R^1$ is —$CH_2$—; $R^{10}$ is phenyl, which can be optionally substituted with one or two F atoms; $R^2$ is —C(O)$NHSO_2R^{11}$ and $R^3$ is

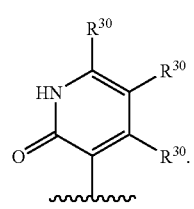

In another embodiment, $R^1$ is —$CH_2$—; $R^{10}$ is phenyl, which can be optionally substituted with one or two F atoms; $R^2$ is —C(O)$NHSO_2R^{11}$; $R^{11}$ is alkyl or cycloalkyl; and $R^3$ is

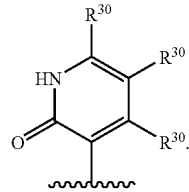

In another embodiment, $R^1$ is —$CH_2$—; $R^{10}$ is phenyl, which can be optionally substituted with one or two F atoms; $R^2$ is —C(O)$NHSO_2R^{11}$; $R^{11}$ is methyl or cyclopropyl; and $R^3$ is

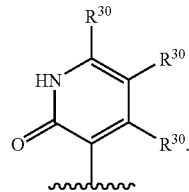

In one embodiment, $R^1$ is —$CH_2$—; $R^2$ is —C(O)$NHSO_2R^{11}$; one of $Z^1$, $Z^2$, $Z^3$ and $Z^4$ is —N— and the others are not —N— or —N(O)—; and $R^{10}$ is

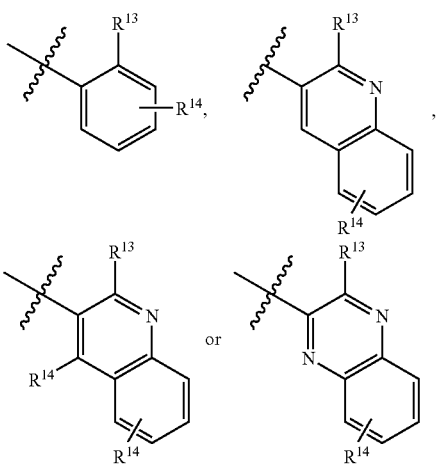

wherein $R^{13}$ is H or F, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$ alkyl, —$SO_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, R$^1$ is —CH$_2$—; R$^2$ is —C(O)NHSO$_2$R$^{11}$; R$^3$ is

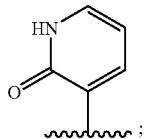 [SMILES: *c1ccc[nH]c1=O]

one of Z$^1$, Z$^2$, Z$^3$ and Z$^4$ is —N— and the others are not —N— or —N(O)—; and R$^{10}$ is

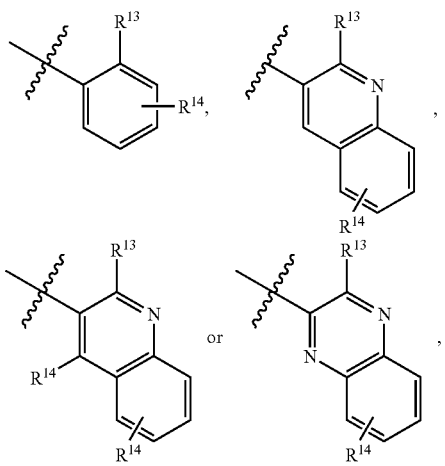

wherein R$^{13}$ is H or F, and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, R$^1$ is —CH$_2$—; R$^2$ is —C(O)NHSO$_2$R$^{11}$; R$^3$ is

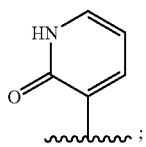

one of Z$^1$, Z$^2$, Z$^3$ and Z$^4$ is —N— and the others are not —N— or —N(O)—; and R$^{10}$ is

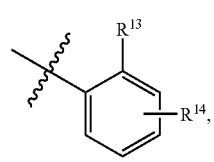

wherein R$^{13}$ is H or F, and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In still another embodiment, R$^1$ is —CH$_2$—; R$^2$ is —C(O)NHSO$_2$R$^{11}$; R$^3$ is

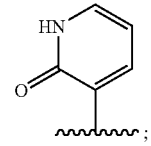

one of Z$^1$, Z$^2$, Z$^3$ and Z$^4$ is —N— and the others are not —N— or —N(O)—; and R$^{10}$ is

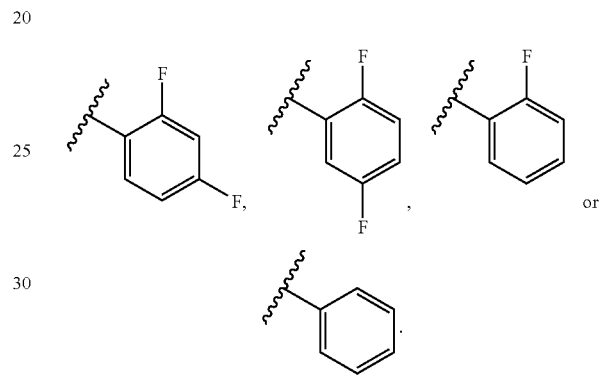

In yet another embodiment, R$^1$ is —CH$_2$—; R$^2$ is —C(O)NHSO$_2$R$^{11}$; R$^{11}$ is alkyl or cycloalkyl; R$^3$ is

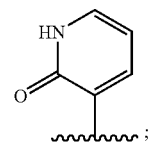

one of Z$^1$, Z$^2$, Z$^3$ and Z$^4$ is —N— and the others are not —N— or —N(O)—; and R$^{11}$ is

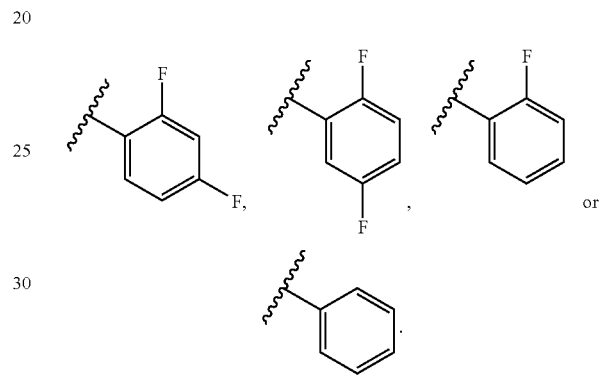

In a further embodiment, R$^1$ is —CH$_2$—; R$^2$ is —C(O)NHSO$_2$R$^{11}$; R$^{11}$ is methyl or cyclopropyl; R$^3$ is

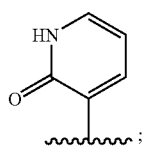 [SMILES: *c1ccc[nH]c1=O]

one of $Z^1$, $Z^2$, $Z^3$ and $Z^4$ is —N— and the others are not —N— or —N(O)—; and $R^{10}$ is

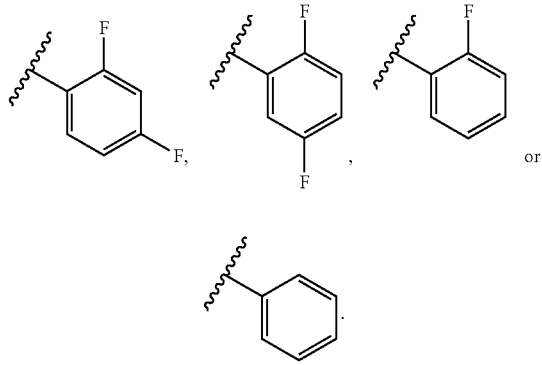

In one embodiment, the compounds of formula (I) have the formula (Ia):

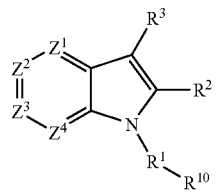

(Ia)

wherein:

$Z^1$ is —N—, —N(O)— or —C($R^4$)—;
$Z^2$ is —N—, —N(O)— or —C($R^5$)—;
$Z^3$ is —N—, —N(O)— or —C($R^6$)—;
$Z^4$ is —N—, —N(O)— or —C($R^7$)—, such that one of $Z^1$, $Z^2$, $Z^3$ and $Z^4$ is —N— or —N(O)— and the others are not —N— or —N(O)—;

$R^1$ is —CH$_2$—, —CH$_2$CH$_2$—, —CH(CH$_3$)—

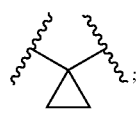 [SMILES: *C1(*)CC1]

$R^2$ is —C(O)N($R^9$)SO$R^{11}$, —C(O)N($R^9$)SO$_2R^{11}$, or —C(O)N($R^9$)SO$_2$N($R^{11}$)$_2$;

$R^3$ is:

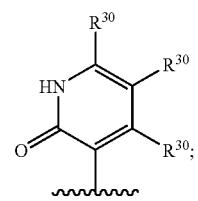

$R^4$, $R^5$, $R^6$ and $R^7$ are each, independently, H, alkyl, -cycloalkyl, -heterocycloalkyl, haloalkyl, halo, hydroxy, —O-alkyl, —O-haloalkyl —NH$_2$, —NH-alkyl or —N(alkyl)$_2$;

$R^{10}$ is:

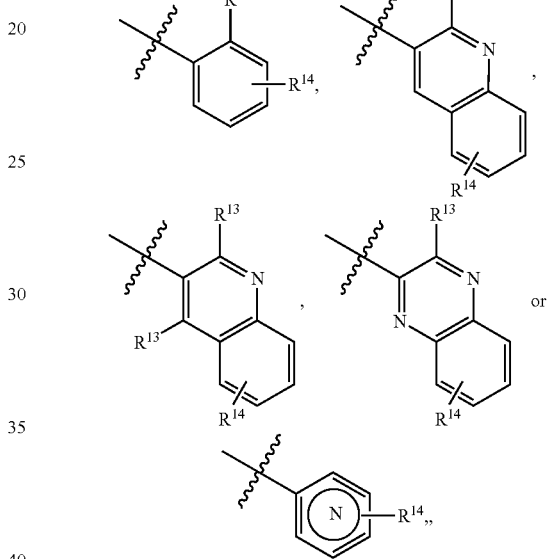

such that when $R^1$ is a bond, $R^{10}$ is not H;

each occurrence of $R^{11}$ is independently alkyl, aryl, cycloalkyl, haloalkyl, heteroaryl, heterocycloalkyl or hydroxyalkyl;

each occurrence of $R^{12}$ is independently H, halo, —N(alkyl)$_2$, —OH, —O-alkyl, alkyl, cycloalkyl or heterocycloalkyl, or two $R^{12}$ groups, together with the carbon atoms to which they are attached, join to form a cycloalkyl, heterocycloalkyl or C=O group;

$R^{13}$ is H or halo;

$R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl;

each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form a –3- to 7-membered ring selected from aryl, cycloalkyl, heteroaryl and heterocycloalkyl;

each occurrence of q is independently an integer ranging from 0 to 4;

each occurrence of r is independently an integer ranging from 1 to 4; and

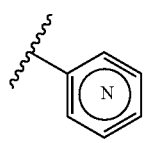
represents a pyridyl group, wherein the ring nitrogen atom can be at any of the five unsubstituted ring atom positions.
In one embodiment, the compounds of formula (I) are in purified form.
Non-limiting examples of compounds of formula (I) include the following compounds:
| Cmpd No. | Structure | MS (M + H) |
|---|---|---|
| 1 | | 493.9 |
| 2 | | 493.9 |
| 3 | | 471.5 |
| 4 | 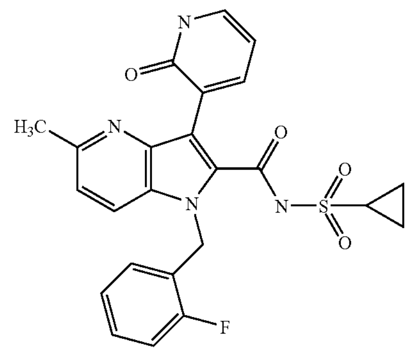 [SMILES: Cc1ccc2c(n1)c(-c1ccc[nH]c1=O)c(C(=O)NS(=O)(=O)C1CC1)n2Cc1ccccc1F] | 481.5 |
| 5 | 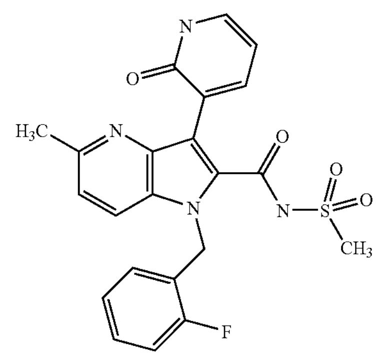 [SMILES: Cc1ccc2c(n1)c(-c1ccc[nH]c1=O)c(C(=O)NS(C)(=O)=O)n2Cc1ccccc1F] | 455.5 |
| 13 | 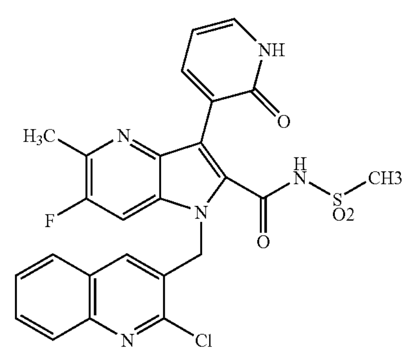 [SMILES: Cc1nc2c(-c3ccc[nH]c3=O)c(C(=O)NS(C)(=O)=O)n(Cc3cc4ccccc4nc3Cl)c2cc1F] | NA |
| 14 | 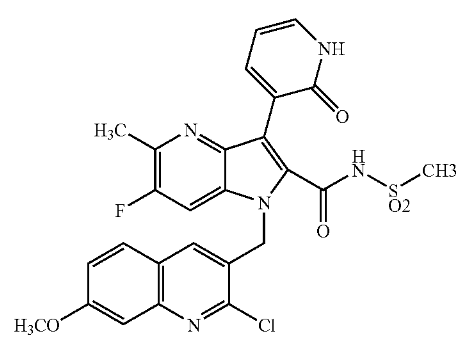 [SMILES: COc1ccc2cc(Cn3c(C(=O)NS(C)(=O)=O)c(-c4ccc[nH]c4=O)c4nc(C)c(F)cc43)c(Cl)nc2c1] | NA |

-continued

| Cmpd No. | Structure | MS (M + H) |
|---|---|---|
| 15 | 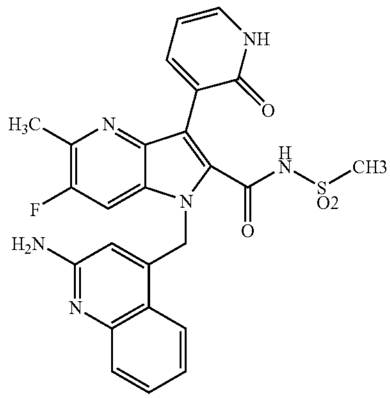 | NA |
| 16 | 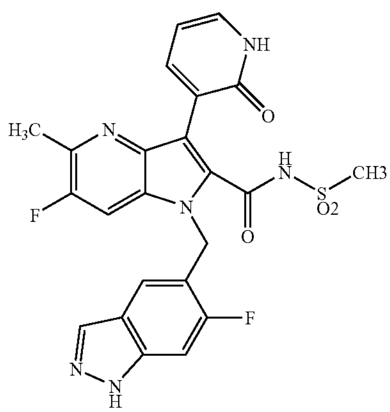 | NA |
| 17 | 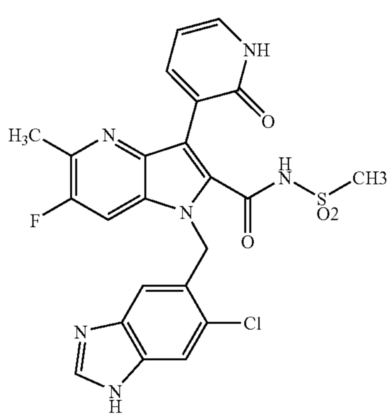 | NA |
| 18 | | NA |

NA = not available and pharmaceutically acceptable salts, solvates, esters and prodrugs thereof.

The 2,3-Substituted Azaindole Derivatives of Formula (II)

The present invention provides 2,3-Substituted Azaindole Derivatives having the formula:

$$(II)$$

and pharmaceutically acceptable salts, solvates, esters and prodrugs thereof, wherein $Z^1$, $Z^2$, $Z^3$, $Z^4$, $R^1$, $R^2$, $R^3$ and $R^{10}$ are defined above for the compounds of formula (II).

In one embodiment $Z^1$ is —N—.
In another embodiment $Z^1$ is —N(O)—.
In another embodiment $Z^1$ is —C($R^4$)—.
In another embodiment $Z^1$ is —CH—.
In one embodiment $Z^2$ is —N—.
In another embodiment $Z^2$ is —N(O)—.
In another embodiment $Z^2$ is —C($R^5$)—.
In another embodiment $Z^2$ is —CH—.
In one embodiment $Z^3$ is —N—.
In another embodiment $Z^3$ is —N(O)—.
In another embodiment $Z^3$ is —C($R^6$)—.
In another embodiment $Z^3$ is —CH—.
In one embodiment $Z^4$ is —N—.
In another embodiment $Z^4$ is —N(O)—.
In another embodiment $Z^4$ is —C($R^7$)—.
In another embodiment $Z^4$ is —CH—.
In another embodiment, one of $Z^1$ and $Z^4$ is —N—; $Z^2$ is —C($R^5$)—; $Z^3$ is —C($R^6$)—; and $R^5$ and $R^6$ are each independently selected from H, —O-alkyl and halo.
In another embodiment, $Z^1$ is —N—; $Z^2$ is —C($R^5$)—; $Z^3$ is —C($R^6$)—; and $R^5$ and $R^6$ are each independently selected from H, —O-alkyl and halo.
In another embodiment, $Z^4$ is —N—; $Z^2$ is —C($R^5$)—; $Z^3$ is —C($R^6$)—; and $R^5$ and $R^6$ are each independently selected from H, —O-alkyl and halo.

In another embodiment, one of $Z^1$, $Z^2$, $Z^3$ and $Z^4$ is —N— and the others are other than —N— or —N(O)—.

In still another embodiment, one of $Z^1$, $Z^2$, $Z^3$ and $Z^4$ is —N— and the others are —CH—.

In another embodiment, two of $Z^1$, $Z^2$, $Z^3$ and $Z^4$ are —N—.

In another embodiment, three of $Z^1$, $Z^2$, $Z^3$ and $Z^4$ are —N—.

In still another embodiment, $Z^1$, $Z^2$, $Z^3$ and $Z^4$ are each —N—

In one embodiment, $Z^1$ is —N— and $Z^2$, $Z^3$ and $Z^4$ are each —CH—.

In another embodiment, $Z^2$ is —N— and $Z^1$, $Z^3$ and $Z^4$ are each —CH—.

In still another embodiment, $Z^3$ is —N— and $Z^1$, $Z^2$ and $Z^4$ are each —CH—.

In another embodiment, $Z^4$ is —N— and $Z^1$, $Z^2$ and $Z^3$ are each —CH—.

In one embodiment, $Z^1$ is —N— and $Z^2$ is —C($R^5$)—.

In another embodiment, $Z^3$ is —N— and $Z^2$ is —C($R^5$)—.

In another embodiment, $Z^4$ is —N— and $Z^2$ is —C($R^5$)—.

In one embodiment, $Z^1$ is —N— and $Z^3$ is —C($R^6$)—.

In another embodiment, $Z^2$ is —N— and $Z^3$ is —C($R^6$)—.

In another embodiment, $Z^4$ is —N— and $Z^3$ is —C($R^6$)—.

In another embodiment, $R^4$ and $R^5$, or $R^5$ and $R^6$, or $R^6$ and $R^7$, together with the carbon atoms to which they are attached, combine to form a heterocycloalkyl or heteroaryl group.

In one embodiment, $R^1$ is bond.

In another embodiment, $R^1$ is —[C($R^{12}$)$_2$]$_r$—.

In another embodiment, $R^1$ is —[C($R^{12}$)$_2$]$_r$—O—[C($R^{12}$)$_2$]$_q$—.

In still another embodiment, $R^1$ is —[C($R^{12}$)$_2$]$_r$—N($R^9$)—[C($R^{12}$)$_2$]$_q$—.

In yet another embodiment, $R^1$ is —[C($R^{12}$)$_2$]$_q$—CH=CH—[C($R^{12}$)$_2$]$_q$—.

In another embodiment, $R^1$ is —[C($R^{12}$)$_2$]$_q$—C≡C—[C($R^{12}$)$_2$]$_q$—.

In a further embodiment, $R^1$ is —[C($R^{12}$)$_2$]$_q$—SO$_2$—[C($R^{12}$)$_2$]$_q$—.

In another embodiment, $R^1$ is —CH$_2$— or

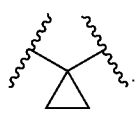 [SMILES: *C1(*)CC1]

In another embodiment, $R^1$ is —CH$_2$—.

In one embodiment, $R^{10}$ is —H and $R^1$ is other than a bond.

In another embodiment, $R^{10}$ is aryl.

In another embodiment, $R^{10}$ is cycloalkyl.

In another embodiment, $R^{10}$ is cycloalkenyl.

In still another embodiment, $R^{10}$ is heterocycloalkenyl.

In another embodiment, $R^{10}$ is heteroaryl.

In another embodiment, $R^{10}$ is heterocycloalkyl.

In another embodiment, $R^{10}$ is aryl or heteroaryl.

In another embodiment, —$R^{10}$ is:

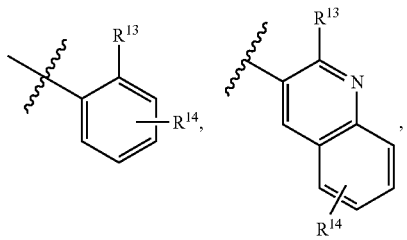

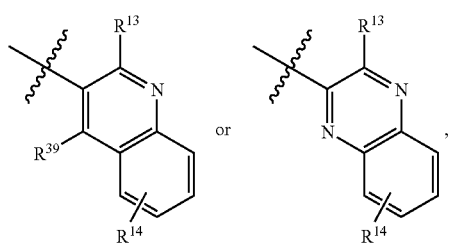

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, —$R^{10}$ is:

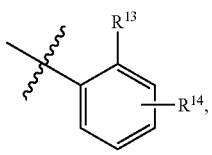

wherein $R^{13}$ is H or F, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In still another embodiment, $R^{10}$ is phenyl which can be optionally substituted as set forth in formula (I).

In another embodiment, $R^{10}$ is phenyl, which is substituted with from 1-4 groups independently selected from: halo, —NH$_2$, —NHSO$_2$-alkyl, haloalkyl, methoxy, —O-haloalkyl, -alkylene-NHC(O)NH-alkyl, alkyl, hydroxy, —CN, —C(O)NH$_2$ or -alkylene-NH$_2$.

In still another embodiment, $R^{10}$ is phenyl, which is substituted with from 1-4 F atoms.

In another embodiment, $R^{10}$ is phenyl, which is substituted with 2 F atoms.

In yet another embodiment, $R^{10}$ is phenyl, which is substituted with one F atoms.

In another embodiment, —R$^{10}$ is:

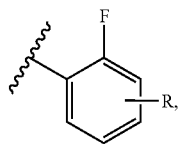

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In another embodiment, R$^{10}$ is:

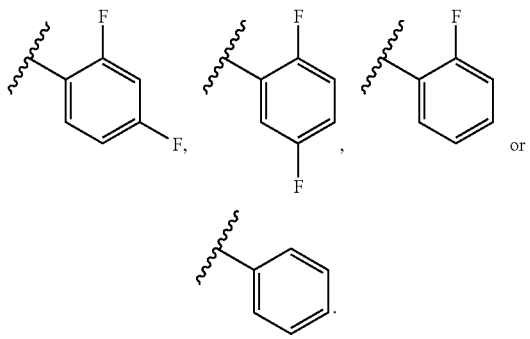

In another embodiment, R$^1$ is —CH$_2$— and —R$^{10}$ is:

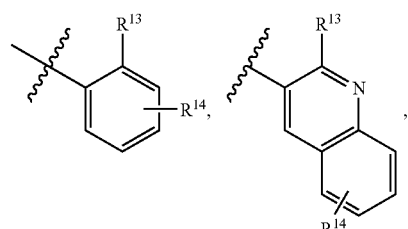

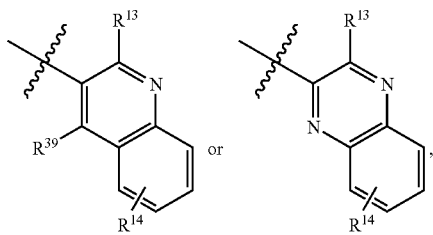

wherein R$^{13}$ is H or F and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, —R$^1$ is —CH$_2$— and R$^{10}$ is:

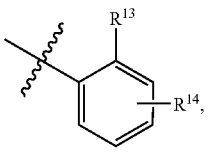

wherein R$^{13}$ is H or F and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In one embodiment, —R$^1$-R$^{10}$ is benzyl.

In another embodiment, —R$^1$-R$^{10}$ is benzyl, wherein the phenyl moiety of the benzyl group is substituted with from 1-4 groups independently selected from: halo, —NH$_2$, —NHSO$_2$-alkyl, haloalkyl, methoxy, —O-haloalkyl, -alkylene-NHC(O)NH-alkyl, alkyl, hydroxy, —CN, —C(O)NH$_2$ or -alkylene-NH$_2$.

In still another embodiment, —R$^1$-R$^{10}$ is

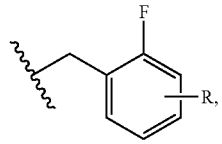

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In still another embodiment, —R$^1$-R$^{10}$ is alkyl.

In yet another embodiment, —R$^1$-R$^{10}$ is benzyl, wherein the phenyl moiety of the benzyl group is substituted with 1 or 2 fluorine atoms.

In yet another embodiment, —R$^1$-R$^{10}$ is benzyl, wherein the phenyl moiety of the benzyl group is substituted with 1 or 2 methyl groups.

In another embodiment, —R$^1$ is —CH$_2$— and R$^{10}$ is:

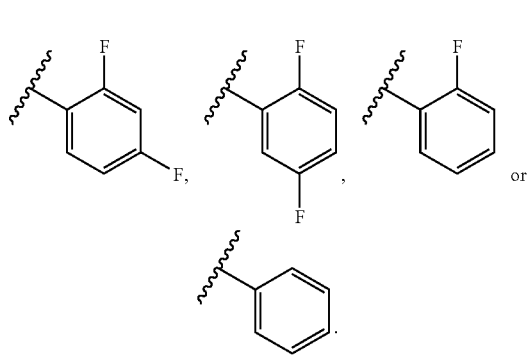

In a further embodiment, —R$^1$-R$^{10}$ is —CH$_2$-cycloalkyl.
In one embodiment, R$^2$ is —C(O)R$^9$.
In another embodiment, R$^2$ is —C(O)OR$^9$.

In another embodiment, R² is —C(O)OCH₂OR⁹.
In still another embodiment, R² is —C(O)N(R⁹)₂.
In yet another embodiment, R² is —[C(R¹²)₂]_q—C(O)OR⁹.
In another embodiment, R² is —[C(R¹²)₂]_q—C(O)N(R⁹)₂.
In a further embodiment, R² is -alkyl.
In another embodiment, R² is —[C(R¹²)₂]_q-aryl.
In another embodiment, R² is —[C(R¹²)₂]_q-cycloalkyl.
In still another embodiment, R² is —[C(R¹²)₂]_q-cycloalkenyl.
In still another embodiment, R² is —[C(R¹²)₂]_q-heterocycloalkyl.
In yet another embodiment, R² is —[C(R¹²)₂]_q-heteroaryl.
In another embodiment, R² is —[C(R¹²)₂]_q-heterocycloalkenyl.
In a further embodiment, R² is —C(O)OR⁹ or —C(O)N(R⁹)₂.
In another embodiment, R² is —C(O)OH, —C(O)NH₂, —C(O)O-alkyl, —C(O)O-cycloalkyl, —C(O)NH-alkyl or C(O)NH-cycloalkyl.
In another embodiment, R² is —C(O)OH.
In another embodiment, R² is —C(O)O-alkyl.
In still another embodiment, R² is —C(O)OCH₃.
In another embodiment, R² is —C(O)NH₂.
In still another embodiment, R² is —C(O)R⁹, —C(O)OR⁹, —C(O)OCH₂OR⁹, —C(O)N(R⁹)₂, —[C(R¹²)₂]_qC(O)OR⁹, —[C(R¹²)₂]_q—C(O)N(R⁹)₂ or —[C(R¹²)₂]_q-heteroaryl wherein a heteroaryl group can be optionally substituted with up to 4 substituents, which are the same or different, and are selected from alkyl, alkenyl, alkynyl, aryl, —[C(R¹²)₂]_q-cycloalkyl, —[C(R¹²)₂]_q-cycloalkenyl, —[C(R¹²)₂]_q-heterocycloalkyl, —[C(R¹²)₂]_q-heterocycloalkenyl, —[C(R¹²)₂]_q-heteroaryl, —[C(R¹²)₂]_q-haloalkyl, —[C(R¹²)₂]_q-hydroxyalkyl, halo, hydroxy, —OR⁹, —CN, —[C(R¹²)₂]_qC(O)R⁸, —[C(R¹²)₂]_q—C(O)OR⁹, —[C(R¹²)₂]_q—C(O)N(R⁹)₂, —[C(R¹²)₂]_q—OR⁹, —[C(R¹²)₂]_q—N(R⁹)₂, —[C(R¹²)₂]_q—NHC(O)R⁸, —[C(R¹²)₂]_q—NR⁸C(O)N(R⁹)₂, —[C(R¹²)₂]_q—NHSO₂R¹¹, —[C(R¹²)₂]_q—S(O)_pR¹¹, —[C(R¹²)₂]_q—SO₂N(R⁹)₂ and —SO₂N(R⁹)C(O)N(R⁹)₂.

In another embodiment, R³ is

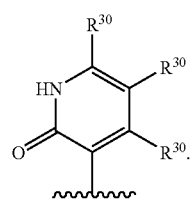

In another embodiment, R³ is
In another embodiment, R³ is

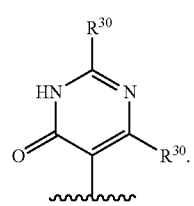

In still another embodiment, R³ is

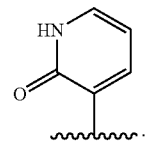

In another embodiment, R³ is

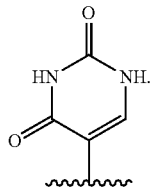 [SMILES: *c1c[nH]c(=O)[nH]c1=O]

In one embodiment, R² is —C(O)OR⁹ or —C(O)N(R⁹)₂, and R³ is

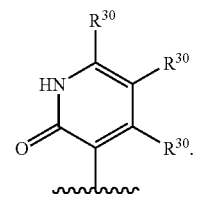

In another embodiment, R² is —C(O)OH or —C(O)O-alkyl; and R³ is

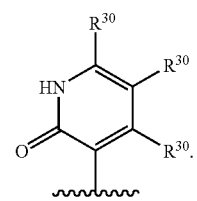

In one embodiment, R² is —C(O)OR⁹ or —C(O)N(R)₂, and R³ is

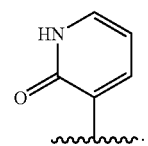 [SMILES: *c1ccc[nH]c1=O]

In another embodiment, R² is —C(O)OH or —C(O)O-alkyl; and R³ is

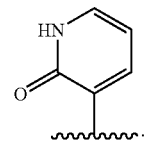

In one embodiment, $R^1$ is —CH$_2$—, —CH$_2$CH$_2$— or —CH(CH$_3$)—, and $R^2$ is —C(O)OR$^9$ or —C(O)N(R$^9$)$_2$.

In one embodiment, $R^1$ is —CH$_2$— and $R^2$ is —C(O)OR$^9$ or —C(O)N(R$^9$)$_2$.

In another embodiment, $R^{11}$ is —CH$_2$— and $R^2$ is —C(O)OH or —C(O)O-alkyl.

In one embodiment, one of $Z^1$, $Z^2$, $Z^3$ and $Z^4$ is —N— and the others are not —N— or —N(O)—; and $R^{10}$ is

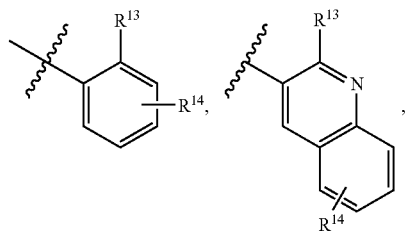

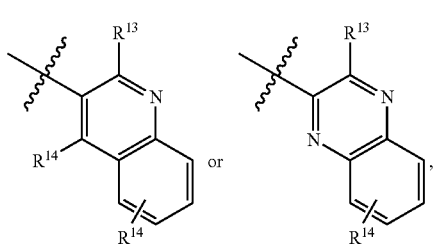

wherein $R^{13}$ is H, F, Br or Cl, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In one embodiment, one of $Z^1$, $Z^2$, $Z^3$ and $Z^4$ is —N— and the others are not —N— or —N(O)—; $R^3$ is

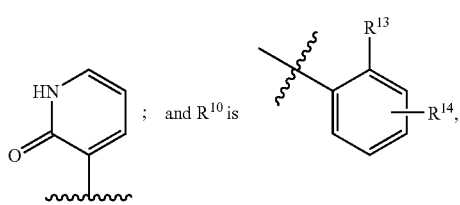

wherein $R^{13}$ is H, F, Br or Cl, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In one embodiment, one of $Z^1$, $Z^2$, $Z^3$ and $Z^4$ is —N— and the others are not —N— or —N(O)—; $R^3$ is

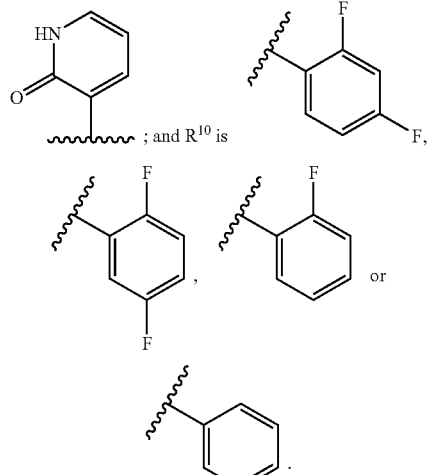

In one embodiment, one of $Z^1$, $Z^2$, $Z^3$ and $Z^4$ is —N— and the others are not —N— or —N(O)—; $R^2$ is —C(O)OH or —C(O)O-alkyl; $R^3$ is

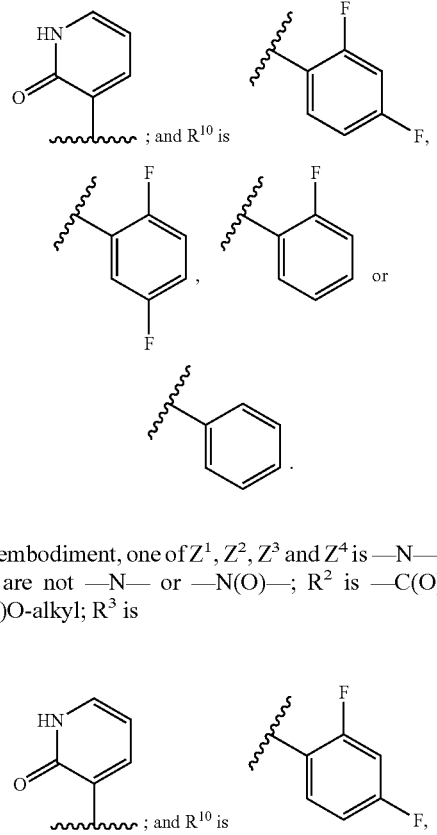

In one embodiment, $R^1$ is —CH$_2$—, —CH$_2$CH$_2$— or —CH(CH$_3$)—; $R^2$ is —C(O)OR$^9$ or —C(O)N(R$^9$)$_2$; and $R^{10}$ is

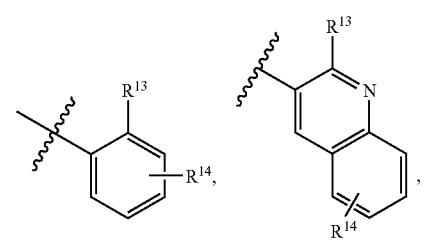

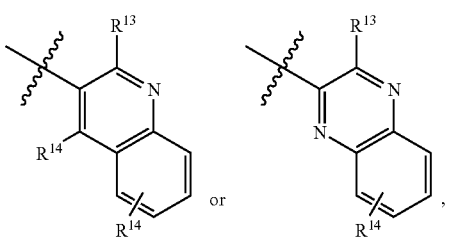

wherein R¹³ is H, F, Br or Cl, and R¹⁴ represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, hydroxy, —NH₂, —SO₂ alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl.

In another embodiment, R¹ is —CH₂—, —CH₂CH₂— or —CH(CH₃)—; R² is —C(O)OR⁹ or —C(O)N(R⁹)₂; and R¹⁰ is

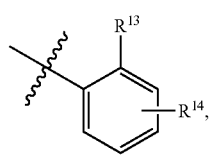

wherein R¹³ is H, F, Br or Cl, and R¹⁴ represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, hydroxy, —NH₂, —SO₂ alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl.

In another embodiment, R¹ is —CH₂—, —CH₂CH₂— or —CH(CH₃)—; R² is —C(O)OR⁹ or —C(O)N(R⁹)₂; and R¹⁰ is

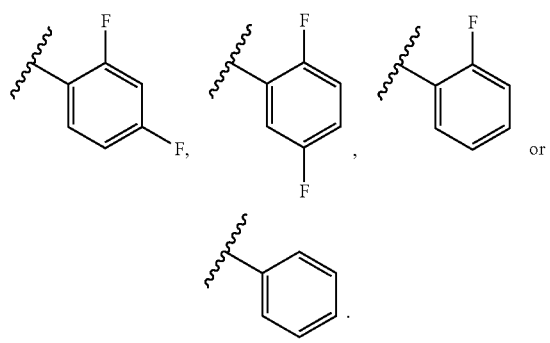

In one embodiment, R² is —C(O)OR⁹ or —C(O)N(R⁹)₂; and R¹⁰ is

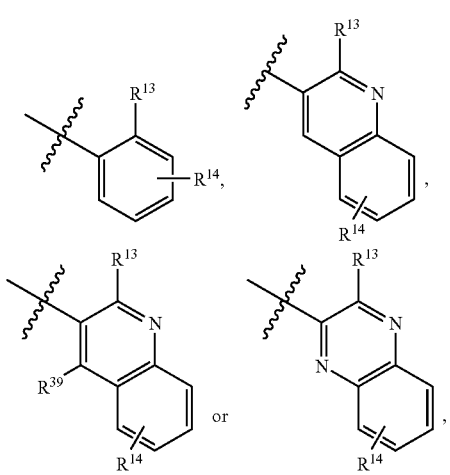

wherein R¹³ is H or F and R¹⁴ represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, hydroxy, —NH₂, —SO₂ alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl.

In another embodiment, R² is —C(O)OR⁹ or —C(O)N(R⁹)₂; and R¹⁰ is

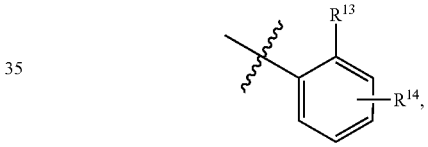

wherein R¹³ is H or F and R¹⁴ represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, hydroxy, —NH₂, —SO₂ alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl.

In another embodiment, R² is —C(O)OR⁹ or —C(O)N(R⁹)₂; and R¹⁰ is

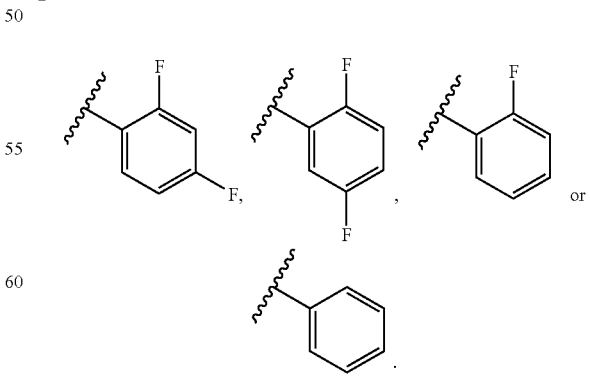

In one embodiment, R¹ is —CH₂—; R² is —C(O)OR⁹ or —C(O)N(R⁹)₂; and R¹⁰ is

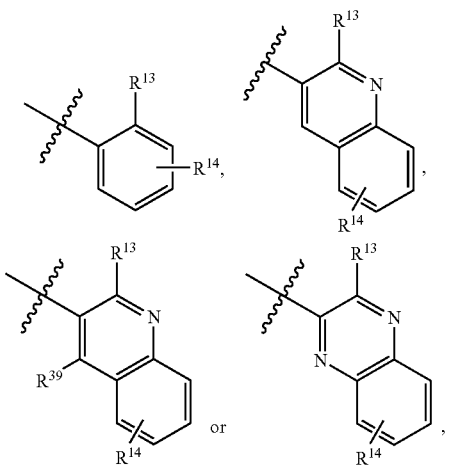

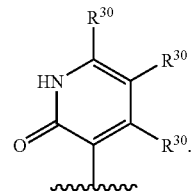

In another embodiment, $R^1$ is —CH$_2$—; —C(O)OH or —C(O)O-alkyl; and $R^3$ is

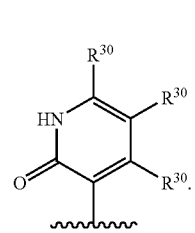

In one embodiment, $R^1$ is —CH$_2$—; $R^{10}$ is wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, $R^1$ is —CH$_2$—; $R^2$ is —C(O)OR$^9$ or —C(O)N(R$^9$)$_2$; and $R^{10}$ is

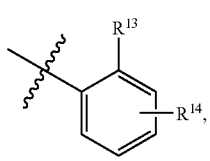

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, $R^1$ is —CH$_2$—; $R^2$ is —C(O)OR$^9$ or —C(O)N(R$^9$)$_2$; and $R^{10}$ is

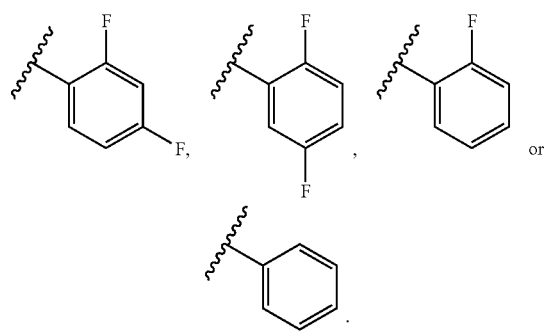

In one embodiment, $R^1$ is —CH$_2$—; $R^2$ is —C(O)OR$^9$ or —C(O)N(R$^g$)$_2$; and $R^3$ is

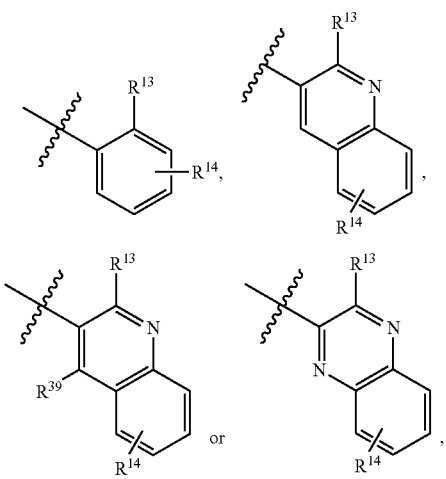

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; $R^2$ is —C(O)OR$^9$ or —C(O)N(R$^9$)$_2$; and $R^3$ is

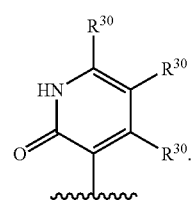

In another embodiment, $R^1$ is —CH$_2$—; $R^{10}$ is

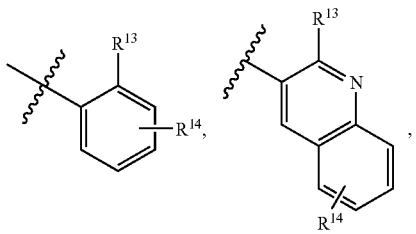

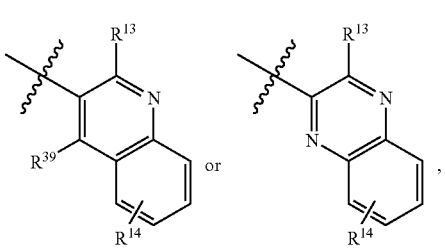

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; $R^2$ is —C(O)OH or —C(O)O-alkyl; and $R^3$ is

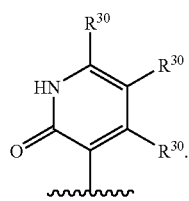

In one embodiment, $R^1$ is —CH$_2$—; $R^{10}$ is phenyl, which can be optionally substituted as set forth in formula (I); $R^2$ is —C(O)OR$^9$ or —C(O)N(R$^9$)$_2$; and $R^3$ is

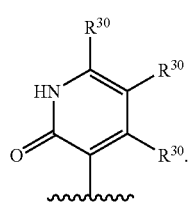

In another embodiment, $R^1$ is —CH$_2$—; $R^{10}$ is phenyl, which can be optionally substituted as set forth in formula (I); $R^2$ is —C(O)OH or —C(O)O-alkyl; and $R^3$ is

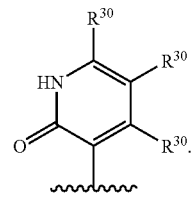

In one embodiment, $R^1$ is —CH$_2$—; $R^{10}$ is

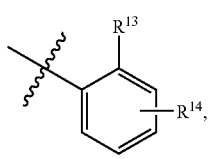

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; $R^2$ is —C(O)OR$^9$ or —C(O)N(R$^9$)$_2$; and $R^3$ is

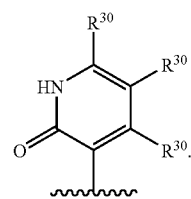

In another embodiment, $R^1$ is —CH$_2$—; $R^{10}$ is

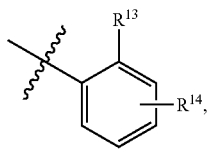

wherein $R^{13}$ is H or F and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; $R^2$ is —C(O)OH or —C(O)O-alkyl; and $R^3$ is

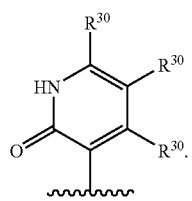

In one embodiment, $R^1$ is —$CH_2$—; $R^{10}$ is phenyl, which can be optionally substituted with one or two F atoms; $R^2$ is —C(O)$OR^9$ or —C(O)N($R^9$)$_2$; and $R^3$ is

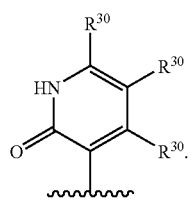

In another embodiment, $R^1$ is —$CH_2$—; $R^{10}$ is phenyl, which can be optionally substituted with one or two F atoms; $R^2$ is —C(O)OH or —C(O)O-alkyl; and $R^3$ is

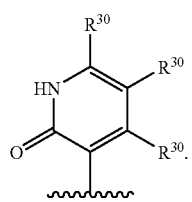

In one embodiment, $R^1$ is —$CH_2$—; $R^2$ is —C(O)$OR^9$ or —C(O)N($R^9$)$_2$; one of $Z^1$, $Z^2$, $Z^3$ and $Z^4$ is —N— and the others are not —N— or —N(O)—; and $R^{10}$ is

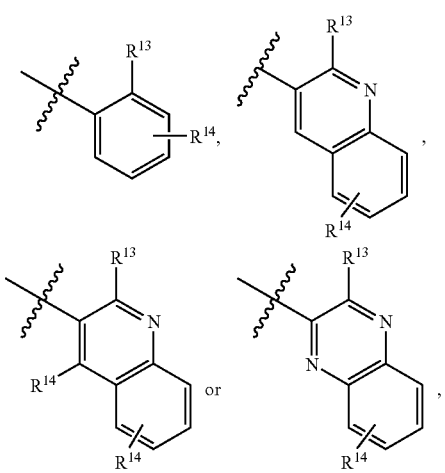

wherein $R^{13}$ is H or F, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In another embodiment, $R^1$ is —$CH_2$—; $R^2$ is —C(O)$OR^9$ or —C(O)N($R^9$)$_2$; $R^3$ is

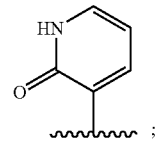 [SMILES: *c1ccc[nH]c1=O]

one of $Z^1$, $Z^2$, $Z^3$ and $Z^4$ is —N— and the others are not —N— or —N(O)—; and $R^{10}$ is

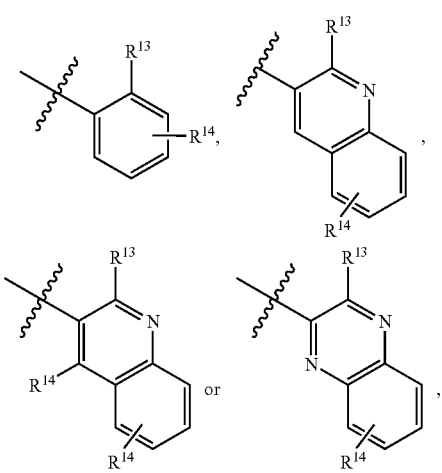

wherein $R^{13}$ is H or F, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In another embodiment, $R^1$ is —$CH_2$—; $R^2$ is —C(O)$OR^9$ or —C(O)N($R^9$)$_2$; $R^3$ is

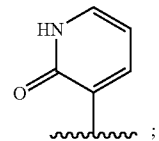 [SMILES: *c1ccc[nH]c1=O]

one of $Z^1$, $Z^2$, $Z^3$ and $Z^4$ is —N— and the others are not —N— or —N(O)—; and $R^{10}$ is

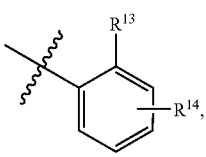

wherein $R^{13}$ is H or F, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —NH$_2$, —SO$_2$ alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In still another embodiment, R$^1$ is —CH$_2$—; R$^2$ is —C(O)OR$^9$ or —C(O)N(R$^9$)$_2$; R$^3$ is

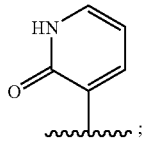 [SMILES: *c1ccc[nH]c1=O]

one of Z$^1$, Z$^2$, Z$^3$ and Z$^4$ is —N— and the others are not —N— or —N(O)—; and R$^{10}$ is

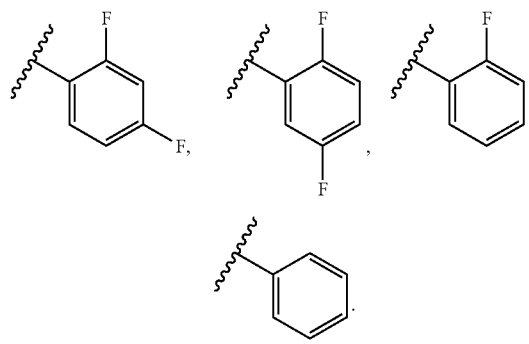

In yet another embodiment, R$^1$ is —CH$_2$—; R$^2$ is —C(O)OH or —C(O)O-alkyl; R$^3$ is

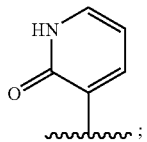 [SMILES: *c1ccc[nH]c1=O]

one of Z$^1$, Z$^2$, Z$^3$ and Z$^4$ is —N— and the others are not —N— or —N(O)—; and R$^{10}$ is

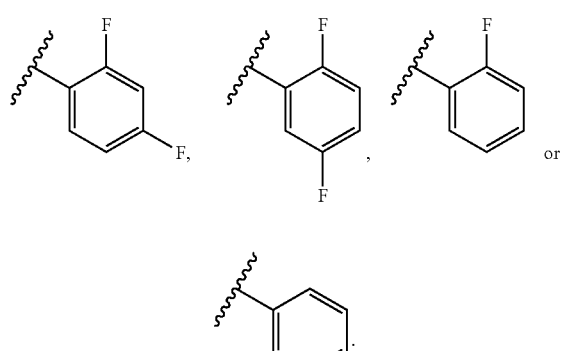

In one embodiment, the compounds of formula (II) have the formula (IIa):

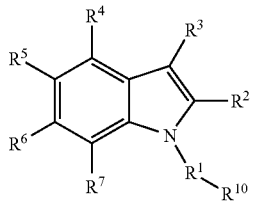

(IIa)

wherein:

Z$^1$ is —N—, —N(O)— or —C(R$^4$)—;
Z$^2$ is —N—, —N(O)— or —C(R$^5$)—;
Z$^3$ is —N—, —N(O)— or —C(R$^6$)—;
Z$^4$ is —N—, —N(O)— or —C(R$^7$)—, such that one of Z$^1$, Z$^2$, Z$^3$ and Z$^4$ is —N— or —N(O)— and the others are not —N— or —N(O)—;

R$^1$ is —CH$_2$—, —CH$_2$CH$_2$—, —CH(CH$_3$)— or

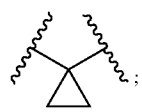 [SMILES: *C1(*)CC1]

R$^2$ is —C(O)OR$^9$ or —C(O)N(R$^9$)$_2$, wherein R$^9$ is H, alkyl, aryl, cycloalkyl, heteroaryl or heterocycloalkyl;

R$^3$ is:

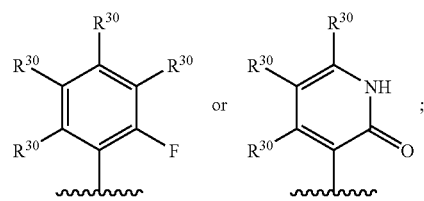

R$^4$, R$^5$, R$^6$ and R$^7$ are each, independently, H, alkyl, cycloalkyl, heterocycloalkyl, haloalkyl, halo, hydroxy, —OH, —O-alkyl, —O-haloalkyl, —NH$_2$, —NH-alkyl or —N(alkyl)$_2$;

each occurrence of R$^9$ is independently H, alkyl, cycloalkyl, heterocycloalkyl, haloalkyl or hydroxyalkyl;

R$^{10}$ is:

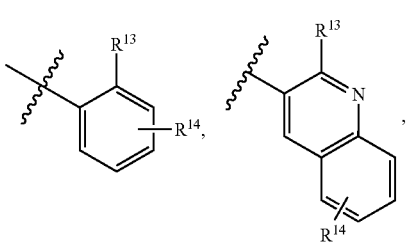

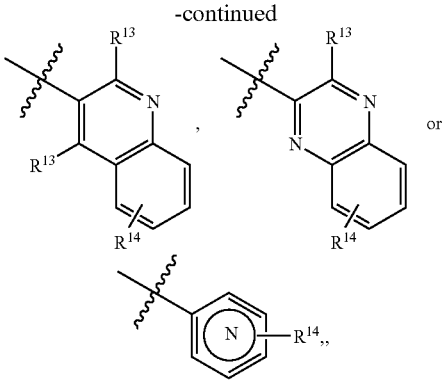

such that when $R^1$ is a bond, $R^{10}$ is not H;

each occurrence of $R^{11}$ is independently alkyl, aryl, cycloalkyl, haloalkyl, heteroaryl, heterocycloalkyl or hydroxyalkyl;

$R^{13}$ is H, F, Br or Cl;

$R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —$C(O)NH_2$, —C(O)NH-alkyl, —C(O)OH, hydroxy, —$NH_2$, —$SO_2$ alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl;

each occurrence of $R^{30}$ is independently, H, halo, —$N(alkyl)_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group;

each occurrence of q is independently an integer ranging from 0 to 4;

each occurrence of r is independently an integer ranging from 1 to 4; and

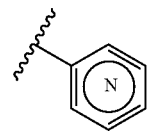

represents a pyridyl group, wherein the ring nitrogen atom can be at any of the five unsubstituted ring atom positions.

In one embodiment, the compounds of formula (II) are in purified form.

Non-limiting examples of compounds of formula (II) include the following compounds:

| Cmpd No. | Structure | MS (M + H) |
|---|---|---|
| 6 | 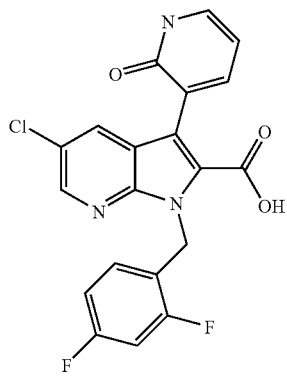 [SMILES: O=C(O)c1c(-c2ccc[nH]c2=O)c2cc(Cl)cnc2n1Cc1ccc(F)cc1F] | 416.8 |
| 7 | 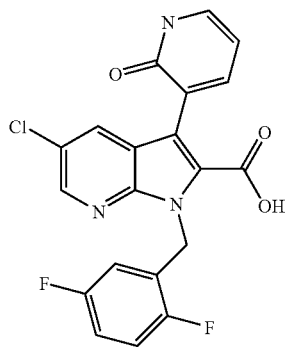 [SMILES: O=C(O)c1c(-c2ccc[nH]c2=O)c2cc(Cl)cnc2n1Cc1cc(F)ccc1F] | 416.8 |

-continued
| Cmpd No. | Structure | MS (M + H) |
|---|---|---|
| 8 | 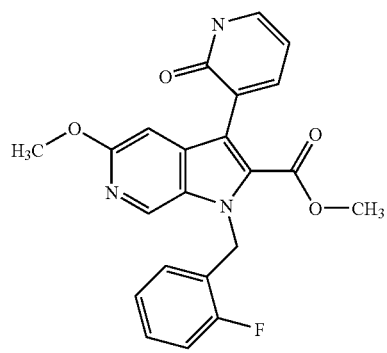 | 408.4 |
| 9 | 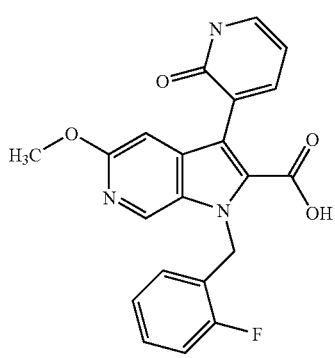 [SMILES: COc1cc2c(-c3ccc[nH]c3=O)c(C(=O)O)n(Cc3ccccc3F)c2cn1] | 394.4 |
| 10 | 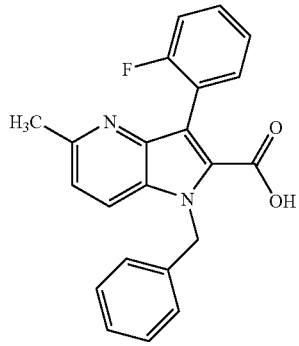 [SMILES: Cc1ccc2c(n1)c(-c1ccccc1F)c(C(=O)O)n2Cc1ccccc1] | 361.4 |
| 11 | 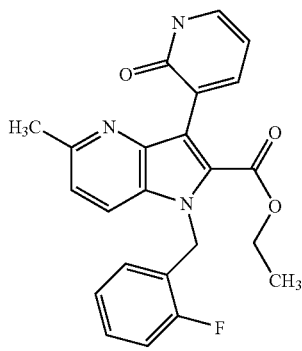 [SMILES: CCOC(=O)c1c(-c2ccc[nH]c2=O)c2nc(C)ccc2n1Cc1ccccc1F] | 406.4 |

-continued
| Cmpd No. | Structure | MS (M + H) |
|---|---|---|
| 12 | 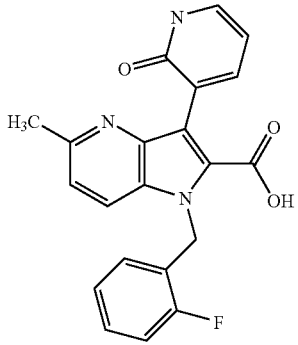 [SMILES: Cc1ccc2c(n1)c(-c1ccc[nH]c1=O)c(C(=O)O)n2Cc1ccccc1F] | 378.4 |
| 19 | 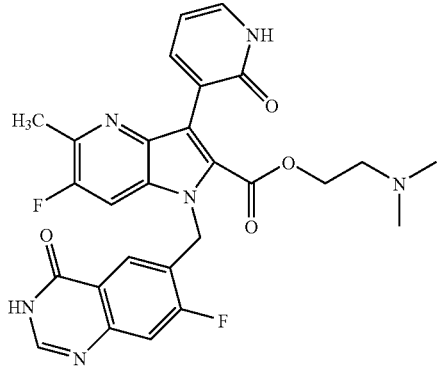 [SMILES: Cc1nc2c(-c3ccc[nH]c3=O)c(C(=O)OCCN(C)C)n(Cc3cc4c(=O)[nH]cnc4cc3F)c2cc1F] | NA |
| 20 | 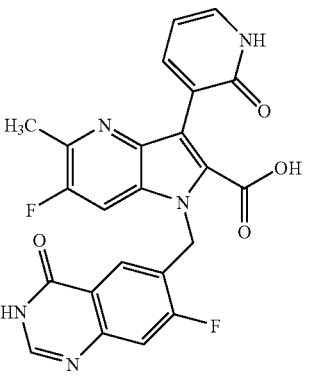 [SMILES: Cc1nc2c(-c3ccc[nH]c3=O)c(C(=O)O)n(Cc3cc4c(=O)[nH]cnc4cc3F)c2cc1F] | NA |
| 21 | 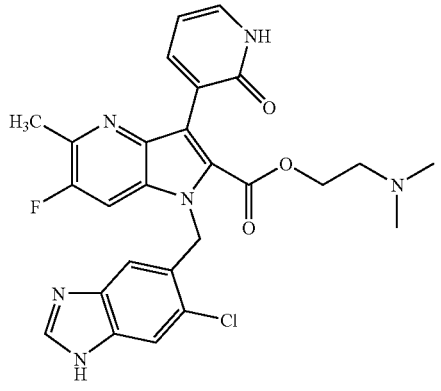 | NA |

-continued

| Cmpd No. | Structure | MS (M + H) |
|---|---|---|
| 22 | 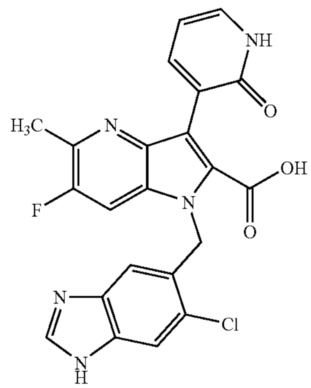 [SMILES: Cc1nc2c(-c3ccc[nH]c3=O)c(C(=O)O)n(Cc3cc4nc[nH]c4cc3Cl)c2cc1F] | NA |
| 23 | 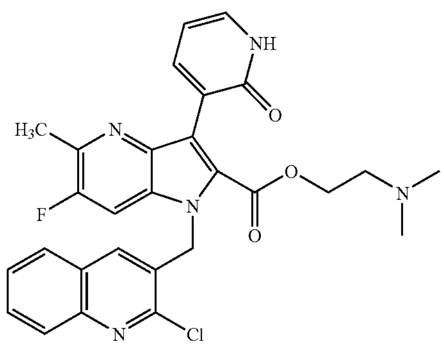 [SMILES: Cc1nc2c(-c3ccc[nH]c3=O)c(C(=O)OCCN(C)C)n(Cc3cc4ccccc4nc3Cl)c2cc1F] | NA |
| 24 | 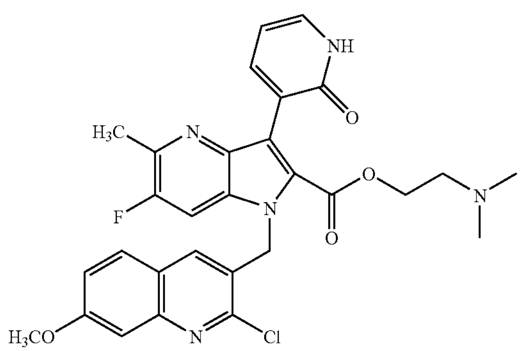 [SMILES: COc1ccc2cc(Cn3c(C(=O)OCCN(C)C)c(-c4ccc[nH]c4=O)c4nc(C)c(F)cc43)c(Cl)nc2c1] | NA |
| 25 | 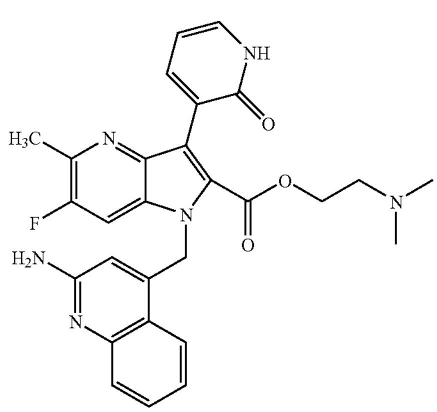 | NA |

-continued
| Cmpd No. | Structure | MS (M + H) |
|---|---|---|
| 26 | 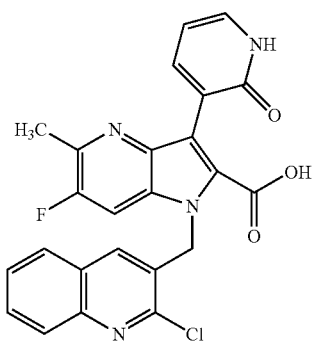 [SMILES: Cc1nc2c(-c3ccc[nH]c3=O)c(C(=O)O)n(Cc3cc4ccccc4nc3Cl)c2cc1F] | NA |
| 27 | 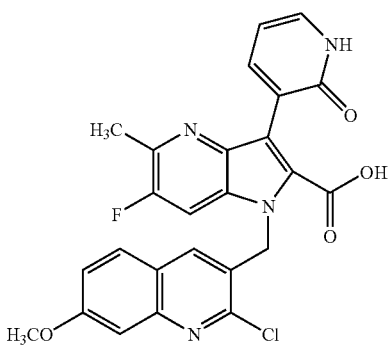 [SMILES: COc1ccc2cc(Cn3c(C(=O)O)c(-c4ccc[nH]c4=O)c4nc(C)c(F)cc43)c(Cl)nc2c1] | NA |
| 28 | 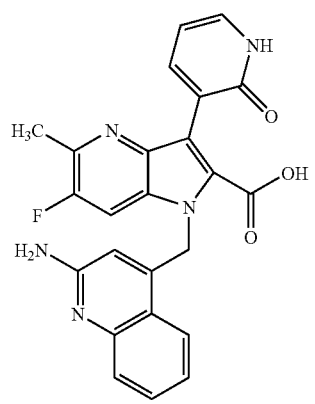 [SMILES: Cc1nc2c(-c3ccc[nH]c3=O)c(C(=O)O)n(Cc3cc(N)nc4ccccc34)c2cc1F] | NA |
| 29 | 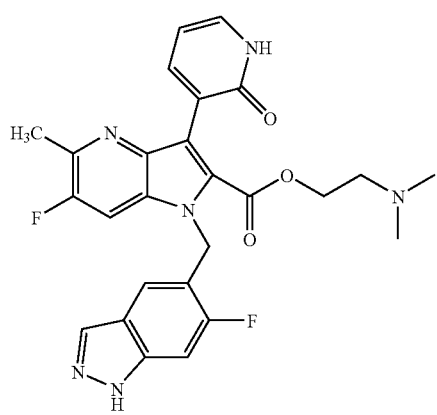 | NA |

| Cmpd No. | Structure | MS (M + H) |
|---|---|---|
| 30 | 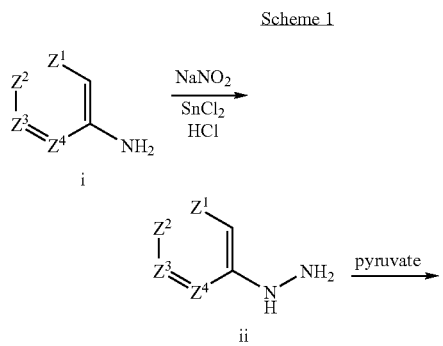 | NA |

NA = not available and pharmaceutically acceptable salts, solvates, esters and prodrugs thereof.

Methods for Making the 2-Substituted Aza-Indole Derivatives

Methods useful for making the 2,3-Substituted Azaindole Derivatives are set forth in the Examples below and generalized in Schemes 1-7. Examples of commonly known methodologies useful for the synthesis of indoles are set forth, for example, in G. R. Humphrey and J. T. Kuethe, *Chemical Reviews* 106:2875-2911, 2006.

Scheme 1 shows one method for preparing compounds of formula iv, which are useful intermediates for making of the 2,3-Substituted Azaindole Derivatives.

Scheme 1

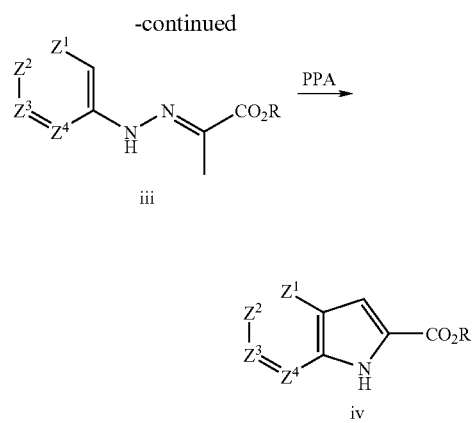

wherein $Z^1$, $Z^2$, $Z^3$, and $Z^4$ are defined above for the 2,3-Substituted Azaindole Derivatives, and R is H, alkyl or aryl.

An aniline compound of formula i can be converted to an indole compound of formula iv using various indole syntheses that are well-known to those skilled in the art of organic synthesis, including but not limited to, a Fischer indole synthesis through intermediates of type ii and iii, the method set forth in Nazare et al., *Angew. Chem.*, 116:4626-4629 (2004).

Scheme 2 shows methods useful for making compounds viii and x, which are useful intermediates for making of the 2,3-Substituted Azaindole Derivatives.

Scheme 2

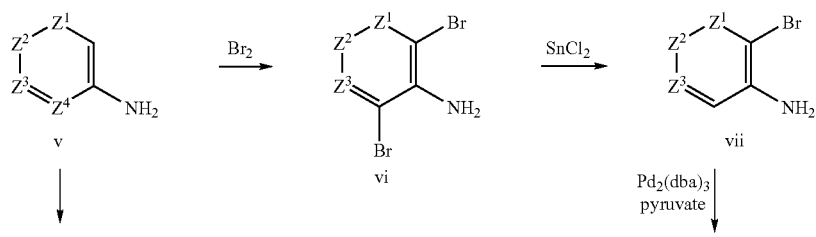

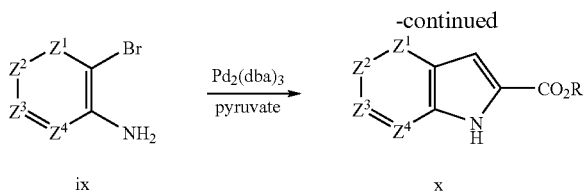
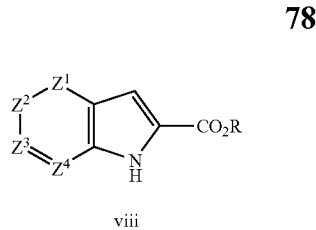

wherein $Z^1$, $Z^2$, $Z^3$, and $Z^4$ are defined above for the 2,3-Substituted Azaindole Derivatives, and R is H, alkyl or aryl.

A benzene derivative of formula v, wherein $Z^4$ is —CH—, can be di-brominated to provide compound vi. Selective de-bromination provides the corresponding monobromo analog vii, which under palladium catalyzed cyclization conditions provides the desired intermediate viii, wherein $R^7$ is H. Alternatively a compound of formula v, wherein $R^7$ is other than H, can be monobrominated to provide compound 1x. Compound 1x can then undergo under palladium catalyzed cyclization conditions provides the desired intermediate x, wherein $R^7$ is other than H.

Scheme 3 illustrates methods by which intermediate compounds of formula xi (which corresponds to the compounds of formulas viii and x) can be further derivatized to provide the 2,3-Substituted Azaindole Derivatives, wherein $R^2$ is —C(O)OH.

Scheme 3

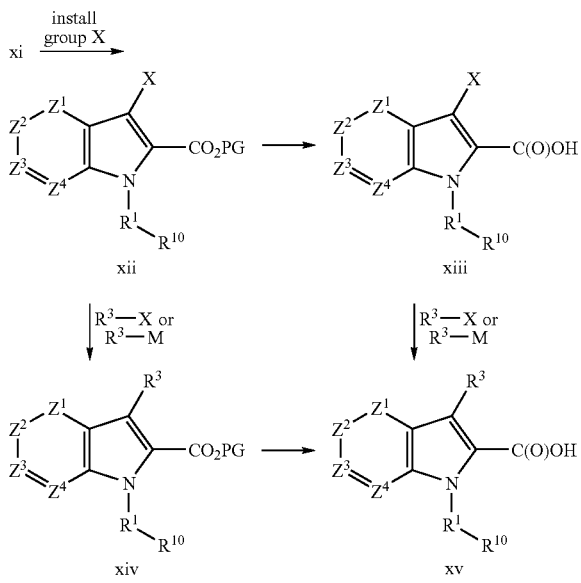

wherein $Z^1$, $Z^2$, $Z^3$, $Z^4$, $R^1$, $R^3$ and $R^{10}$ are defined above for the 2,3-Substituted Azaindole Derivatives; PG is a carboxy protecting group; and X is halo, —O-triflate, —B(OH)$_2$, —Si(alkyl)$_2$OH, —Sn(alkyl)$_3$, —MgBr, —MgCl, —ZnBr, or —ZnCl; and M is any metal which can participate in an organometallic cross-coupling reaction.

An intermediate compound of formula xi can be converted to a 3-substituted indole of formula xv using methods well-known to one skilled in the art of organic synthesis. A compound of formula xii, wherein X is halo or —O-triflate can then be coupled with an appropriate compound of formula $R^3$-M (wherein M is —B(OH)$_2$, —Si(alkyl)$_2$OH, —Sn(alkyl)$_3$, —MgBr, —MgC, —ZnBr, —ZnCl, or any metal which can participate in an organometallic cross-coupling reaction) using an organometallic cross-coupling method. Alternatively, a compound of formula xii, wherein X is —B(OH)$_2$, —Si(alkyl)$_2$OH, —Sn(alkyl)$_3$, —MgBr, —MgCl, —ZnBr, —ZnCl, or any metal which can participate in an organometallic cross-coupling reaction, can then be coupled with an appropriate compound of formula $R^3$-M (wherein M is halo or —O-triflate) using an organometallic cross-coupling method. Suitable cross-coupling methods include, but not limited to, a Stille coupling (see Choshi et al., *J. Org. Chem.*, 62:2535-2543 (1997), and Scott et al., *J. Am. Chem. Soc.*, 106:4630 (1984)), a Suzuki coupling (see Miyaura et al., *Chem. Rev.*, 95:2457 (1995)), a Negishi coupling (see Zhou et al., *J. Am. Chem. Soc.*, 127:12537-12530 (2003)), a silanoate-based coupling (see Denmark et al., *Chem. Eur. J.* 12:4954-4963 (2006)) and a Kumada coupling (see Kumada, *Pure Appl. Chem.*, 52:669 (1980) and Fu et al., *Angew. Chem.* 114:4363 (2002)) to provide a compound of formula xiv. The carboxy protecting group, PG, can then be removed from the compound of formula xiv and the resulting carboxylic acid can be derivatized using the methods described below in order to make the appropriate $R^2$ groups and make the compounds of formula xv, which correspond to the compounds of formula (I), wherein $R^2$ is —C(O)OH. Alternatively, a compound of formula xii can first be deprotected and the $R^2$ group attached using the above methods to provide a compound of formula xiii. A compound of formula xiii can then be cross-coupled with a compound of $R^3$—X or $R^3$-M as described above to provide make the compounds of formula xv.

Scheme 4 shows a method useful for making the 2,3-Substituted Azaindole Derivatives, wherein $R^2$ is —C(O)N($R^9$)S$_2R^{11}$.

Scheme 4

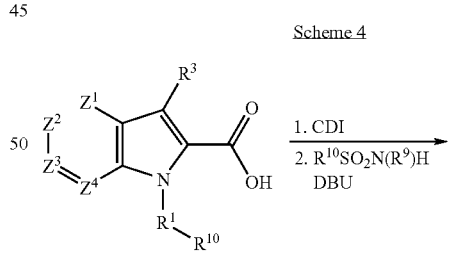

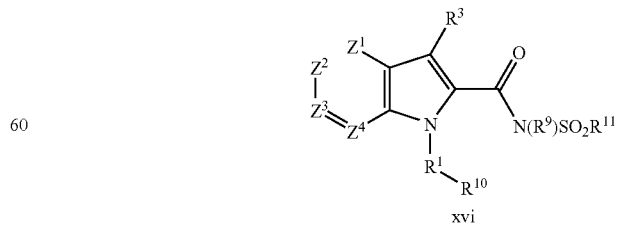

wherein $Z^1$, $Z^2$, $Z^3$, $Z^4$, $R^1$, $R^3$, $R^9$, $R^{10}$ and $R^{11}$ are defined above for the 2,3-Substituted Azaindole Derivatives.

A 2-carboxy indole compound of formula xv can be coupled with a compound of formula $R^{11}SO_2NH(R^9)$ in the presence of carbonyldiimidazole (CDI) and 1,8-diazabicyclo[5.4.0]undec-7-ene (DBU) to provide the compounds of formula xvi, which correspond to the 2,3-Substituted Azaindole Derivatives wherein $R^2$ is $-C(O)NHSO_2R^{11}$.

Scheme 5 shows a method useful for making the 2,3-Substituted Azaindole Derivatives, wherein $R^2$ is $-C(O)N(R^9)_2$.

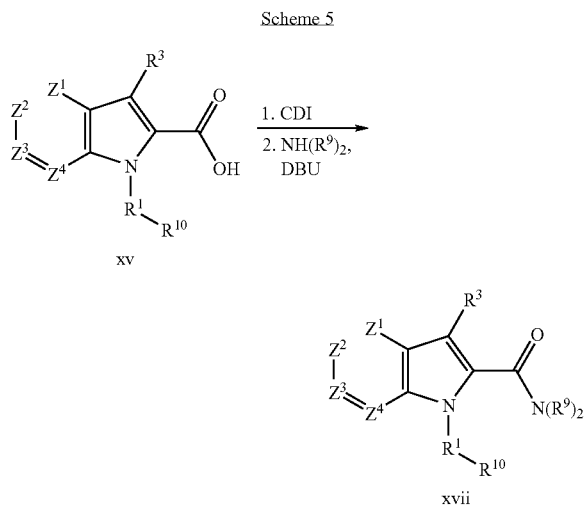

wherein $Z^1$, $Z^2$, $Z^3$, $Z^4$, $R^1$, $R^3$, $R^9$ and $R^{10}$ are defined above for the 2,3-Substituted Azaindole Derivatives.

A 2-carboxy indole compound of formula xv can be coupled with an amine of formula $NH(R^9)_2$ in the presence of carbonyldiimidazole (CDI) and 1,8-diazabicyclo[5.4.0]undec-7-ene (DBU) to provide the compounds of formula xvii, which correspond to the 2,3-Substituted Azaindole Derivatives wherein $R^2$ is $-C(O)N(R^9)_2$.

Scheme 6 shows a method useful for making the 2,3-Substituted Azaindole Derivatives, wherein $R^2$ is:

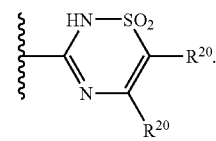

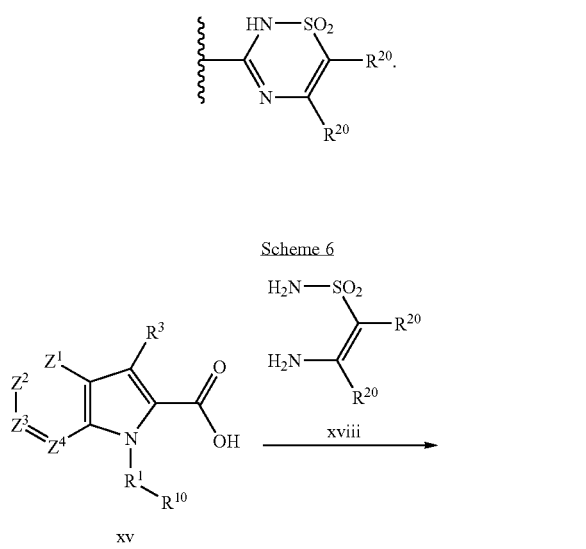

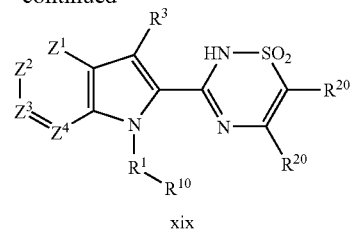

wherein $Z^1$, $Z^2$, $Z^3$, $Z^4$, $R^1$, $R^3$, $R^{10}$ and $R^{20}$ are defined above for the 2,3-Substituted Azaindole Derivatives.

A 2-carboxy indole compound of formula xv can be reacted with a 2-amino sulfonamide of formula xviii to provide the compounds of formula xix, which correspond to the 2,3-Substituted Azaindole Derivatives wherein $R^2$ is:

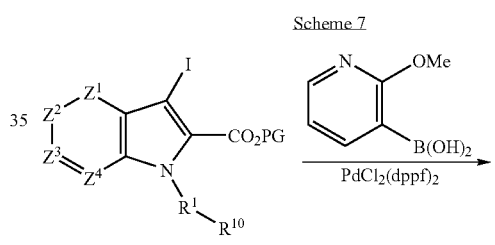

Scheme 7 shows a method useful for making the 2,3-Substituted Azaindole Derivatives, wherein $R^3$ is 1H-pyridin-2-one-3-yl.

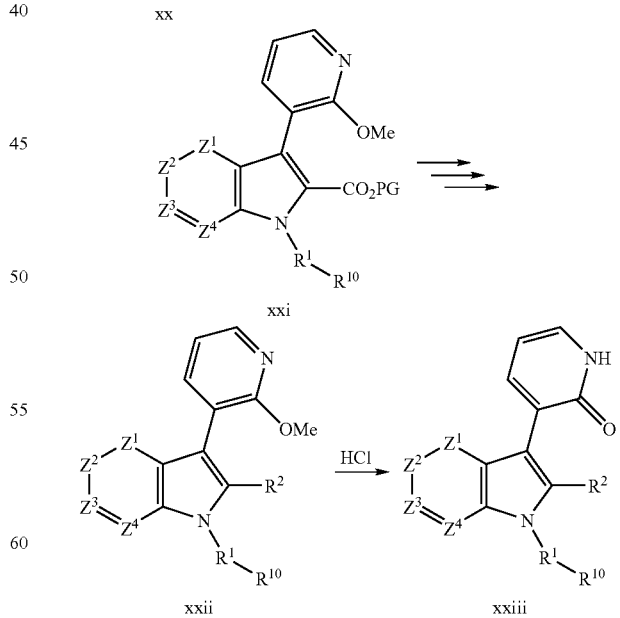

wherein $Z^1$, $Z^2$, $Z^3$, $Z^4$, $R^1$, $R^2$, $R^{10}$ and $R^{20}$ are defined above for the 2,3-Substituted Azaindole Derivatives and PG is a carboxy protecting group.

A 3-iodoindole compound of formula xx can be coupled with 2-hydroxypyridine-3-boronic acid using a Suzuki coupling reaction to provide the $R^3$-substituted indole compounds of formula xxi. A compound of formula xxi can be further elaborated using methods set forth above to provide the compounds of formula xxii. The 2-hydroxypyridyl moiety of a compound of formula xxii can then be reacted with strong acid, such as hydrochloric acid to provide a compound of formula xxiii, which correspond to the 2,3-Substituted Azaindole Derivatives, wherein $R^3$ is 1H-pyridin-2-one-3-yl.

The starting material and reagents depicted in Schemes 1-7 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of 2,3-Substituted Azaindole Derivatives may require the need for the protection of certain functional groups (i.e., derivatization for the purpose of chemical compatibility with a particular reaction condition). Suitable protecting groups for the various functional groups of the 2,3-Substituted Azaindole Derivatives and methods for their installation and removal may be found in Greene et al., *Protective Groups in Organic Synthesis*, Wiley-Interscience, New York, (1999).

One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Methods suitable for the preparation of 2,3-Substituted Azaindole Derivatives are set forth above in Schemes 1-7.

One skilled in the art will recognize that the synthesis of 2,3-Substituted Azaindole Derivatives may require the construction of an amide bond. Methods include but are not limited to the use of a reactive carboxy derivative (e.g. acid halide, or ester at elevated temperatures) or the use of an acid with a coupling reagent (e.g. DECI, DCC) with an amine at 0° C. to 100° C. Suitable solvents for the reaction are halogenated hydrocarbons, ethereal solvents, dimethyl formamide and the like. The reaction can be conducted under pressure or in a sealed vessel.

The starting materials and the intermediates prepared using the methods set forth in Schemes 1-7 may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% $CH_3CN$, 5 min -95% $CH_3CN$, 5-7 min -95% $CH_3CN$, 7 min-stop. The retention time and observed parent ion are given. Flash column chromatography was performed using pre-packed normal phase silica from Biotage, Inc. or bulk silica from Fisher Scientific. The eluent for flash column chromatography was 0-30% ethyl acetate/hexane unless specified otherwise.

Example 1

Preparation of Compound 10

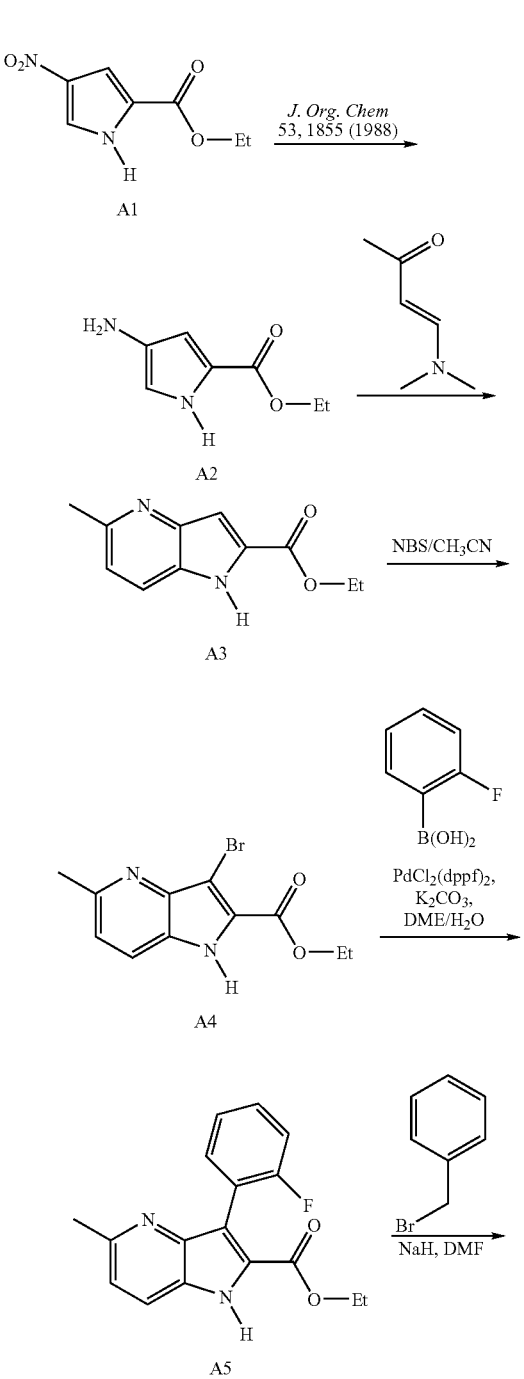

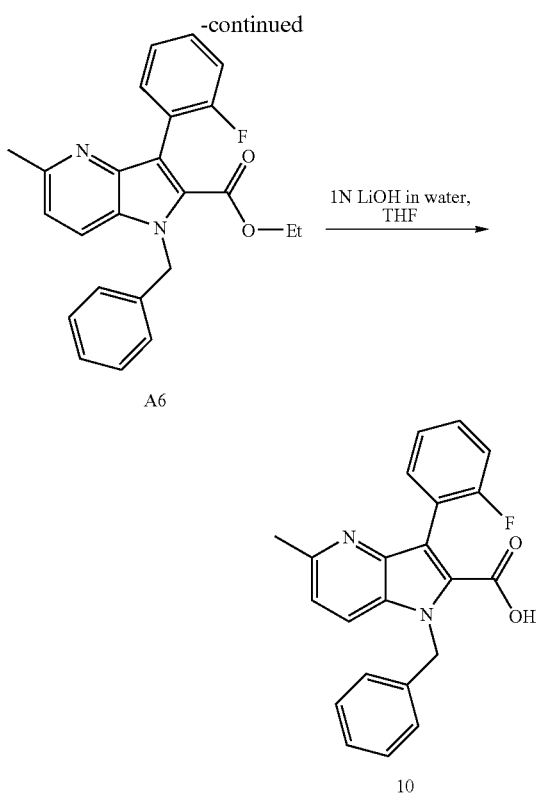

5-Methyl-1H-pyrrolo[3,2-b]pyridine-2-carboxylic acid ethyl ester A3 (0.081 g, 0.4 mmol) was dissolved in acetonitrile (4 mL) at room temperature. To the resulting mixture was added N-bromosuccinimide (0.086 g, 0.48 mmol) and the resulting suspension was stirred at room temperature for 3 hours. The reaction was then quenched by addition of aqueous saturated sodium thiosulfate solution (5 mL). The solvent was partially removed in vacuo and the residue obtained was diluted with ethyl acetate (50 mL) and the layers separated. The aqueous layer was extracted with ethyl acetate (50 mL) and the combined organic layers were washed with aqueous 1N sodium bicarbonate solution (10 mL), then brine (10 mL). The organic layer was dried (magnesium sulfate), filtered and concentrated in vacuo to provide the crude bromo intermediate A4 (0.11 g, 97% yield). MS: 283.19 (M+H)$^+$.

Intermediate compound A4 (50 mg, 0.18 mmol) was diluted with 1,2-dimethoxyethane (2 mL) and to the resulting solution was added mixture was added PdCl$_2$ (dppf)$_2$ (10 mol %), 2-fluorophenyl boronic acid (0.53 mmol), potassium carbonate (0.9 mmol), then water (0.3 mL).

The reaction mixture was heated to 100° C. and allowed to stir at this temperature for about 8 hours. The reaction mixture was then cooled to room temperature and diluted with ethyl acetate (100 mL). The resulting solution was filtered through a celite plug and the filtrate concentrated in vacuo to provide a crude residue that was purified using flash chromatography (ethyl acetate/hexane 0-30%) to provide compound A5 (0.028 g, 52% yield). MS: 299.2 (M+H)$^+$.

Compound A2 can be made from commercially available 4-nitropyrrole 2-carboxylic acid ethyl ester using the methods described in Moses et al., *J. Org. Chem.* 53(9):1855-1859 (1988).

A mixture of compound A2 (1.13 g, 10 mmol) and 1-dimethylamino-but-1-en-3-one (1.54 g, 10 mmol) were heated to 100° C. and allowed to stir at this temperature for about 14 hours. The crude reaction mixture was cooled to room temperature and purified using flash chromatography (0-30% ethyl acetate/hexane as eluent) to provide compound A3 (0.66 g, 32% yield). MS: 205.1 (M+H)$^+$.

3-(2-Fluoro-phenyl)-1H-pyrrolo[3,2-b]pyridine-2-carboxylic acid ethyl ester A5 (0.02 g, 0.07 mmol) was diluted with DMF (1 mL). To the resulting solution was added benzyl bromide (0.1 mmol) and sodium hydride (0.077 mmol). The resulting suspension was stirred at room temperature for 14 hours, then ethyl acetate (50 mL) and water (20 mL) were added to the reaction mixture and layers were separated. The organic layer was sequentially washed with aqueous saturated sodium bicarbonate solution (10 mL), water (10 mL) and saturated brine (10 mL). The separated organic solution was dried (magnesium sulfate), filtered and concentrated in vacuo to provide a crude residue which was purified using flash chromatography to provide 1-Benzyl-3-(2-fluoro-phenyl)-5-methyl-1H-pyrrolo[3,2-b]pyridine-2-carboxylic acid ethyl ester A6 (94% yield). MS: 389.2 (M+H)$^+$.

Step 4:

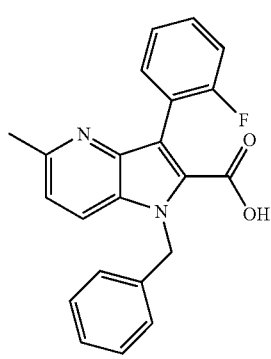

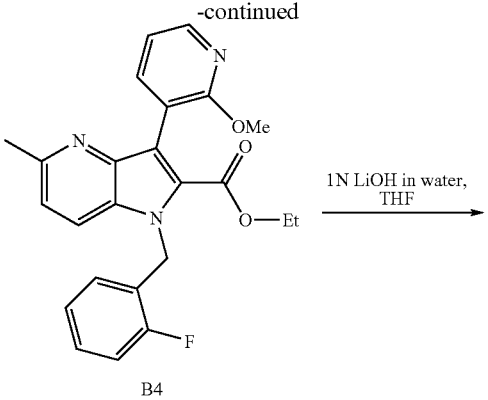

1-Benzyl-3-(2-fluoro-phenyl)-5-methyl-1H-pyrrolo[3,2-b]pyridine-2-carboxylic acid ethyl ester A6 (0.002 g, 0.005 mmol) was diluted with tetrahydrofuran (0.5 mL). To the resulting solution was added 1 M aqueous lithium hydroxide (0.0077 mmol). The reaction was heated to 60° C. and allowed to stir at this temperature for 10 days, then the reaction mixture was concentrated in vacuo and the resulting residue was washed with hexanes to provide compound 10 as a lithium salt (100% yield) which was used without further purification. MS: 361.2 (M+H)$^+$.

Example 2

Preparation of Compound 4

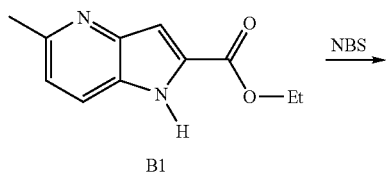

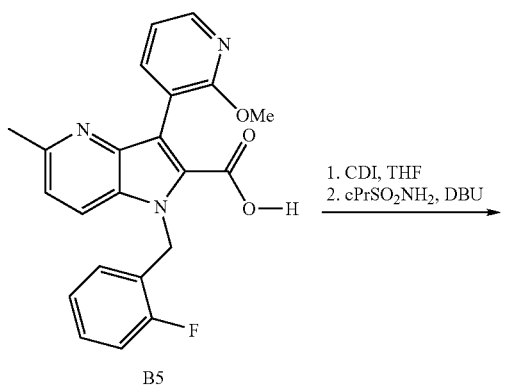

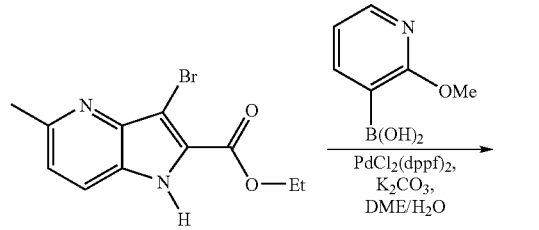

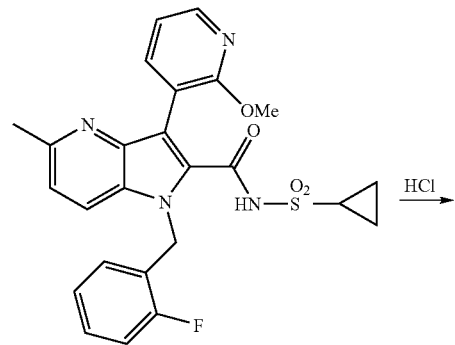

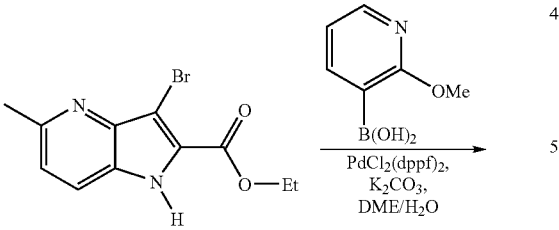

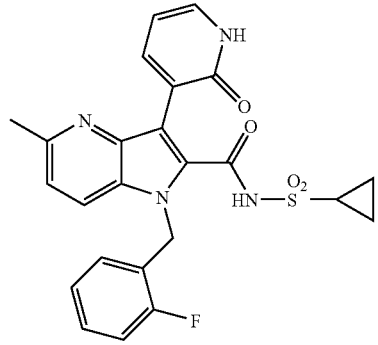

Step 1:

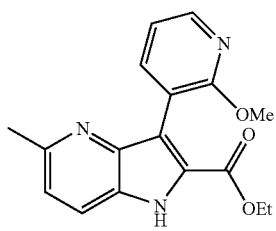

B3

5-Methyl-1H-pyrrolo[3,2-b]pyridine-2-carboxylic acid ethyl ester B1 (0.204 g, 1 mmol) was diluted with acetonitrile (10 mL). To the resulting solution was added N-bromosuccinimide (0.214 g, 1.2 mmol) and the resulting suspension was stirred at room temperature for 3 hours. The reaction was quenched by addition of aqueous saturated sodium thiosulfate solution (10 mL) and the reaction mixture was concentrated in vacuo. The crude residue obtained was diluted with ethyl acetate (50 mL) and the layers were separated. The aqueous layer was extracted with ethyl acetate (50 mL) and the combined organic layers were then washed with aqueous 1N sodium bicarbonate solution (10 mL), then brine (10 mL). The organic solution was then dried (magnesium sulfate), filtered and concentrated in vacuo to provide crude bromo intermediate B2 (0.32 g, quantitative). MS: 283.09 (M+H)+.

Compound B2 was diluted with 1,2-dimethoxyethane (5 mL) and to the resulting solution was added $PdCl_2$ $(dppf)_2$ (0.082 g, 10 mol %) and the resulting reaction heated to 90° C. and allowed to stir at this temperature for 30 minutes. 2-methoxypyridyl-3-boronic acid (0.459 g, 3 mmol), potassium carbonate (0.69 g, 5 mmol), and water (0.5 mL) were added in three portions sequentially over 5 minutes. The reaction was heated to 90° C. and allowed to stir at this temperature for 0.5 hours. The reaction mixture was then cooled to room temperature, diluted with ethyl acetate (100 mL). filtered through a celite plug and the then concentrated in vacuo. The resulting crude product was purified using flash chromatography to provide 3-(2-Methoxy-pyridin-3-yl)-5-methyl-1H-pyrrolo[3,2-b]pyridine-2-carboxylic acid ethyl ester B2 (0.21 g, 67% yield). MS: 312.72 (M+H)+.

Step 2:

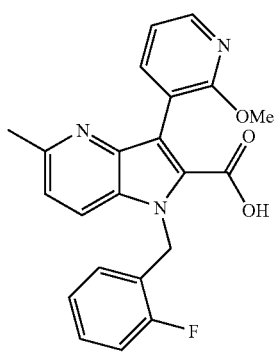

B5

3-(2-Methoxy-pyridin-3-yl)-5-methyl-1H-pyrrolo[3,2-b]pyridine-2-carboxylic acid ethyl ester B3 (0.2 g, 0.64 mmol) was diluted with DMF (4 mL). To the resulting solution was added 2-fluorobenzyl chloride (0.14 g, 0.96 mmol) and cesium carbonate (0.312 g, 0.96 mmol) and the resulting suspension was allowed to stir at room temperature. After 24 hours the reaction mixture was then diluted with ethyl acetate (50 mL) and water (20 mL) and the layers were separated. The organic layer was sequentially washed with aqueous saturated sodium bicarbonate solution (10 mL), water (10 mL) and saturated brine (10 mL), dried (magnesium sulfate), filtered and concentrated in vacuo. The crude residue obtained was purified using flash chromatography to provide 1-(2-Fluoro-benzyl)-3-(2-methoxy-pyridin-3-yl)-5-methyl-1H-pyrrolo[3,2-b]pyridine-2-carboxylic acid ethyl ester B4 (0.26 g) MS: 420.20 (M+H)+.

Compound B4 was diluted with tetrahydrofuran (3 mL) and to the resulting solution was added 1M aqueous lithium hydroxide (2 mL, excess). The reaction was heated to 70° C. and allowed to stir at this temperature for 14 hours. The reaction was then acidified using 1M HCl, and extracted several times with ethyl acetate. The organic layer was collected and concentrated in vacuo to provide 1-(2-Fluoro-benzyl)-3-(2-methoxy-pyridin-3-yl)-5-methyl-1H-pyrrolo[3,2-b]pyridine-2-carboxylic acid B5 (0.2 g, 80% yield). MS: 392.16 (M+H)+.

Step 3:

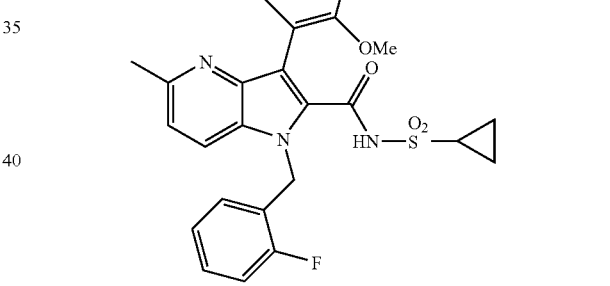

B6

1-(2-Fluoro-benzyl)-3-(2-methoxy-pyridin-3-yl)-5-methyl-1H-pyrrolo[3,2-b]pyridine-2-carboxylic acid B5 (100 mg, 0.25 mmol) was diluted with tetrahydrofuran (3 mL) and to the resulting solution was added carbonyl diimidazole (62 mg, 0.38 mmol). The resulting suspension was heated to reflux and allowed to stir at this temperature for 1 hour. The reaction mixture was cooled to room temperature and cyclopropanesulfonamide (46 mg, 0.38 mmol) and 1,8-diazabicyclo(5.4.0)undec-7-ene (76 mg, 0.5 mmol) was added. The resulting reaction was stirred at room temperature for an additional 14 hours, then concentrated in vacuo. The residue obtained was diluted with ethyl acetate (100 mL) and water (10 mL). The organic layer was separated and the aqueous layer extracted twice more with ethyl acetate (2×20 mL). The combined organic layers were dried (magnesium sulfate), filtered and concentrated in vacuo to provide a crude residue which was purified using flash chromatography to provide cyclopropanesulfonic acid [1-(2-fluoro-benzyl)-3-(2-methoxy-pyridin-3-yl)-5-methyl-1H-pyrrolo[3,2-b]pyridine-2-carbonyl]-amide B6 (0.09 g, 72% yield). MS: 495.3 (M+H)+.

Step 4:

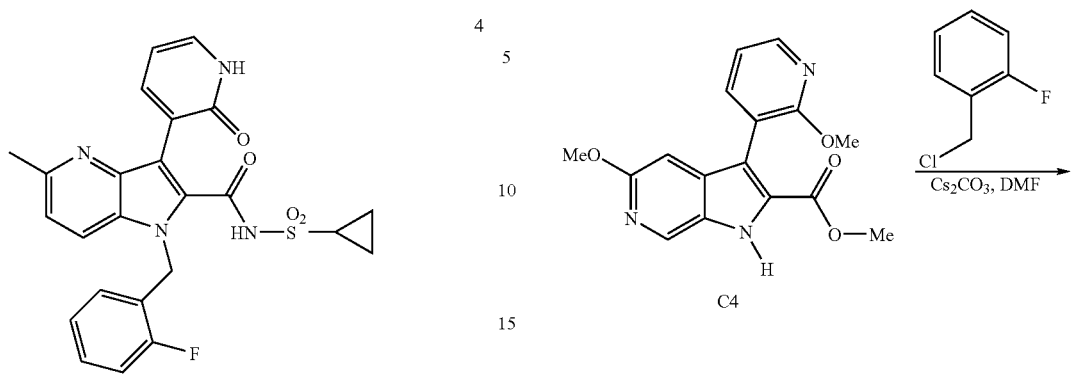

Cyclopropanesulfonic acid [1-(2-fluoro-benzyl)-3-(2-methoxy-pyridin-3-yl)-5-methyl-1H-pyrrolo[3,2-b]pyridine-2-carbonyl]-amide B6 (80 mg, 0.16 mmol) was dissolved in 4 N HCl in 1,4-dioxane (5 mL) and the resulting reaction mixture was heated to 90° C. under a nitrogen atmosphere and allowed to stir at this temperature for 40 minutes. The reaction mixture was then cooled to room temperature and concentrated in vacuo to provide a crude residue which was purified using flash chromatography to provide compound 4 (50 mg, 62% yield). MS: 481.3 (M+H)$^+$ Example 3

Preparation of Compound 3

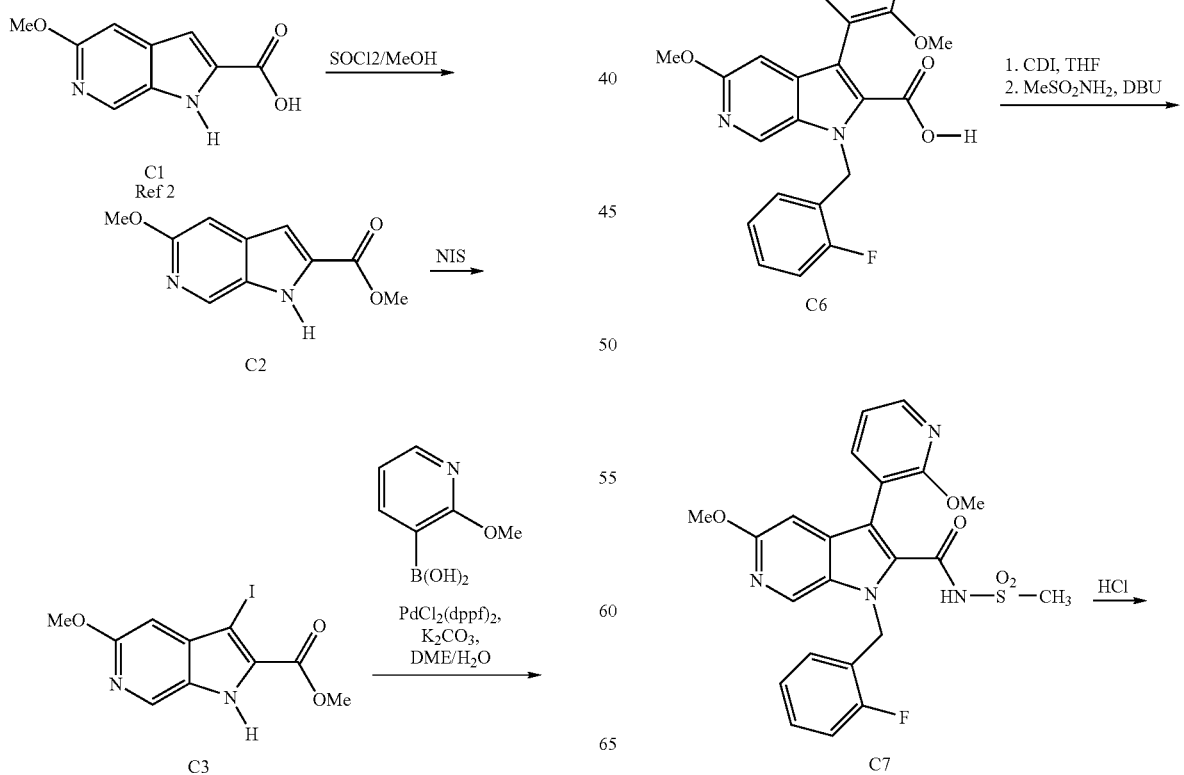

-continued

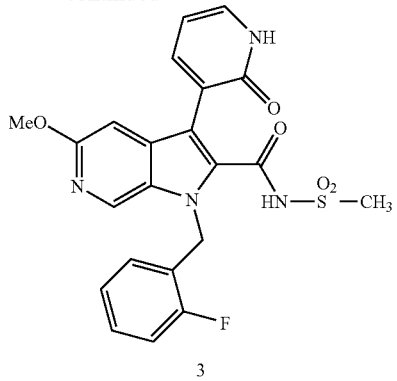

3

Step 1:

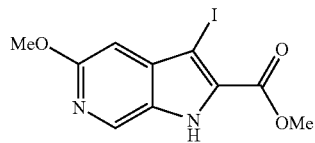

C3

5-Methoxy-1H-pyrrolo[2,3-c]pyridine-2-carboxylic acid C1 (0.4 g, 2.08 mmol; prepared according to the method described in Frydman, et. al; *J. Am. Chem. Soc.,* 87(15):3530-3531 (1965)) was dissolved in MeOH (10 mL) and to the resulting solution was added thionyl chloride (1 mL, excess) dropwise. The resulting suspension was allowed to stir at room temperature for 48 hours. The reaction mixture was concentrated in vacuo and the residue obtained was portioned between ethyl acetate and saturated aqueous NaHCO$_3$ solution. The organic layer was washed with water, dried (MgSO$_4$) and concentrated in vacuo to intermediate compound C2 (0.34 g, 1.64 mmol). MS: 207.13 (M+H)$^+$.

Compound C2 was diluted with chloroform and to the resulting solution was added N-iodosuccinimide (0.388 g, 1.72 mmol). The resulting reaction was allowed to stir at room temperature for about 20 hours. Aqueous saturated sodium thiosulfate solution (10 mL) was added to the reaction mixture and chloroform was removed in vacuo. The aqueous solution obtained was diluted with ethyl acetate (50 mL) and layers were separated. The aqueous layer was extracted with ethyl acetate (50 mL) and the combined organic layers were washed with aqueous 1N sodium bicarbonate solution (10 mL) and brine (10 mL). The organic solution was dried (magnesium sulfate), filtered and concentrated in vacuo to provide 3-Iodo-5-methoxy-1H-pyrrolo[2,3-c]pyridine-2-carboxylic acid methyl ester C3 (0.6 g, 86% overall yield). MS: 332.89 (M+H)$^+$.

Step 2:

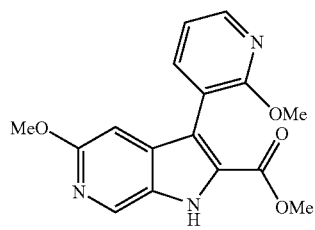

C4

3-Iodo-5-methoxy-1H-pyrrolo[2,3-c]pyridine-2-carboxylic acid methyl ester C3 (0.3 g, 0.9 mmol) was diluted with 1,2-dimethoxyethane (5 mL) and to the resulting solution was added PdCl$_2$(dppf)$_2$ (0.074 g, 10 mol %). The reaction was heated to 90° C. and allowed to stir at this temperature for 30 minutes. Pyridyl boronic acid (0.415 g, 2.7 mmol), potassium carbonate (0.621 g, 5 mmol), and water (0.3 mL) were then added to the reaction mixture in three portions over 5 minutes. The resulting reaction allowed to stir at 90° C. for an additional minutes, then the reaction mixture was cooled to room temperature, diluted with ethyl acetate (100 mL) and filtered through a celite plug. The filtrate was concentrated in vacuo and the resulting residue was purified using flash chromatography to provide 5-methoxy-3-(2-methoxy-pyridin-3-yl)-1H-pyrrolo[2,3-c]pyridine-2-carboxylic acid methyl ester C4 (0.075 g, 27% yield). MS: 314.2 (M+H)$^+$.

Step 3:

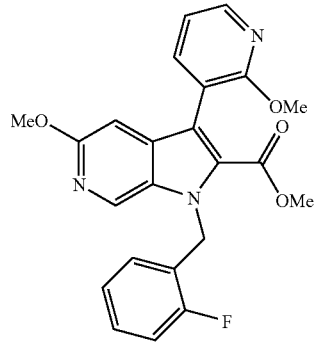

C5

5-methoxy-3-(2-methoxy-pyridin-3-yl)-1H-pyrrolo[2,3-c]pyridine-2-carboxylic acid methyl ester C4 (0.07 g, 0.22 mmol) was diluted with DMF (2 mL) and to the resulting solution was added 2-fluorobenzyl chloride (0.048 g, 0.33 mmol) and cesium carbonate (0.107 g, 0.33 mmol). The resulting suspension was allowed to stir at room temperature for 24 hours, then ethyl acetate (50 mL) and water (20 mL) were added to the reaction mixture and the layers were separated. The organic layer was sequentially washed with aqueous saturated sodium bicarbonate solution (10 mL), water (10 mL) and saturated brine (10 mL). The combined organic layers were dried (magnesium sulfate), filtered and concentrated in vacuo to provide a crude residue which was purified using flash chromatography to provide 1-(2-Fluoro-benzyl)-5-methoxy-3-(2-methoxy-pyridin-3-yl)-1H-pyrrolo[2,3-c]pyridine-2-carboxylic acid methyl ester C5 (0.07 g, 75%) MS: 422.20 (M+H)$^+$.

Step 4:

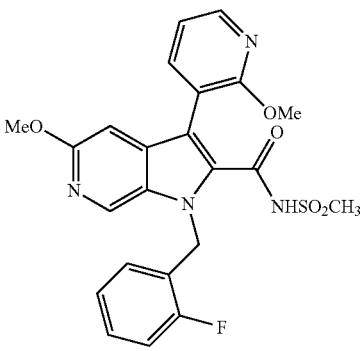

C7

1-(2-Fluoro-benzyl)-5-methoxy-3-(2-methoxy-pyridin-3-yl)-1H-pyrrolo[2,3-c]pyridine-2-carboxylic acid methyl ester C5 (55 mg, 0.13 mmol) was diluted with tetrahydrofuran (2 mL) and to the resulting solution was added 1M aqueous lithium hydroxide (0.39 mL, 0.39 mmol). The reaction was heated to 70° C. and allowed to stir at this temperature for 14 hours. 1M HCl was then added to the reaction and the reaction mixture was extracted several times with ethyl acetate. The combined organic extracts were concentrated in vacuo to provide the crude free acid C6 (65 mg).

Compound C6 was diluted with tetrahydrofuran (3 mL) and to the resulting solution was added carbonyl diimidazole (32 mg, 0.195 mmol). The resulting suspension was heated at reflux for 1 hour, then cooled to room temperature. Methanesulfonamide (19 mg, 0.195 mmol) and 1,8-diazabicyclo (5.4.0)undec-7-ene (40 mg, 0.26 mmol) were added to the cooled reaction mixture and the resulting reaction was allowed to stir at room temperature for an additional 14 hours. The reaction mixture was concentrated in vacuo and the resulting residue was diluted with ethyl acetate (100 mL) and water (10 mL). The organic layer was back-washed with saturated brine (10 mL) and the combined organics were dried (magnesium sulfate), filtered and concentrated in vacuo. The crude product obtained was purified using flash chromatography to provide N-[1-(2-Fluoro-benzyl)-5-methoxy-3-(2-methoxy-pyridin-3-yl)-1H-pyrrolo[2,3-c]pyridine-2-carbonyl]-methanesulfonamide C7 (0.03 g, 48% overall yield). MS: 485.3 (M+H)$^+$.

Step 5:

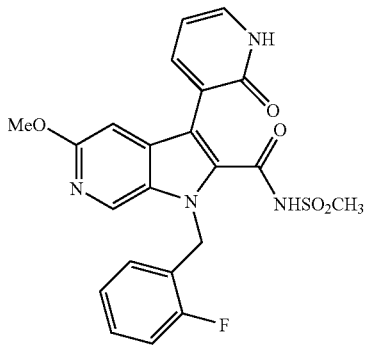

3

N-[1-(2-Fluoro-benzyl)-5-methoxy-3-(2-methoxy-pyridin-3-yl)-1H-pyrrolo[2,3-c]pyridine-2-carbonyl]-methanesulfonamide C7 (30 mg, 0.061 mmol) was dissolved in 4 N HCl in 1,4-dioxane (3 mL) and the resulting solution was heated to 90° C. under a nitrogen atmosphere and allowed to stir at this temperature for 1 hour. The reaction mixture was cooled to room temperature, then concentrated in vacuo to provide a residue which was purified using flash chromatography to provide compound 3 (10 mg, 35% yield). MS: 471.3 (M+H)$^+$ Example 4

Preparation of Compound 7

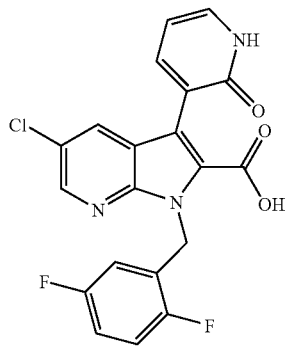

7

-continued

Step 1:

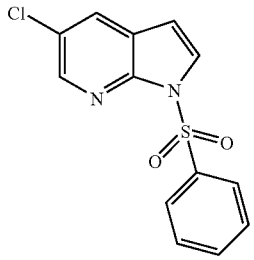

D1

To a solution of phenylsulfonyl chloride (4.2 g, 23.77 mmol) in toluene (35 mL) was added 50% aq. NaOH (50 mL) and tetra-butyl ammonium iodide (729 mg, 4.00 mmol) and the resulting reaction was allowed to stir for 10 minutes at room temperature. A solution of compound 5-chloro azaindole (3.00 g) in toluene (60 mL, only partially soluble) was then added dropwise. The resulting reaction was then stirred at room temperature for 2 hours, diluted with water and extracted into EtOAc (300 mL). The combined organic layers were dried (MgSO$_4$), filtered, and concentrated in vacuo to provide a crude residue which was purified using flash column chromatogrpahy (EtOAc/Hexanes) to provide compound D1 which was used without further purification.

Step 2:

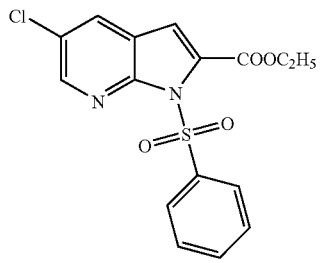

D2

To a solution of compound D1 (5.00 g, 17.00 mmol) in THF (30 mL) at −78° C. under argon atmosphere, was added dropwise a solution of tert-butyllithium in THF (12.00 mL, 20.4 mmol) and the resulting reaction was stirred at −78° C. for 20 minutes. A solution of ethyl chloroformate (2.75 g, 25.5 mmol) in THF (10 mL) was then added to the reaction and the reaction was allowed to warm up to room temperature over 2 hours. The reaction mixture was then diluted with water (50 mL) and the resulting solution was extracted with EtOAc (300 mL). The combined organic layers were dried (MgSO$_4$), filtered, concentrated in vacuo, and the resulting residue was purified using flash column chromatography (Hexanes/Ether, 0 to 40%) to provide compound D2 (3.1 g, 50%) as a colorless solid. $^1$H NMR (500 MHz, d$_6$-dmso), δ, 8.59 (d, 1H, J=2.2 Hz), 8.32 (d, 1H, J=2.2 Hz), 8.23 (dd, 1H, J=1.3 & 7.6 Hz), 7.80 (tt, 1H, J=1.3 & 7.5 Hz), 7.72 (tt, 1H, J=1.6 & 8.2 Hz), 7.30 (s, 1H), 4.42 (q, 2H, J=7.3 Hz), 1.36 (t, 3H, J=7.3 Hz).

Step 3:

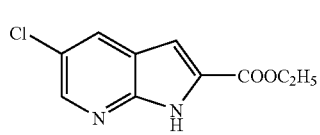

To a solution of compound D2 (3.00 g, 8.25 mmol) in THF (30.00 mL) was added TBAF.3H$_2$O (3.12 g, 9.8 mmol) and the resulting reaction was heated to reflux. After 12 hours the reaction mixture was then diluted with EtOAc (100 mL) and washed extensively with water. The combined organic layers were dried (MgSO$_4$), filtered and concentrated in vacuo and the crude residue obtained was purified using flash column chromatography on silica gel (EtOAc/Hexanes) to provide compound D3.

Step 4:

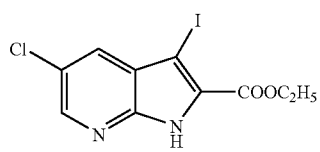

To a solution of compound D3 (2.0 g, 8.8 mmol) in CH$_2$Cl$_2$ (10 mL), and DMF (2.00 mL) was treated with N-iodosuccinimde (2.18 g, 9.68 mmol) and stirred at room temperature for 12 hours. A colorless solid separated from the reaction which was filtered and concentrated in vacuo to provide compound D4. $^1$H NMR (500 MHz, d$_6$-dmso), δ, 13.1 (s, 1H), 8.47 (s, 1H), 7.91 (s, 1H), 4.39 (bs, 2H), 1.39 (bs, 3H).

Step 5:

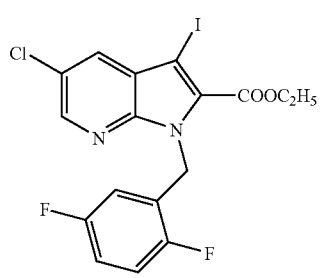

To a solution of compound D4 (300 mg, 0.85 mmol) in DMF (10 mL) was added cesium carbonate (569 mg, 1.75 mmol) and 2,5-difluorobenzyl bromide (351 mg, 1.72 mmol) and the resulting reaction was allowed to stir at room temperature for 5 hours. The reaction mixture was then diluted with EtOAc (250 mL) and washed with brine (2×100 mL). The combined organic layers were dried (MgSO$_4$), filtered and concentrated in vacuo to provide a crude residue which was purified using flash column chromatography on silica gel (EtOAc/Hexanes 0 to 20%) to provide compound D5 as a colorless solid.

Step 6:

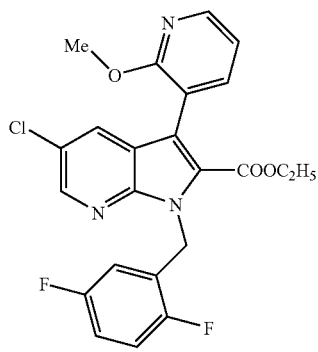

To a solution of compound D5 (400 mg, 0.84 mmol) in DME (10 mL) was added 2-methoxypyridin-3-yl-boronic acid (152 mg, 1.00 mmol) and Pd(dppf)Cl$_2$.CH$_2$Cl$_2$ (69 mg), and the resulting reaction was placed under nitrogen atmosphere and stirred at room temperature for 0.5 hours. A solution of potassium carbonate (468 mg, 3.36 mmol) in 10 mL of water was then added to the reaction mixture and the resulting reaction was heated at 90° C. After 1 hour the reaction mixture was diluted with EtOAc (250 mL), concentrated in vacuo and the residue obtained was purified using flash column chromatography on silica gel (EtOAc/Hexanes 0 to 20%) to provide compound D6 as a solid. MS=459 (M+H)

Step 7:

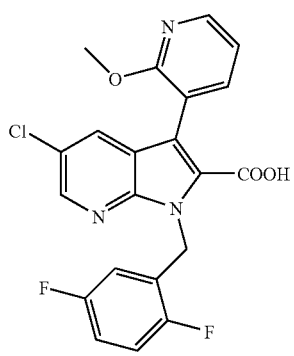

To a solution of compound D6 (350 mg, 0.81 mmol), in a mixture of THF/water/methanol (10 mL each) was added lithium hydroxide monohydrate (156 mg, 3.71 mmol) and the resulting reaction was heated to reflux and allowed to stir at this temperature for 4 hours. The reaction mixture was diluted with aq HCl (1M) and concentrated in vacuo to provide a residue which was used without further purification. MS=431 (M+H)

Step 8:

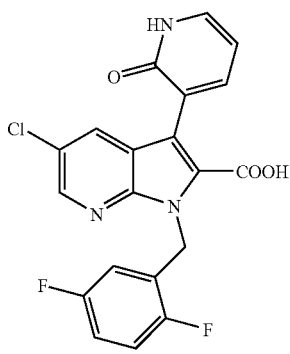

A solution of compound D7 (80 mg, 0.18 mmol) in 4 M HCl in dioxane (8.00 mL) and methanol (2.00 mL) was heated to 80° C. and allowed to stir at this temperature for 3 hours. The reaction mixture was then concentrated in vacuo and the crude residue obtained was purified using reverse phase HPLC (C18-column, acetonitrile, water; 0 to 100%) to provide compound 7 as a colorless solid. $^1$H NMR (500 MHz, d$_6$-dmso), δ, 13.41 (bs, 1H), 11.85 (bs, 1H), 8.48 (d, 1H, J=2.2 Hz), 8.02 (d, 1H, J=1.9 Hz), 7.66 (d, 1H, J=5.7 Hz), 7.45 (d, 1H, J=5.7 Hz), 7.29 (td, 1H, J=4.7 & 4.4 Hz), 7.18-7.13 (m, 1H), 6.51-6.46 (m, 1H), 6.34 (bt, 1 H, J=6.3 Hz), 5.88 (s, 2H). LRMS m/z calculated for Chemical Formula: $C_{20}H_{13}ClF_2N_3O_3$ (M+1)$^+$: 416.06. Found: 416.09

Example 5

Preparation of Compound 1

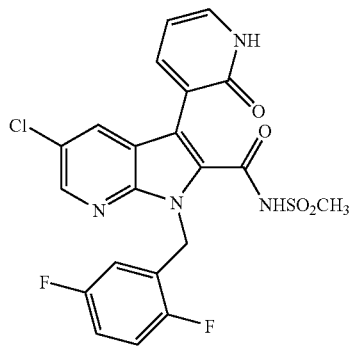

Step 1:

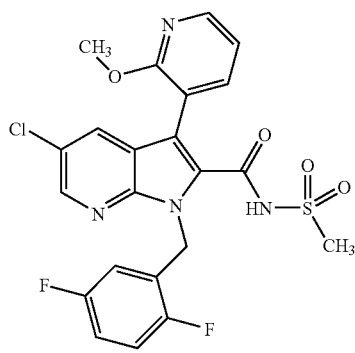

To a solution of compound D7 (150 mg, 0.35 mmol) in 5 mL of dry THF was added CDI (67 mg, 0.41 mmol) and the resulting reaction was heated to reflux. After 3 hours the reaction mixture was cooled to room temperature and methanesulfonamide (39 mg, 0.41 mmol) and DBU (100 mg, 0.65 mmol) were added. The resulting reaction was stirred at 65° C. for 16 hours, then diluted with EtOAc (150 mL) and washed with water. The combined organic layers were dried (MgSO$_4$), filtered, and concentrated in vacuo to provide a crude residue which was purified using flash column chromatography (acetone/CH$_2$Cl$_2$ 0-70%) to provide compound E1 as a colorless solid. MS=507 (M+H)

Step 2:

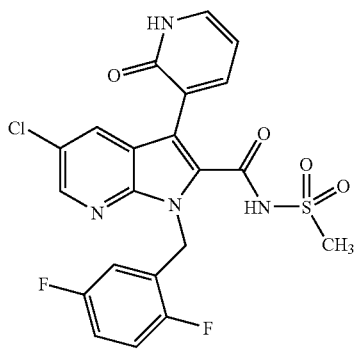

A solution of compound E1 (80 mg, 0.18 mmol) in 4 M HCl in dioxane (8.00 mL) and methanol (2.00 mL) was heated to 80° C. and allowed to stir at this temperature for 3 hours. The reaction mixture was then concentrated in vacuo and the crude residue obtained was purified using reverse phase HPLC (C18 column, water/acetonitrile 0 to 100%) to provide compound 1. $^1$H NMR (500 MHz, d$_6$-dmso), δ, 12.80 (bs, 1H), 12.45 (bs, 1H), 8.52 (d, 1H, J=2.2 Hz), 8.08 (d, 1H, J=2.2 Hz), 7.80 (dd, 1H, J=1.9 & 5.0 Hz), 7.61 (bd, 1H, J=5.1 Hz), 7.23 (dt, 1H, J=2.5 & 11.6 Hz), 7.05-6.97 (m, 2H), 6.53 (t, 1H, J=6.9 Hz), 5.75 (s, 2H), 3.26 (s, 3H). LRMS m/z calculated for $C_{21}H_{16}ClF_2N_4O_4S$ (M+H)$^+$: 493.05 Found: 493.10.

Example 6

Preparation of Intermediate Compound 6A

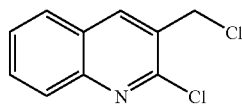

Step A—Synthesis of Compound 6A

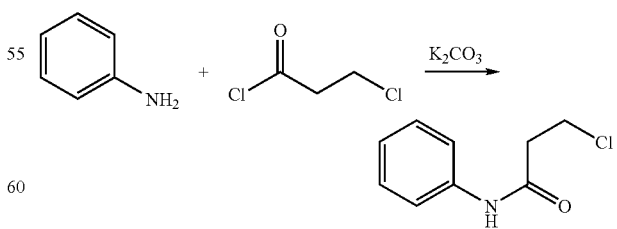

A mixture of aniline (65.04 mL, 713.8 mmol), potassium carbonate (54.4 g, 394 mmol) and water (300 mL) were added to a 2000 mL flask. The resulting reaction was kept at room temperature using a room temperature water bath and stirred with a mechanic stirrer. 3-Chloro-propionyl chloride (75.18 mL, 787.6 mmol) was added dropwise via additional funnel and the resulting suspension was allowed to stir at room temperature for 3 hours. The reaction mixture was filtered and the collected solid was washed sequentially with water (300 mL), aq. HCl (1M, 2×300 mL), and water (300 mL), then dried to provide compound 6A, which was used without purification (114.5 g, 87%).

Step B—Synthesis of Compound 6B

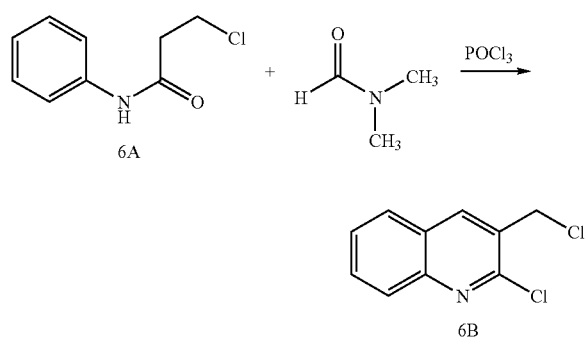

N,N-Dimethylformamide (53.7 mL, 694 mmol) was charged into a three necked flask and cooled to 0° C. and treated with phosphoryl chloride (177.7 mL, 1906 mmol) dropwise. The reaction was stirred at that temperature for 10 min and treated with 3-Chloro-N-phenylpropanamide BB1 (50.00 g, 272.3 mmol) and stirred at room temperature. for 30 min. The reaction mixture was heated at 80° C. for 3 h and slowly poured into ice. The solid separating out was filtered and washed extensively with water (2×1000 mL), aq. saturated sodium bicarbonate (500 mL), and taken in EtOAc (1 L), The solution was dried (MgSO$_4$) filtered concentrated in vacuo and the residue obtained was recrystallized from boiling hexanes to provide compound 6B (20 g).

Example 7

Preparation of Intermediate Compounds 7 and 7

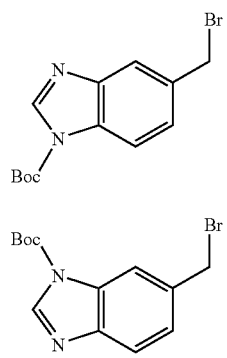

DD5

DD6

Step A—Synthesis of Compound DD2

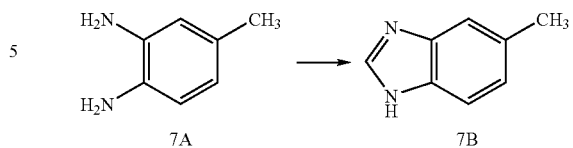

A solution of compound 7A (3 g, 24.5 mmol) in trimethyl orthoformate (15 mL) was treated with 2 drops conc. HCl and heated to 80° C. for 2 hours. The reaction mixture was cooled to room temperature and concentrated in vacuo to provide compound 7B (3.65 g), which was used without further purification. M.S. found for $C_8H_8N_2$: 133.2 (M+H)$^+$.

Step B—Synthesis of Compounds 7C and 7D

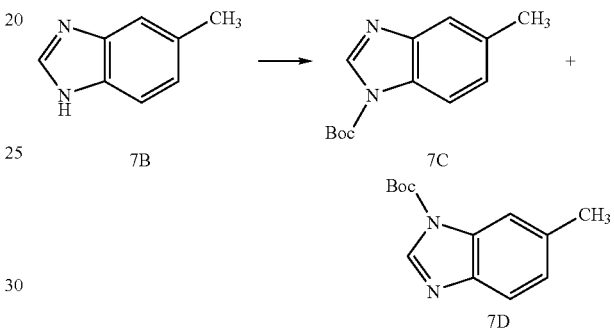

To a solution of compound 7B (24.5 mmol) in CH$_3$CN (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds 7C and 7D (5.38 g, 94.3% yield over steps A and B).

Step C—Synthesis of Compounds 7E and 7F

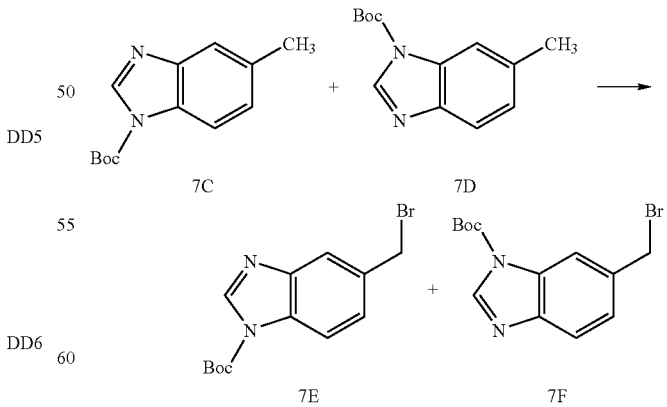

To a solution of compounds 7C and 7D (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C.

and allowed to stir at this temperature for 12 hours. The reaction was cooled to room temperature, solids were filtered off and the filtrate was washed with water, dried over sodium sulfate and concentrated in vacuo to provide compounds 7E and 7F (2.58 g) which was used without further purification. M.S. found for $C_{13}H_{15}BrN_2O_2$: 334.7 $(M+Na)^+$.

Example 8

Preparation of Intermediate Compound 8B

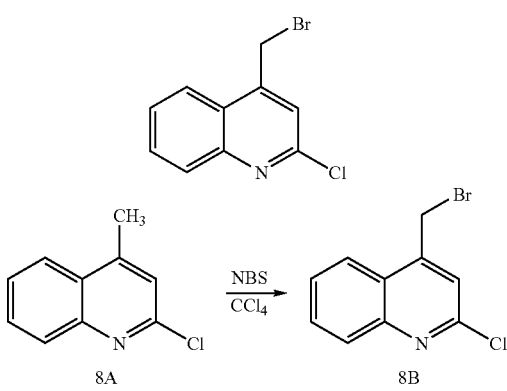

A mixture of compound 8A (1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound 8B, and was used without further purification.

Example 9

Preparation of Intermediate Compound 9G

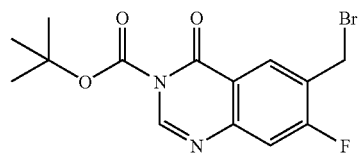

Step A—Synthesis of Compound 9B

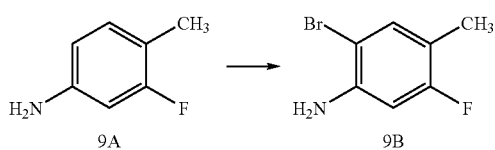

A mixture of compound 9A (6.00 g, 47.9 mmol) and anhydrous potassium carbonate (6.70 g, 48.5 mmol) in anhydrous dichloromethane (130 mL) was cooled to −15° C. in a salt-ice bath and then added dropwise to a solution of bromine (7.70 g, 48.2 mmol) in anhydrous dichloromethane (80 mL). After addition was complete, the reaction was allowed to stir at −15° C. for 1 hour. Ice water (100 mL) was added to the reaction mixture and the aqueous layer was extracted with dichloromethane (2×100 mL). The combined organic layers were dried over $MgSO_4$ and concentrated in vacuo to provide compound 9B (11.0 g, quant.), which was used without further purification.

Step B—Synthesis of Compound 9C

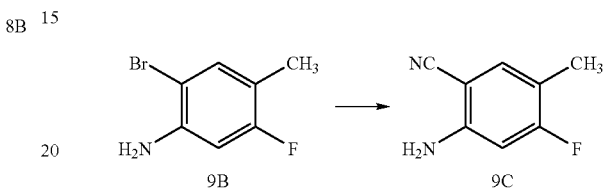

Compound 9B was dissolved in DMF (150 mL) and to this solution was added copper (I) cyanide (11.0 g, 123 mmol). The mixture was heated to 160° C. and allowed to stir at this temperature for 20 hours. After being cooled to room temperature, with water (200 mL), iron (III) chloride (42.0 g, 155 mmol) and concentrated hydrochloric acid (20 mL) were added to the reaction mixture and the resulting reaction was stirred for 45 minutes. The reaction mixture was then basified to pH>10 using commercial ammonium hydroxide solution. The basic solution was then extracted with ethyl acetate (4×400 mL). The combined organic extracts were washed with water, dried over magnesium sulfate, filtered and concentrated in vacuo. The residue obtained was purified using flash chromatography to provide compound 9C (5.82 g, 81%). $^1$H NMR (400 MHz, $d_6$-DMSO): δ 7.34 (d, J=8.4 Hz, 1H), 6.52 (d, J=12.4 Hz, 1H), 6.10 (s, 2H), 2.08 (s, 3H).

Step C—Synthesis of Compound 9D

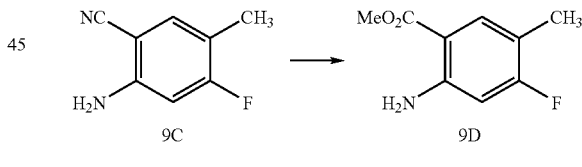

To the solution of 9C (2.0 g, 13.3 mmol) in anhydrous methanol (15 mL) at room temperature was added concentrated sulfuric acid (4.0 mL). The reaction mixture was heated to 70° C. and stirred for four days. After cooled to room temperature, it was poured into with ice water. The mixture was then diluted with ethyl acetate (200 mL) and was made basic (pH>10) with commercial ammonium hydroxide solution. The layers were separated. The aqueous layer was extracted with ethyl acetate (2×100 mL). The combined organic solution was dried over $MgSO_4$ and concentrated in vacuo to provide the crude product which, was purified using flash chromatography to provide compound 9D (1.0 g, 41%) and some recovered 5C. $^1$H NMR (400 MHz, $d_6$-DMSO): δ 7.61 (d, J=8.8 Hz, 1H), 6.69 (s, 2H), 6.51 (d, J=12.0 Hz, 1H), 3.77 (s, 3H), 2.06 (s, 3H).

Step D—Synthesis of Compound 9E

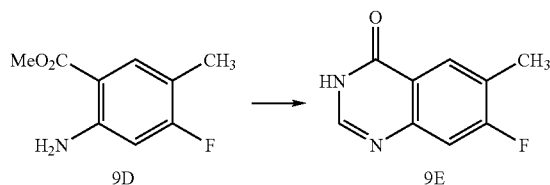

The solution of compound 9D (500 mg, 2.73 mmol) in formamide (6.0 mL) was heated to 150° C. in an oil bath and stirred for 18 hours. After cooled to room temperature, ethyl acetate (100 mL) and water (100 mL) were added and the layers were separated. The organic solution was washed with water (2×60 mL), dried over MgSO$_4$ and concentrated in vacuo to provide the crude product 9E (0.50 g, quant.) which, was used without further purification. MS found for $C_9H_7FN_2O$: 179.0 (M+H)$^+$.

Step E—Synthesis of Compound 9F

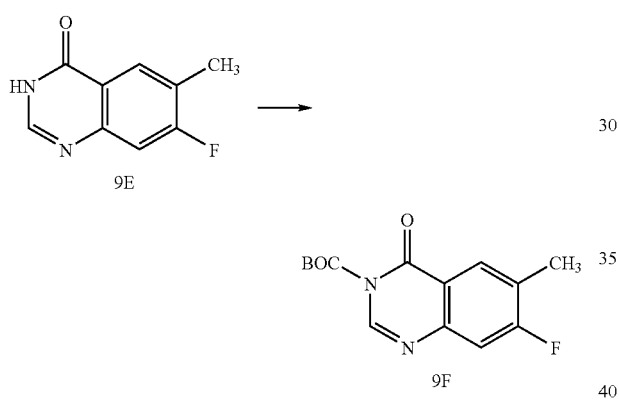

To the solution of 9E (from Step 4) in anhydrous THF (20 mL) at room temperature was added di-tert-butyl dicarbonate (1.84 g, 8.43 mmol), 4-dimethylaminopyridine (350 mg, 2.86 mmol) and triethyl amine (0.40 mL, 2.87 mmol). The reaction mixture was stirred for 18 hours. Ethyl acetate (100 mL) and water (100 mL) were added and the layers were separated. The aqueous layer was extracted with ethyl acetate (2×50 mL). The combined organic solution was dried over MgSO$_4$ and concentrated in vacuo to provide the crude product which, was purified using flash chromatography to provide compound 9F (285 mg, 36%). MS found for $C_{14}H_{15}FN_2O_3$: 179.0 (M+H-100)$^+$.

Step F—Synthesis of Compound 9G

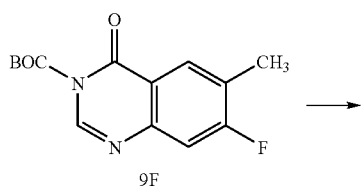

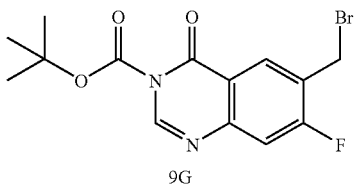

The mixture of 9F (282 mg, 1.01 mmol), NBS (253 mg, 1.42 mmol) and AIBN (58 mg, 0.353 mmol) in anhydrous carbon tetrachloride (60 mL) was heated to 90° C. in an oil bath and stirred for 4 hours. After cooled to room temperature and concentrated in vacuo, the residue was dissolved in ethyl acetate (100 mL) and water (100 mL). The layers were separated. The organic solution was washed with water (100 mL), dried over MgSO$_4$ and concentrated in vacuo to provide the crude product 9G (453 mg, quant.) which, was used without further purification.

Example 10

Preparation of Intermediate Compound 10E

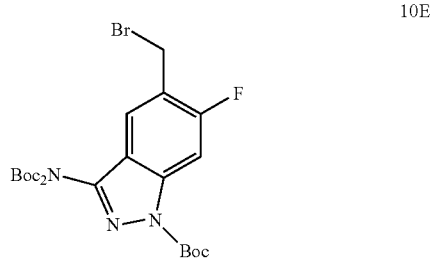

Step A—Synthesis of Compound 10A

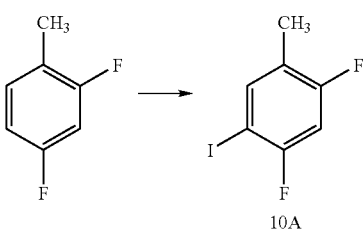

A solution of 2,4-difluorotoluene (4.72 g, 36.8 mmol) in trifluoroacetic acid (12.29 mL, 159.5 mmol) was cooled to 0° C., then N-Iodosuccinimide (9.59 g, 42.6 mmol) was added and the resulting reaction was allowed to stir at room temperature for about 15 hours. The reaction mixture was then concentrated in vacuo and the residue obtained was dissolved in hexanes (100 mL), washed with aqueous sodium thiosulfate (100 mL), brine (100 mL), then dried (MgSO$_4$), filtered and concentrated in vacuo. The resulting residue was purified using bulb-to-bulb distillation to provide compound 10A (7.2 g, 77%) as a colorless oil.

Step B—Synthesis of Compound 10B

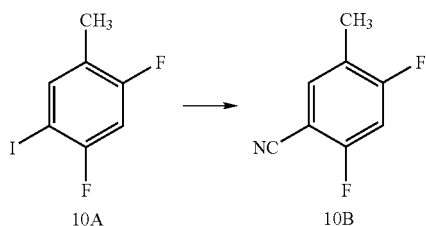

A solution of compound 10A (7.11 g, 28.0 mmol), zinc cyanide (1.97 g, 16.8 mmol) and tetrakis(triphenylphosphine) palladium(0) (3.23 g, 2.80 mmol) in DMF (30 mL) was heated to 90° C. and allowed to stir at this temperature for 1.5 hours. The reaction mixture was concentrated in vacuo and the residue obtained was taken up in water (400 mL) and extracted with ether (400 mL). The organic extract was washed with aqueous ammonium hydroxide solution (1N). The organic layer was dried (MgSO$_4$) filtered, concentrated in vacuo to provide a residue that was purified using flash column chromatography (SiO$_2$, EtOAc/Hexanes) to provide a mixture that contained product and triphenylphosphine. This mixture was further purified using sublimation at 1 mm/Hg at 45° C. to provide compound 10B (1.8 g; Yield=42%).

Step C—Synthesis of Compound 10C

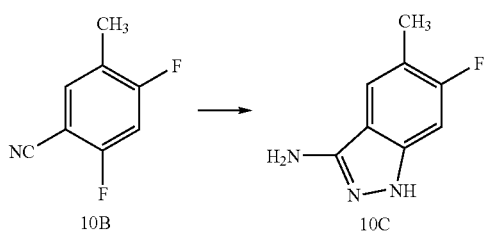

A solution of compound 10B (1.400 g, 9.154 mmol) and hydrazine (0.700 mL, 22.3 mmol) in isopropyl alcohol (50 mL, 653.1 mmol), was heated to reflux and allowed to stir at this temperature for 24 hours. The reaction mixture was cooled to room temperature, concentrated in vacuo and the residue obtained was purified using flash column chromatography (SiO$_2$, Acetone/Hexanes 0→50%) to provide compound 10C (330 mg, 22%).

Step D—Synthesis of Compound 10D

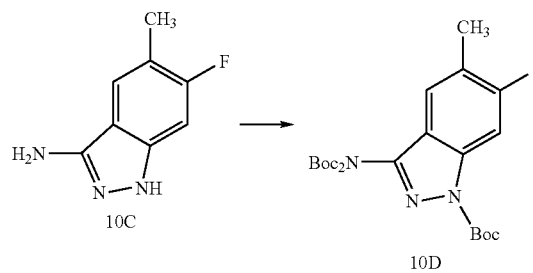

A solution of compound 10C (330.00 mg, 1.998 mmol), di-tert-butyldicarbonate (2.6163 g, 11.98 mmol) and 4-dimethylaminopyridine (48.817 mg, 0.39959 mmol) in acetonitrile (15 mL, 287.2 mmol) was heated to reflux and allowed to stir at this temperature for 2 hours. The reaction mixture was cooled to room temperature, concentrated in vacuo, and the resulting residue was purified using flash column chromatography (SiO$_2$, EtOAc/Hexanes 0-20%) to provide compound 10D (640.00 mg, 68%) as a colorless oil.

Step E—Synthesis of Compound 10E

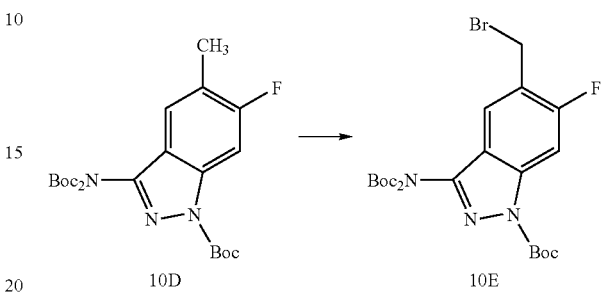

A solution of compound 10D (630.00 mg, 1.3533 mmol), N-bromosuccinimide (337.22 mg, 1.8947 mmol) and benzoyl peroxide (65.563 mg, 0.27067 mmol) in carbon tetrachloride (20 mL) was heated to reflux and allowed to stir at this temperature for 3 hours. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried (MgSO$_4$), filtered, and concentrated in vacuo. The residue obtained was purified using flash column chromatography (SiO$_2$, EtOAc/Hexanes) to provide compound 10E as a colorless oil.

Example 11

Preparation of Intermediate Compounds 11E and 11F

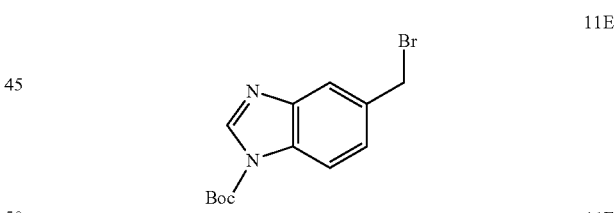

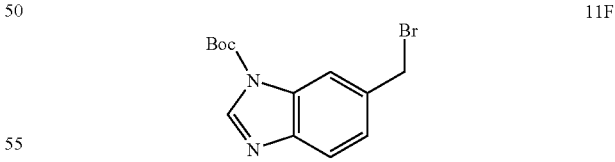

Step A—Synthesis of Compound 11B

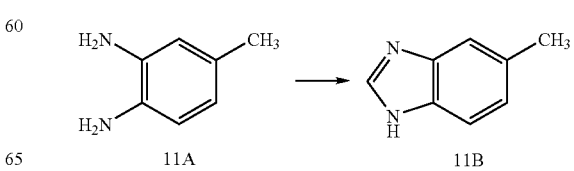

A solution of compound 11A (3 g, 24.5 mmol) in trimethyl orthoformate (15 mL) was treated with 2 drops conc. HCl and heated to 80° C. for 2 hours. The reaction mixture was cooled to room temperature and concentrated in vacuo to provide compound 11B (3.65 g), which was used without further purification. M.S. found for $C_8H_8N_2$: 133.2 $(M+H)^+$.

Step B—Synthesis of Compounds 11C and 11D

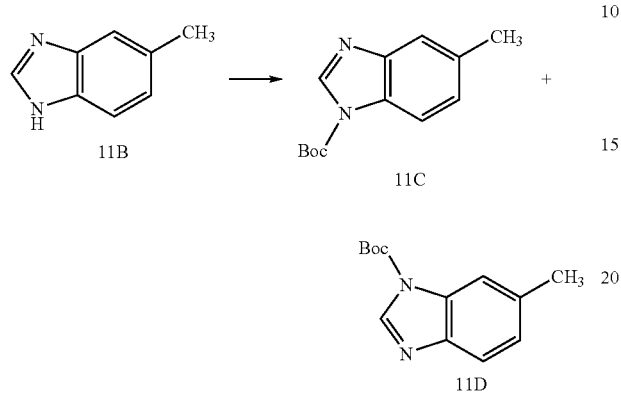

To a solution of compound 11B (24.5 mmol) in CH$_3$CN (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds 11C and 11D (5.38 g, 94.3% yield over steps A and B).

Step C—Synthesis of Compounds 11E and 11F

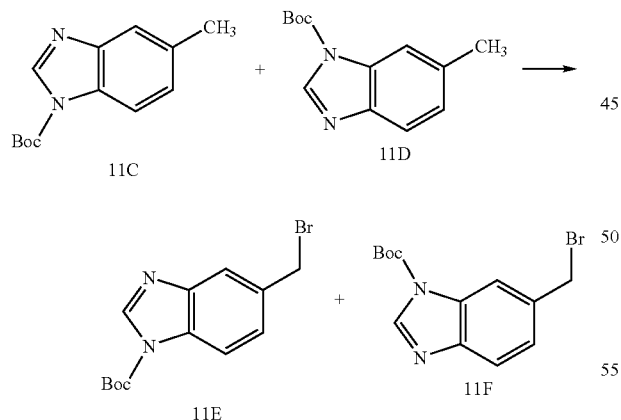

To a solution of compounds 11C and 1D (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C. and allowed to stir at this temperature for 12 hours. The reaction was cooled to room temperature, solids were filtered off and the filtrate was washed with water, dried over sodium sulfate and concentrated in vacuo to provide compounds 11E and 11F (2.58 g) which was used without further purification. M.S. found for $C_{13}H_{15}BrN_2O_2$: 334.7 $(M+Na)^+$.

Example 12

Preparation of Intermediate Compound 12B

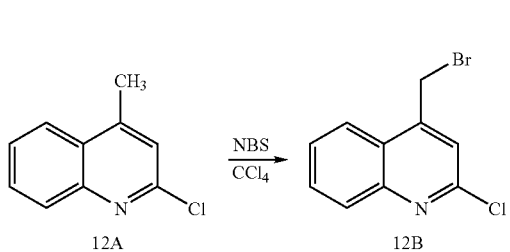

A mixture of compound 12A (1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound 12B, and was used without further purification.

Example 13

Preparation of Intermediate Compound 13D

Step A—Synthesis of Compound 13B

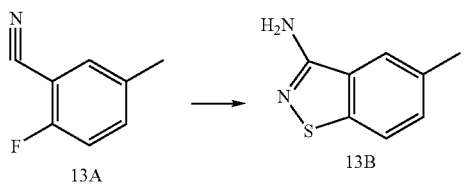

A mixture of 2-fluoro-5-methylbenzonitrile (13A, 2.0 g; 14.799 mmol) and sodium sulfide (1.0 eq, 1.15 g) was dissolved in 150 mL of DMSO and heated at 70° C. overnight. The mixture was placed in an ice-water bath and treated with concentrated aqueous ammonium hydroxide (20 mL) and aqueous sodium hypochlorite (20 mL). The reaction mixture was allowed to warm to room temperature and stirred for 5 h. The mixture was diluted with ethyl acetate (300 mL) and washed with water (2×60 mL) and brine (50 mL). The organic layer was dried over magnesium sulfate, filtered and concentrated in vacuo. The residue was adsorbed on silica gel and purified on a Biotage 40-M silica gel column (gradient: 0 to 30% acetone in hexanes) to give the product 13B (860 mg; 36%) as a white solid. $^1$H-NMR (CDCl$_3$; 400 MHz): δ 7.68 (1H, d, J=8.54 Hz), 7.48 (1H, s), 7.33 (1H, d, J=8.54 Hz), 4.89 (2H, broad s), 2.50 (3H, s).

Step B—Synthesis of Compound 13C

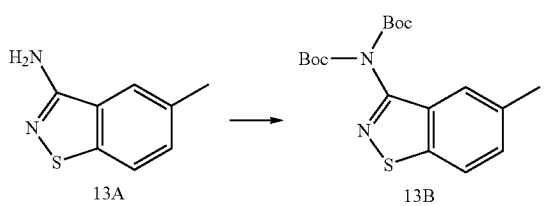

A solution of 5-methylbenzo[d]isothiazol-3-ylamine (13B, 850 mg; 5.176 mmol) in dry acetonitrile (50 mL) was treated with Boc-anhydride (2.1 eq, 2.37 g) and heated to 50° C. All starting material had been consumed after 2 h and the mixture was concentrated in vacuo to one third of its volume. The residue was dissolved in ethyl acetate (100 mL) and washed with aqueous sodium hydrogen sulfate (20 mL), and brine (20 mL). The organic layer was dried over magnesium sulfate, filtered and concentrated in vacuo. The residue was adsorbed on silica gel and purified on a Biotage 40-M silica gel column (gradient: 0 to 10% ethyl acetate in hexanes) to give the product 13C (1.7 g; 91%) as a white powder. $^1$H-NMR (CDCl$_3$; 400 MHz): δ 7.77 (1H, d, J=8.54 Hz), 7.55 (1H, s), 7.38 (1H, dd, J=1.83, 8.54 Hz), 2.51 (3H, s), 1.36 (18H, s). LR-MS (ESI): caldc for C$_{18}$H$_{25}$N$_2$O$_4$S [M+H]$^+$ 365.15; found 365.23.

Step C—Synthesis of Compound 13D

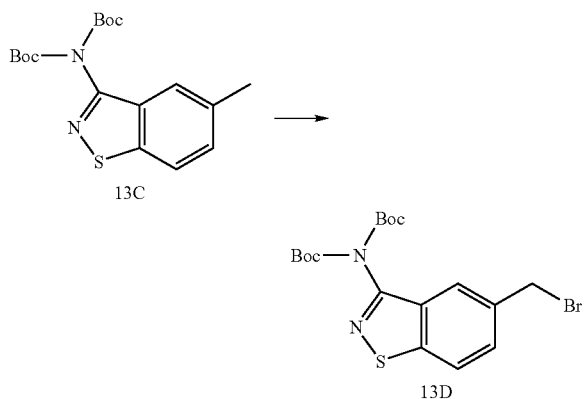

A solution of N,N-bis-Boc-5-methyl-benzo[d]isothiazol-3-ylamine (13C, 500 mg; 1.371 mmol) in 15 mL of carbon tetrachloride was treated N-bromosuccinimide (1.05 eq, 256 mg) and benzoyl peroxide (10 mol %; 33 mg). The solution was degassed (vacuum/argon flush) and then heated to 75° C. for 5 h. The reaction mixture was concentrated to one third of its volume in vacuo and the residue was dissolved in ethyl acetate (50 mL). The solution was washed with aqueous saturated sodium bicarbonate soln (2×10 mL) and brine (10 mL). The organic layer was dried over magnesium sulfate, filtered and concentrated in vacuo. The residue was adsorbed on silica gel and purified on a Biotage 40-S silica gel column (gradient: hexanes then 0 to 10% ethyl acetate in hexanes) to give the product 13D (396 mg; 69%) as a white solid. $^1$H-NMR (CDCl$_3$; 400 MHz): δ 7.87 (1H, d, J=8.54 Hz), 7.78 (1H, s), 7.58 (1H, dd, J=1.83, 8.54 Hz), 4.63 (2H, s), 1.37 (18H, s). LR-MS (ESI): caldc for C$_{18}$H$_{24}$BrN$_2$O$_4$S [M+H]$^+$ 445.06. found 445.24.

Example 14

Preparation of Intermediate Compound 14D

Step A—Synthesis of Compound 14B

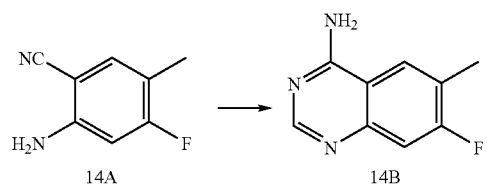

A solution of 14A (0.20 g, 1.33 mmol) in formamide (15 mL) was heated to 150° C. and stirred for 18 h. After cooled to room temperature, ethyl acetate (60 mL) and water (30 mL) were added and the layers were separated. The organic solution was washed with water (3×20 mL), dried (MgSO$_4$), filtered, and concentrated in vacuo to provide the crude product 14B (0.22 g, 93%). MS found for C$_9$H$_8$FN$_3$: 178.2 (M+H)$^+$.

Step B—Synthesis of Compound 14C

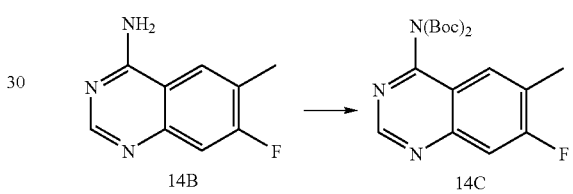

14B was treated with 3.0 equivalent of (Boc)$_2$O to afford 14C. MS found for C$_{19}$H$_{24}$FN$_3$O$_4$: 378.4 (M+H)$^+$.

Step C—Synthesis of Compound 14D

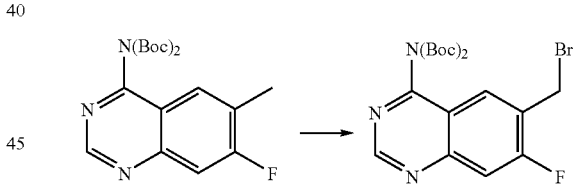

Bromination of 14C under standard N-bromo succinimide conditions afforded 14D. MS found for C$_{19}$H$_{23}$BrFN$_3$O$_4$: 458.3 (M+H)$^+$.

Example 15

Preparation of Intermediate Compound 15F

Step A—Synthesis of Compound 15B

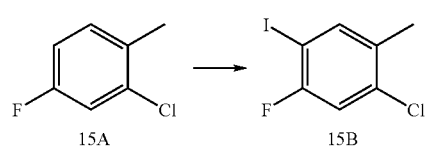

N-iodosuccinimide (1.1 eq; 17.1 g) was added to a solution of 2,4-difluoro toluene (15A, 10.0 g; 69.17 mmol; Alfa Aesar) in trifluoroacetic acid (46 mL). The reaction was set to stir for 12 h. The volatiles were removed under reduced pressure; the remaining slurry was diluted with ether (400 mL) and washed with 5% aq sodium thiosulfate (5×40 mL), water (2×30 mL), and brine (40 mL). The organic layer was collected, dried over magnesium sulfate, filtered, and concentrated under reduced pressure. The reaction was purified via bulb to bulb distillation to afford product 15B as a colorless liquid (17 g; 91%)

Step B—Synthesis of Compound 15C

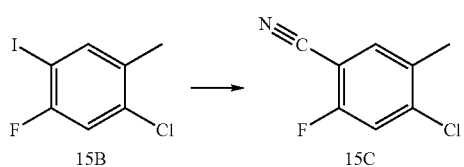

A solution of intermediate 15B (13.0 g; 48.06 mmol) and zinc cyanide (1 eq; 5.644 g) in N,N-dimethlyformamide (50 mL) was treated with tetrakis (triphenylphosphine) palladium (0) (0.1 eq; 5.55 g) and heated at 90° C. for 12 h. The reaction mixture was diluted with ether (600 mL) and ammonium hydroxide (1:1 concentrated ammonium hydroxide: water 200 mL). The organic layer was separated and washed with water (100 mL) and brine (100 mL), dried over magnesium sulfate, filtered, concentrated under reduced pressure, and purified over silica gel first eluting with hexanes, then with 20% ethyl acetate/hexanes. Product 15C (4.48 g; 33%) was afforded as a clear oil.

Step C—Synthesis of Compound 15D

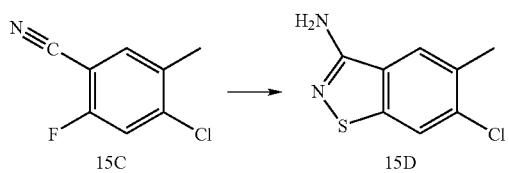

A solution of 15C (2.25 g; 13.27 mmol) and sodium sulfide (1 eq; 1.035 g) was prepared in DMSO (130 mL) and heated at 70° C. overnight. The mixture was placed in an ice water bath and treated with concentrated aqueous ammonium hydroxide (30 mL) and aqueous sodium hypochlorite (30 mL). The reaction mixture was stirred for 5 h (temp from 0 to 25° C.). The mixture was diluted with ethyl acetate (400 mL) and washed with water (2×40 mL) and brine (50 mL). The organic layer was dried over magnesium sulfate, filtered and concentrated in vacuo. The residue was adsorbed on silica gel and purified on an ISCO 330G column (gradient: 0-30% acetone in hexanes), affording product 15D (800 mg; 30.3%) as a white solid.

Step D—Synthesis of Compound 15E

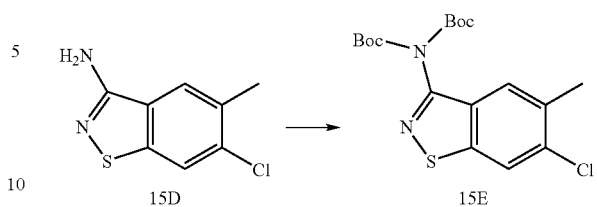

A solution of intermediate 15D (780 mg; 3.93 mmol) in dry acetonitrile (39 mL) was treated with Boc-anhydride (2.2 eq; 1.885 g) and heated to 50° C. All starting material had been consumed after 2 h and the mixture was concentrated in vacuo to one third of its volume. The residue was dissolved in ethyl acetate (100 mL) and washed with aqueous sodium hydrogen sulfate (20 mL) and brine (20 mL). The organic layer was dried over magnesium sulfate, filtered and concentrated in vacuo. The residue was adsorbed on silica gel and purified on a ISCO 80 gram column (gradient: 0 to 10% ethyl acetate in hexanes) to give the product 15E (1.03 g; 66% yield) as a white solid.

Step E—Synthesis of Compound 15F

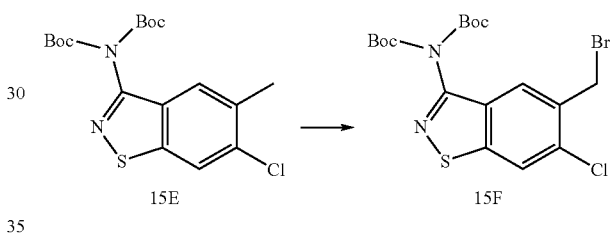

A solution of intermediate 15E (400 mg; 1.003 mmol), N-Bromosuccinimide (1.05 eq; 187.4 mg), and benzoyl peroxide (0.1 eq; 24.3 mg) in dry carbon tetrachloride (10 mL) was prepared and heated at reflux for 12 h. TLC (30% ethyl acetate in hexanes) revealed the reaction had partially progressed. The reaction mixture was concentrated under reduced pressure, diluted with ethyl acetate (100 mL), washed with saturated aqueous sodium bicarbonate (25 mL) and brine (25 mL), dried over magnesium sulfate, filtered, and concentrated under reduced pressure. The residue was then diluted with dichloromethane, adsorbed onto silica gel, and purified on ISCO (25-M Column; 0-40% ethyl acetate in hexanes). The fractions containing product were concentrated under reduced pressure affording intermediate 15F (278 mg; 58%) as a clear yellow oil.

Example 16

Preparation of Intermediate Compound 16C

Step A—Synthesis of Compound 16A

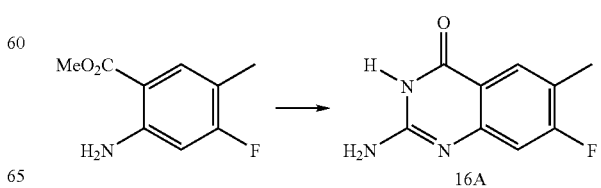

A solid mixture of methyl 2-amino-4-fluoro-5-methylbenzoate (2.66 g, 14.5 mmol), chloroformamidinium hydrochloride (2.6 g, 22.6 mmol) and methyl sulfone (8.5 g, 90.3 mmol) was heated to 150-160° C. in an oil bath with vigorous stirring. It became a clear solution after about 10 min. Heating was continued for a total of 2 h. When cooled to room temperature, it became a solid. The material was taken up with water (200 mL), basified with commercial ammonium hydroxide. After stirred for 1 h, the solid was collected through filtration. It was washed with water (20 mL) and dried under vacuum to give crude product 16A (2.93 g, quant.). MS found for $C_9H_8FN_3O$: 194.2 $(M+H)^+$.

Step B—Synthesis of Compound 16B

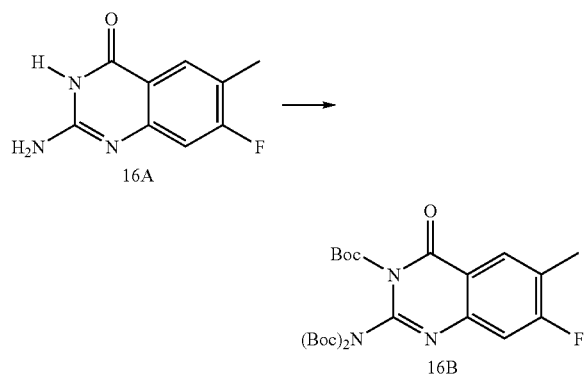

Compound 16B was prepared from 16A according to the procedures described, and using 4 equivalents of(Boc)$_2$O. MS found for $C_{24}H_{32}FN_3O_7$: 394.3 $(M+H-100)^+$.

Step C—Synthesis of Compound 16C

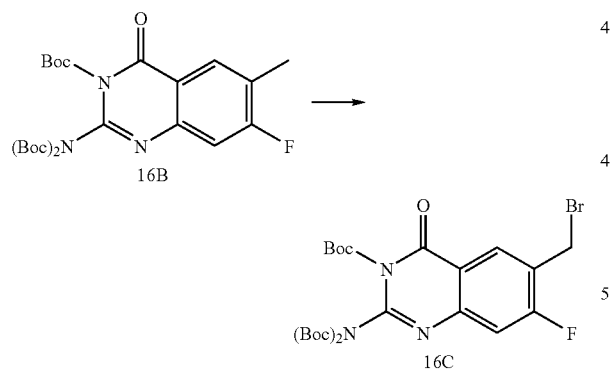

A solution of compound 16B (4.83 g, 9.8 mmol), N-bromosuccinimide (2.70 g, 15.2 mmol) and benzoyl peroxide (600 mg, 2.48 mmol) in carbon tetrachloride (300 mL) was heated to reflux and allowed to stir at this temperature for 18 h. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried (MgSO$_4$), filtered, and concentrated in vacuo to provide intermediate compound 16C, which was used without further purification. MS found for $C_{24}H_{31}BrFN_3O_7$: 472.3 $(M+H-100)^+$.

Example 17

Preparation of Intermediate Compound 17G

Step A—Synthesis of Compound 17B

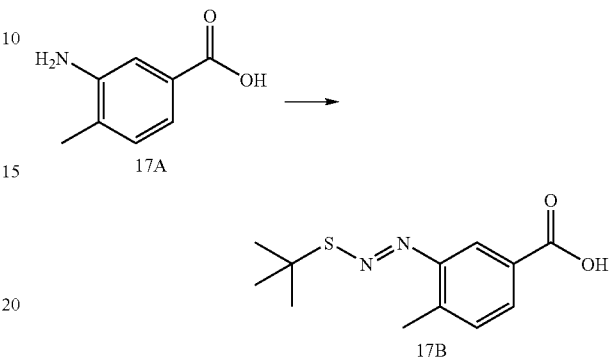

To a stirred solution of aqueous HCl (15 mL of conc HCl in 50 mL of water) was added 3-amino-4-methyl benzoic acid (17A, 5.0 g; 33.0 mmol). The mixture was cooled in an ice-water bath followed by slow addition of a solution of sodium nitrite (1.1 eq, 2.50 g) in water (12 mL). The mixture was stirred for 30 min at which point the mixture was a homogeneous dark solution. A saturated aqueous solution of sodium acetate was added until pH 6 was attained. Sodium t-butylthiolate (0.5 eq, 1.85 g) was added in one portion. The reaction was stirred for 2 h and the resulting precipitate was collected by filtration (whatman #1), washed with water (20 mL) and dried under vacuum to give the product 17B (2.7 g; 64%) as a tan solid.

Step B—Synthesis of Compound 17C

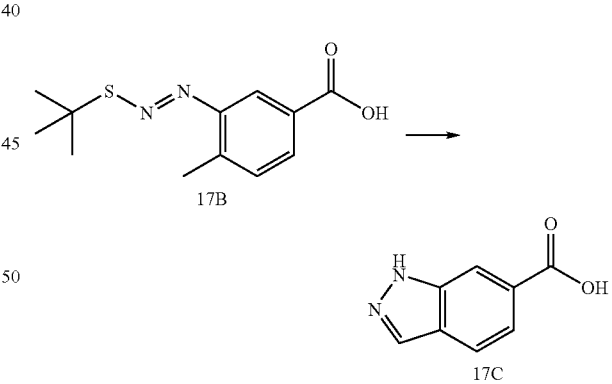

To a stirred solution of potassium tert-butoxide (10.0 eq, 12.0 g) in DMSO (50 mL) was added a solution of t-butyl-diazaenyl benzoic acid 17B (2.7 g; 10.70 mmol) in DMSO (30 mL). The mixture was stirred for 6 h and then diluted with ice and acidified with aqueous 1 M HCL until pH 5-6 was attained. The mixture was extracted with ethyl acetate (3×50 mL) and the combined organic layers were washed with water (20 mL) and brine (20 mL). The organic layer was dried over magnesium sulfate, filtered and concentrated in rotavap to give the crude product 17C as a slightly yellow solid which was used without further purification.

Step C—Synthesis of Compound 17D

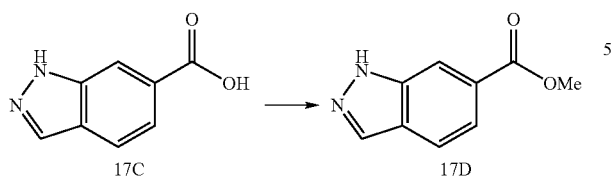

A solution of 1H-indazole-6-carboxylic acid 17C (1.73 g; 10.70 mmol) in toluene (80 mL) and methanol (30 mL) was treated with a solution of TMS-diazomethane (2 M soln in ether) until evolution of gas stopped. The reaction mixture was concentrated in vacuo and the residue was adsorbed on silica gel. The product was purified on a Biotage 40-M silica gel column (gradient: 0 to 20% acetone in hexanes) to give the product 17D (950 mg; 50% for two steps) as a slightly yellow solid. $^1$H-NMR (CDCl$_3$; 400 MHz): δ 8.28 (1H, s), 8.16 (1H, s), 7.86 (1H, d, J=8.54 Hz), 7.81 (1H, d, J=8.54 Hz), 3.98 (3H, s). LR-MS (ESI): calcd for C$_9$H$_9$N$_2$O$_2$[M+H]$^{+177.07}$. found 177.20.

Step D—Synthesis of Compound 17E

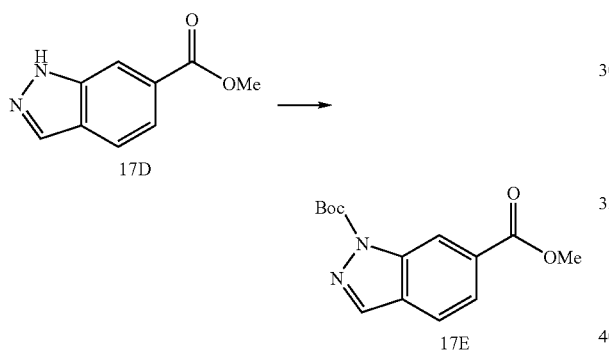

A solution of 1H-indazole-6-carboxylic acid methyl ester 17D (840 mg; 4.76 mmol) in mL of acetonitrile was treated with Boc-anhydride (1.05 eq, 1.09 g) and a catalytic amount of DMAP (tip of spatula). The mixture was stirred at 60° C. for 3 h. The mixture was concentrated to half its volume in rotavap and then diluted with ethyl acetate (100 mL) and washed with aqueous saturated sodium bicarbonate (20 mL) and brine (20 mL). The organic layer was dried over magnesium sulfate, filtered and concentrated in rotavap. The residue was purified on a Biotage 40-M silica gel column (gradient: 0 to 20% ethyl acetate in hexanes) to give the product 17E (1.2 g; 93%) as a colorless oil. $^1$H-NMR (CDCl$_3$; 400 MHz): δ 8.91 (1H, s), 8.22 (1H, s), 7.99 (1H, dd, J=1.22, 8.54 Hz), 7.78 (1H, d, J=8.54 Hz), 3.97 (3H, s), 1.74 (9H, s).

Step E—Synthesis of Compound 17F

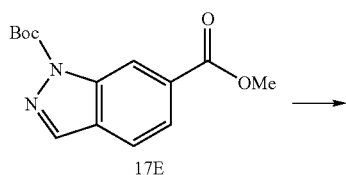

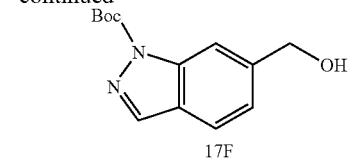

A solution of indazole 17E (460 mg; 1.66 mmol) in 16 mL of dry THF was cooled to −78° C. and treated with lithium triethylborohydride (2.5 eq, 4.15 mL of a 1 M soln in THF). The reaction mixture was stirred at −78° C. and followed by TLC (25% ethyl acetate in hexanes). The reaction was completed in about 1 h and quenched by addition of aqueous saturated sodium hydrogen sulfate (3 mL). The mixture was extracted with ethyl acetate (100 mL) and washed with water (20 mL) and brine (20 mL). The organic layer was dried over magnesium sulfate, filtered and concentrated in rotavap to give the crude product as a colorless oil. The residue was chromatographed on a Biotage 40-S silica gel column (0 to 40% ethyl acetate in hexanes) to give the following: des-Boc starting material (70 mg); alcohol product 17F (160 mg; 40%). $^1$H-NMR (CDCl$_3$; 400 MHz): δ 8.19 (1H, s), 8.13 (1H, s), 7.67 (1H, d, J=7.93 Hz), 7.30 (1H, d, J=7.93 Hz), 5.13 (2H, s), 1.71 (9H, s).

Step F—Synthesis of Compound 17G

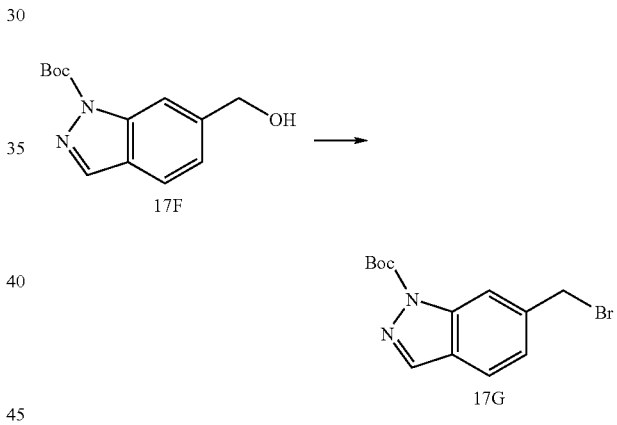

A solution of alcohol 17F (160 mg; 0.644 mmol) in dry chloroform (12 mL) was placed in an ice-water bath and treated with pyridine (4.0 eq, 0.208 mL, d 0.978) and a solution of thionyl bromide (1.2 eq, 0.060 mL, d 2.683) in 1 mL of chloroform. The ice-water bath was removed and the reaction mixture was stirred at room temp for 30 min. TLC (30% ethyl acetate in hexanes) showed about 40% conversion and more thionyl bromide was added (0.2 eq). The mixture was heated to 70° C. for 10 min. Upon cooling the mixture was diluted with ethyl acetate (30 mL) and washed with aqueous saturated sodium bicarbonate (5 mL), aqueous sodium hydrogen sulfate (5 mL) and brine (5 mL). The organic layer was dried over magnesium sulfate, filtered and concentrated in rotavap. The residue was purified on a Biotage 25-S silica gel column (gradient: 0 to 40% ethyl acetate in hexanes) to give the product 17G (76 mg; 38%) as a colorless oil along with unreacted starting material (25 mg; 24%). $^1$H-NMR (CDCl$_3$; 400 MHz): δ 8.23 (1H, s), 8.14 (1H, s), 7.72 (1H, d, J=8.54 Hz), 7.32 (1H, dd, J=1.22, 8.54 Hz), 5.21 (1H, d, J=12.20 Hz), 5.09 (1H, d, J=12.20 Hz), 1.71 (9H, s).

Example 18

Preparation of Intermediate Compound 18C

Step A—Synthesis of Compound 18B

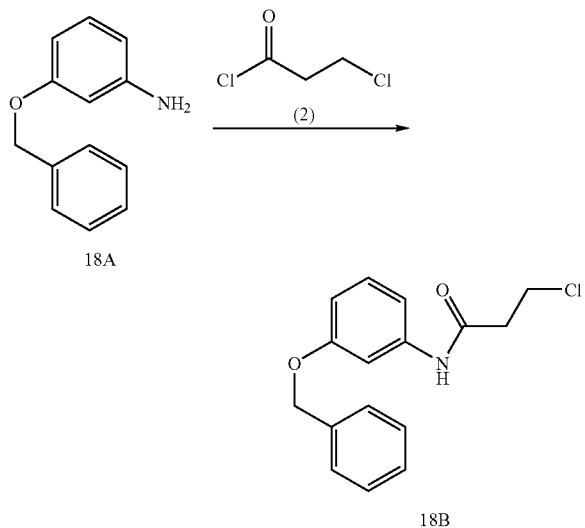

Compound 18A (commercially available) (10.0 g, 50.25 mmol) was dissolved in water at room temperature and to resulting suspension $K_2CO_3$ (3.8 g, 27.64 mmol) was added. 3-Chloro propionylchloride (7.0 g, 55.28 mmol) was added dropwise for 30 minutes and stirred for 2 hours at RT. The precipitate was filtered and washed with water, 1 N HCl, dried at 50° C. under vacuum overnight to give 7.2 g of the product 18B.

Step B—Synthesis of Compound 18C

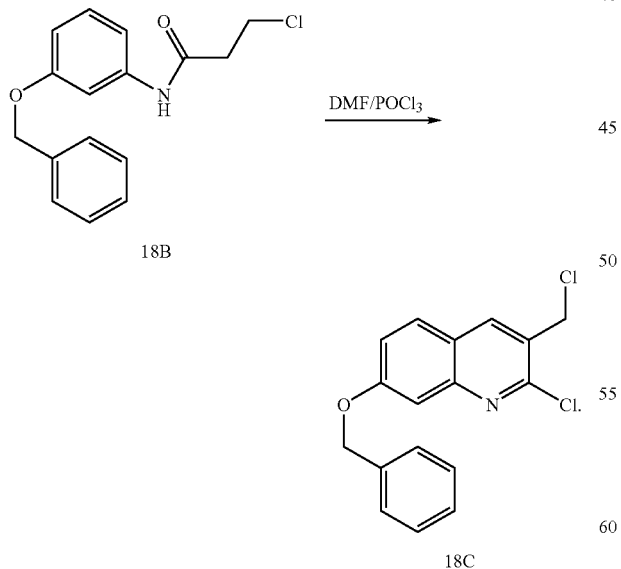

To N,N-Dimethylformamide (3.6 g, 49.66 mmol) at 0° C. was added drop wise $POCl_3$ (26.6 g, 173.8 mmol) and stirred for 60 minutes, white precipitate was formed. The 7.2 g of the compound 18B was added by portion in reaction mixture and stirred for 24 hours at room temperature. Reaction mixture was diluted with ethyl acetate and slowly added to a beaker with ice, after ice was melted, organic layer was separated and washed with 0.5 N NaOH and water, brine, dried over sodium sulfate, and concentrated in vacuum, purified using flash chromatography, to provide compound 18C (5.5 g, 34% after two steps). M.S. found: 318.04 $(M+H)^+$.

Example 19

Preparation of Intermediate Compound 19E

Step A—Synthesis of Compound 19B

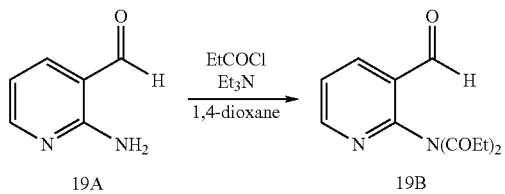

To a solution of 19A (7.2 g, 58.8 mmol) in 1,4-dioxane (39 mL) at 0° C. was added propionyl chloride (15.8 ml, 176.5 mmol) and $Et_3N$ (24.6 mL, 176.5 mmol) with stirring. The reaction mixture was stirred at room temperature for overnight. The solvent was removed under reduced pressure, and the resulting residue was taken up in EtOAc. The organic phase was washed with water, dried over $MgSO_4$, filtered, and concentrated in vacuo to give a crude residue of 19B.

Step B—Synthesis of Compound 19C

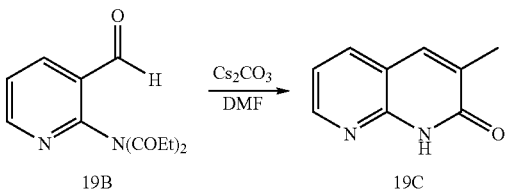

To a suspension of 19B (crude residue from above) in DMF (60 mL) was added cesium carbonate (38 g, 117.6 mmol), and the resulting mixture was heated at 65° C. for overnight. Reaction was cooled to room temperature, and the bulk of DMF was removed under reduced pressure. Water was then added to the crude residue and the mixture was filtered. The filter-cake was washed with water and EtOAc. 5.2 g of 19C was collected as a pale yellow solid.

Step C—Synthesis of Compound 19D

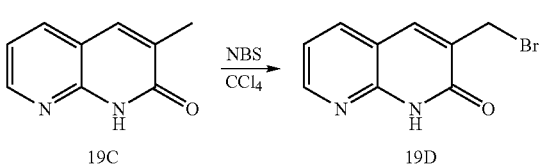

To a suspension of 19C (0.8 g, 5 mmol) in $CCl_4$ (25 mL) was added NBS (38 g, 117.6 mmol), and benzoyl peroxide (61 mg, 0.25 mmol), and the resulting mixture was then heated at 90° C. for 4 hours. Cooled the reaction to room temperature, and 300 mL of $CH_2Cl_2$ was added. The mixture was filtered, and filtrate was dried over MgSO₄, filtered, and concentrated in vacuo to give 2 g of crude residue of 19D.

Step D—Synthesis of Compound 19E

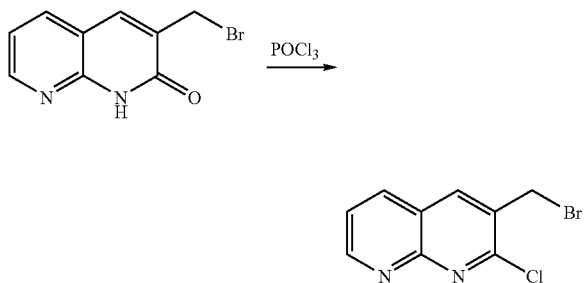

POCl₃ was added to a 100 mL round bottom flask containing crude 19D. The resulting suspension was then heated at 88° C. for 4 hours. Cooled the reaction to room temperature, and then poured into a 1 liter beaker containing ice. The resulting solution was neutralized to ph 8 using 6 NNaOH solution. Solid that precipitated from the solution was collected to give 0.82 g of crude residue which was purified using column chromatography on silica gel (ISCO Combi-Flash Rf; gradient: 5 to 50% ethyl acetate in hexanes) to provide 330 mg of compound 19E.

Example 20

Preparation of Intermediate Compound 20D

Step A—Synthesis of Compound 20B

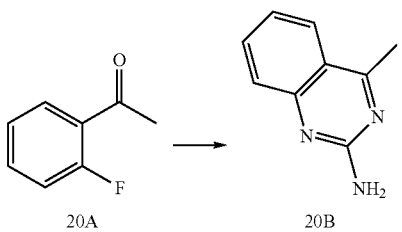

A mixture of ortho-fluoroacetophenone (20A, 3.45 g; 25 mmol) and guanidine carbonate (2 eq; 9.0 g) was prepared in 250 mL of N,N-dimethyl acetamide, set to stir, and heated at 135° C. under nitrogen purge overnight. The solvent was removed under reduced pressure and diluted with ethyl acetate (600 mL). The solution was washed with water (2×100 mL) and brine (40 mL). The organic layer was separated, dried over magnesium sulfate, filtered, and concentrated under reduced pressure. The solid was dissolved in methylene dichloride, loaded on silica gel and dried under reduced pressure. The material was purified on ISCO (80 g column; 0-70% THF in Hexanes). Fractions containing product were collected and concentrated under reduced pressure to afford product 20B as a crème colored solid (880 mg; 22%)

Step B—Synthesis of Compound 20C

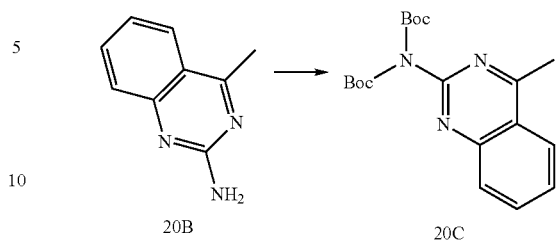

A solution of 4-Methyl-quinazolin-2-ylamine 20B (640 mg; 4.02 mmol) in 10 mL of dry acetonitrile was treated with a solution of Boc-anhydride (2.5 eq; 2.19 g) in 10.0 mL of dry acetonitrile. The resulting solution was treated with DMAP (0.2 eq; 98.2 mg). The mixture was set to stir overnight. TLC (50% THF in hexanes) showed a complete reaction. The mixture was diluted with ethyl acetate (500 mL) and washed with water (3×30 mL), and Brine (40 mL). The organic layer was dried over magnesium sulfate, filtered and concentrated in rotavap. The residue was adsorbed on silica gel and purified on an ISCO column (120 g) (0% to 60% THF in hexanes). The fractions with product were collected and concentrated under reduced pressure to afford product 20C as a light yellow-white solid (1.3 g; 90%).

Step C—Synthesis of Compound 20D

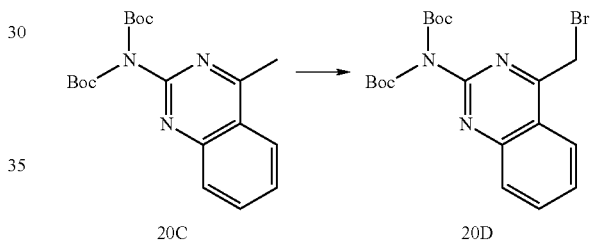

Intermediate 20C (1.11 g; 3.09 mmol), N-Bromosuccinimide (1.05 eq; 577 mg), and benzoyl peroxide (0.1 eq; 75 mg) were combined in round bottom and diluted with dry carbon tetrachloride (31 mL). The reaction was stirred at room temperature for 10 minutes and then heated at reflux overnight. TLC (30% ethyl acetate in hexanes) revealed the reaction has partially progressed. The reaction mixture was concentrated under reduced pressure, diluted with ethyl acetate (300 mL), and washed with sat. aqueous sodium bicarbonate (40 mL) and brine (40 mL), dried over magnesium sulfate, filtered, concentrated under reduced pressure, diluted with methylene dichloride, adsorbed onto silica gel, and purified on ISCO (25-M Column; 0-40% ethyl acetate in hexanes). The fractions containing product were concentrated under reduced pressure and afforded product as a clear oil in a 2:1 mixture of pure product 20D and starting material (Total: 440 mg; 33%).

Example 21

Preparation of Intermediate Compound 21C

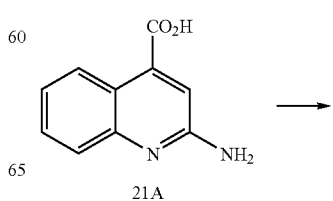

-continued

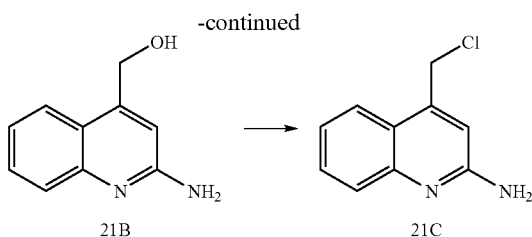

The starting materials 21A (2.0 g, 10.6 mmol), lithium aluminum hydride (2.0 g, 52.7 mmol), and THF (100 ml) were added to a 250 ml round-bottomed flask. The resulting suspension was stirred at room temperature for 18 hours. The reaction was quenched with 10 ml of saturated ammonium chloride solution followed by 200 ml of ethyl acetate. After filtration, the organic layer was washed with brine (2×100 ml), dried over sodium sulfate, and concentrated under vacuum to provide 21B as a yellowish solid (1.05 g, 59%).

A 250 ml round-bottomed flask was charged with 21B (1.05 g, 6.03 mmol) and thionyl chloride (10 ml). The resulting mixture was stirred at 60° C. for 4 hours before cooled to room temperature. After removal of excess of thionyl chloride, the residue was dried under vacuum to afford 21C as an orange solid (1.45 g). This crude material was used without further purification.

Example 22

Preparation of Intermediate Compound 22G

Step A—Synthesis of Compound 2B

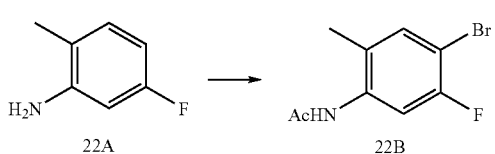

A solution of 5-fluoro-2-methylaniline (22A, 25 g, 200 mmol) in toluene (250 mL) was treated with acetic anhydride (25 mL. 226 mmol) heated at reflux for 1 h. The reaction mixture was cooled when a colorless solid precipitated out which was filtered and washed with a mixture of ether and hexanes. The colorless solid was taken in acetic acid (150 mL) and treated dropwise with a solution of bromine (9.6 mL, 186 mmol) in acetic acid (20 mL) and stirred at rt. for 12 h. The solution was diluted with water and the solid separating out was filtered and washed to yield N-(4-bromo-5-fluoro-2-methylphenyl)acetamide (22B, 40 g) as a colorless solid.

Step B—Synthesis of Compound 22C

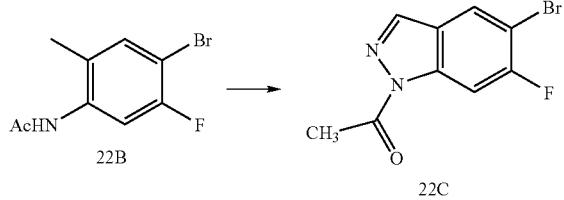

A solution of N-(4-bromo-5-fluoro-2-methylphenyl)acetamide (22B, 10.00 g, 40.64 mmol) in chloroform (100 mL) was treated with acetic anhydride (11.5 mL, 122.0 mmol), potassium acetate (8.00 g, 81.5 mmol), and 18-Crown-6 (540.00 mg, 2.0430 mmol) and then with isoamyl nitrite (12.3 mL, 871 mmol) and heated at 65° C. for 12 h. The reaction mixture was cooled to room temperature and treated with EtOAc (500 mL), washed with water, dried (MgSO$_4$), filtered, and then concentrated in vacuo. A pale yellow solid of 1-(5-bromo-6-fluoro-1H-indazol-1-yl)ethanone (22C) precipitated out. The initial filtrate was concentrated and the residue was purified by chromatography (SiO$_2$, EtOAc/Hexanes) to yield more of product 22C.

Step C—Synthesis of Compound 22D

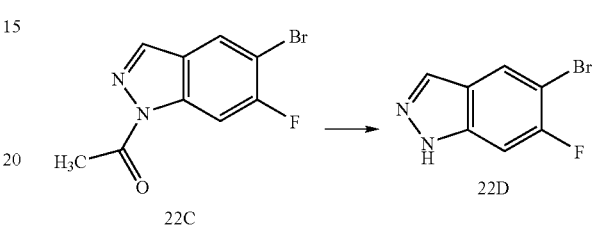

A solution of 1-(5-bromo-6-fluoro-1H-indazol-1-yl)ethanone (2C, 5.0 g, 19.5 mmol) was treated with aq HCl (3M soln., 100 mL) and methanol (20 mL) and heated at 90° C. for 3 h, when the reaction turns homogenous. The reaction mixture was cooled to room temperature and basified with aq. NaOH. A colorless solid precipitated out which was filtered and dried to yield 5-bromo-6-fluoro-1H-indazole (22D)

Step D—Synthesis of Compound 22E

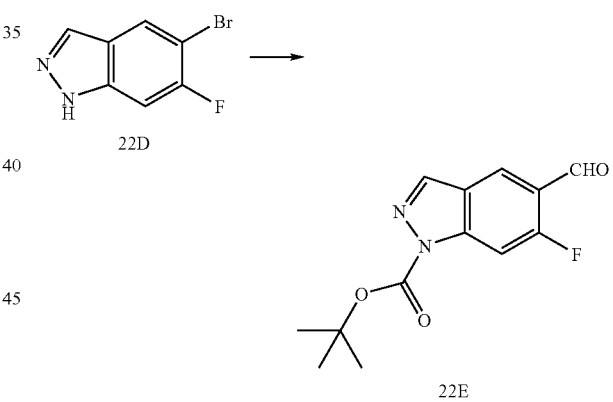

A solution of 5-bromo-6-fluoro-1H-indazole (22D, 3.50 g, 16.28 mmol) in tetrahydrofuran (200.00 mL) was treated with sodium hydride (60% in mineral oil, 1.172 g) at 0° C. and stirred at rt. for 20 min. The reaction mixture was cooled to −78° C. (dry ice and acetone) and treated with 2.5 M of n-butyl lithium in hexane (8.2 mL, 20.3 mmol) dropwise. The reaction mixture was stirred at that temperature for 20 min and treated with DMF (5.06 mL, 65.11 mmol). The reaction mixture was slowly warmed to room temperature when the viscous solution turn fluidic and stirring was efficient. Analysis of TLC (40% EtOAc/Hexanes) indicated complete conversion of starting material to product. The reaction mixture was acidified with aq. HCl taken up in EtOAc (500 mL) washed with aq. HCl (100 mL), brine (100 mL), dried (MgSO$_4$), filtered, concentrated in vacuo and used as it is in next step. A solution of product 6-fluoro-1H-indazole-5-carbaldehyde (2.3 g) in THF (100 mL) was treated with di-tertbutyldicarbonate (3.56 g, 16.28 mmol) and DMAP (300 mg) and stirred at room temperature for 3 h. The reaction mixture was concentrated in vacuo and the residue was purified by chromatography (SiO$_2$, EtOAc/Hexanes gradient 0-40%) to yield [2e]tert-butyl 6-fluoro-5-formyl-1H-indazole-1-carboxylate (22E, 3.5 g; Yield=81%) as a colorless solid.

Step E—Synthesis of Compound 22F

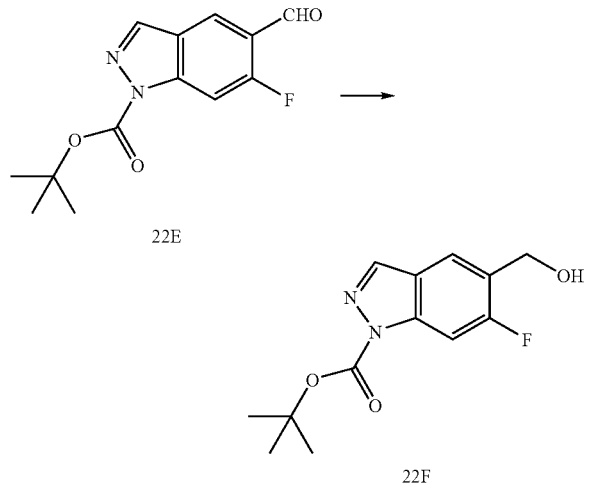

A solution of tert-butyl 6-fluoro-5-formyl-1H-indazole-1-carboxylate (22E, 3.55 g, 13.4 mmol) in methanol (50.00 mL) was treated with NaBH$_4$ (1.02 g, 26.9 mmol) at 0° C. and stirred for 1 h. The reaction mixture was diluted with water and EtOAc (500 mL). The organic layer was separated and washed with aq. HCl (1M, 200 mL), aq. NaOH (1M, 200 mL) brine (200 mL) dried (MgSO$_4$), filtered, concentrated in vacuo and residue was purified by chromatography (SiO$_2$, EtOAc/hexanes) to yield tert-butyl 5-(hydroxymethyl)-6-fluoro-1H-indazole-1-carboxylate (22F, 3.00 g; Yield=83.9%) as a colorless solid.

Step F—Synthesis of Compound 22G

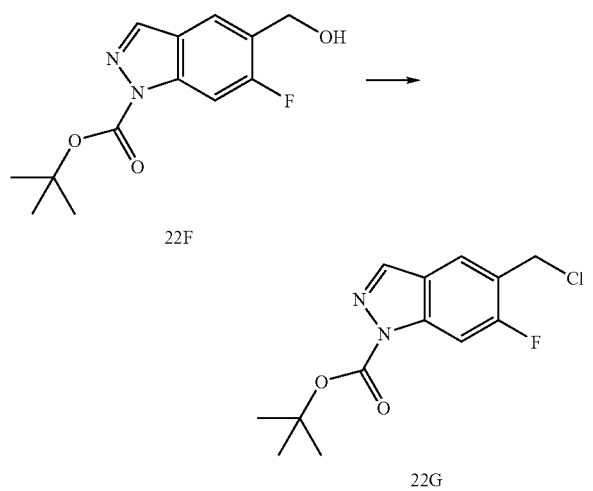

A solution of tert-butyl 5-(hydroxymethyl)-6-fluoro-1H-indazole-1-carboxylate (22F, 3.0 g, 11.27 mmol) in methylene chloride (50.00 mL, 780.0 mmol) at rt. was treated with pyridine (4.56 mL, 56.33 mmol) and methanesulfonyl chloride (1.31 mL) and stirred at rt. for 16 h. The reaction mixture was concentrated in vacuo and the residue was dissolved in EtOAc (300 mL) washed with aq HCl (100 mL), brine (100 mL), dried (MgSO$_4$), filtered, concentrated in vacuo, and purified by chromatography (SiO$_2$, EtOAc/Hexanes) to yield tert-butyl 5-(chloromethyl)-6-fluoro-1H-indazole-1-carboxylate (22G, 1.9 g; Yield=59%)

Example 23

HCV NS5B Polymerase Inhibition Assay

An in vitro transcribed heteropolymeric RNA known as D-RNA or DCoH has been shown to be an efficient template for HCV NS5B polymerase (S.-E. Behrens et al., EMBO J. 15: 12-22 (1996); WO 96/37619). A chemically synthesized 75-mer version, designated DCoH75, whose sequence matches the 3'-end of D-RNA, and DCoH75ddC, where the 3'-terminal cytidine of DCoH75 is replaced by dideoxycytidine, were used for assaying the NS5B enzyme activity as described in Ferrari et al., 12$^{th}$ International Symposium on HCV and Related Viruses, P-306 (2005). A soluble C-terminal 21-amino acid truncated NS5B enzyme form (NS5BDeltaCT21) was produced and purified from Escherichia coli as C-terminal polyhistidine-tagged fusion protein as described in Ferrari et al., J. Virol. 73:1649-1654 (1999). A typical assay contained 20 mM Hepes pH 7.3, 10 mM MgCl$_2$, 60 mM NaCl, 100 µg/ml BSA, 20 units/ml RNasin, 7.5 mM DTT, 0.1 µM ATP/GTP/UTP, 0.026 µM CTP, 0.25 mM GAU, 0.03 µM RNA template, 20 µCi/ml [$^{33}$P]-CTP, 2% DMSO, and 30 or 150 nM NS5B enzyme. Reactions were incubated at 22° C. for 2 hours, then stopped by adding 150 mM EDTA, washed in DE81 filter plate in 0.5M di-basic sodium phosphate buffer, pH 7.0, and counted using Packard TopCount after the addition of scintillation cocktail. Polynucleotide synthesis was monitored by the incorporation of radiolabeled CTP. The effect of the 2,3-Substituted Azaindole Derivatives on the polymerase activity was evaluated by adding various concentrations of a 2,3-Substituted Azaindole Derivative, typically in 10 serial 2-fold dilutions, to the assay mixture. The starting concentrations of the indole derivatives ranged from 200 µM to 1 µM. An IC$_{50}$ value for the inhibitor, defined as the compound concentration that provides 50% inhibition of polymerase activity, was determined by fitting the cpm data to the Hill equation $Y=100/(1+10^{((Log\ IC50-X)*HillSlope)})$, where X is the logarithm of compound concentration, and Y is the % inhibition. Ferrari et al., 12$^{th}$ International Symposium on HCV and Related Viruses, P-306 (2005) described in detail this assay procedure. It should be noted that such an assay as described is exemplary and not intended to limit the scope of the invention. The skilled practitioner can appreciate that modifications including but not limited to RNA template, primer, nucleotides, NS5B polymerase form, buffer composition, can be made to develop similar assays that yield the same result for the efficacy of the compounds and compositions described in the invention.

NS5B polymerase inhibition data for selected 2,3-Substituted Azaindole Derivatives of the present invention was obtained using the above method and calculated IC$_{50}$ values ranged from 0.001 µM to 1 µM.

Example 24

Cell-Based HCV Replicon Assay

To measure cell-based anti-HCV activity of the a 2,3-Substituted Azaindole Derivative, replicon cells were seeded at 5000 cells/well in 96-well collagen I-coated Nunc plates in the presence of the 2,3-Substituted Azaindole Derivative. Various concentrations of a 2,3-Substituted Azaindole Derivative, typically in 10 serial 2-fold dilutions, were added to the assay mixture, the starting concentration of the compound ranging from 250 uM to 1 uM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA; 5B.2R, TTGATGGGCAGCT-TGGTTTC; the probe sequence was FAM-labeled CACGC-CATGCGCTGCGG. GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 min. The ACT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV Replicon assay data for selected 2,3-Substituted Azaindole Derivatives of the present invention was obtained using the above method and calculated $EC_{50}$ values ranged from 0.001 μM to 1 μM.

Uses of the 2,3-Substituted Azaindole Derivatives

The 2,3-Substituted Azaindole Derivatives are useful in human and veterinary medicine for treating or preventing a viral infection or a virus-related disorder in a patient. In accordance with the invention, the 2,3-Substituted Azaindole Derivatives can be administered to a patient in need of treatment or prevention of a viral infection or a virus-related disorder.

Accordingly, in one embodiment, the invention provides methods for treating a viral infection in a patient comprising administering to the patient an effective amount of at least one 2,3-Substituted Azaindole Derivative or a pharmaceutically acceptable salt, solvate, ester or prodrug thereof. In another embodiment, the invention provides methods for treating a virus-related disorder in a patient comprising administering to the patient an effective amount of at least one 2,3-Substituted Azaindole Derivative or a pharmaceutically acceptable salt, solvate, ester or prodrug thereof.

Treatment or Prevention of a Viral Infection

The 2,3-Substituted Azaindole Derivatives can be used to treat or prevent a viral infection. In one embodiment, the 2,3-Substituted Azaindole Derivatives can be inhibitors of viral replication. In a specific embodiment, the 2,3-Substituted Azaindole Derivatives can be inhibitors of HCV replication. Accordingly, the 2,3-Substituted Azaindole Derivatives are useful for treating viral diseases and disorders related to the activity of a virus, such as HCV polymerase.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2): 192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Treatment or Prevention of a Virus-Related Disorder

The 2,3-Substituted Azaindole Derivatives can be used to treat or prevent a virus-related disorder. Accordingly, the 2,3-Substituted Azaindole Derivatives are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The 2,3-Substituted Azaindole Derivatives are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one 2,3-Substituted Azaindole Derivative or a pharmaceutically acceptable salt, solvate, ester or prodrug thereof.

Treatment or Prevention of a Disorder Related to HCV Infection

The 2,3-Substituted Azaindole Derivatives can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one 2,3-Substituted Azaindole Derivative, or a pharmaceutically acceptable salt, solvate, ester or prodrug thereof.

Combination Therapy

In another embodiment, the present methods for treating or preventing a viral infection can further comprise the administration of one or more additional therapeutic agents which are not 2,3-Substituted Azaindole Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one 2,3-Substituted Azaindole Derivative, or a pharmaceutically acceptable salt, solvate, ester or prodrug thereof, and (ii) at least one other antiviral agent that is other than a 2,3-Substituted Azaindole Derivative, wherein the amounts administered are together effective to treat or prevent a viral infection.

When administering a combination therapy of the invention to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 2,3-Substituted Azaindole Derivative and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In one embodiment, the at least one 2,3-Substituted Azaindole Derivative is administered during at time when the additional antiviral agent(s) exert their prophylactic or therapeutic effect, or vice versa.

In another embodiment, the at least one 2,3-Substituted Azaindole Derivative and the additional antiviral agent(s) are administered in doses commonly employed when such agents are used as monotherapy for treating a viral infection.

In another embodiment, the at least one 2,3-Substituted Azaindole Derivative and the additional antiviral agent(s) are administered in doses lower than the doses commonly employed when such agents are used as monotherapy for treating a viral infection.

In still another embodiment, the at least one 2,3-Substituted Azaindole Derivative and the additional antiviral agent (s) act synergistically and are administered in doses lower than the doses commonly employed when such agents are used as monotherapy for treating a viral infection.

In one embodiment, the at least one 2,3-Substituted Azaindole Derivative and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one 2,3-Substituted Azaindole Derivative and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one 2,3-Substituted Azaindole Derivative and the additional antiviral agent(s) may inhibit the resistance of a viral infection to these agents.

Non-limiting examples of other therapeutic agents useful in the present compositions and methods include an HCV polymerase inhibitor, an interferon, a viral replication inhibitor, an antisense agent, a therapeutic vaccine, a viral protease inhibitor, a virion production inhibitor, an antibody therapy (monoclonal or polyclonal), and any agent useful for treating an RNA-dependent polymerase-related disorder.

In one embodiment, the other antiviral agent is a viral protease inhibitor.

In another embodiment, the other antiviral agent is an HCV protease inhibitor.

In another embodiment, the other antiviral agent is an interferon.

In still another embodiment, the other antiviral agent is a viral replication inhibitor.

In another embodiment, the other antiviral agent is an antisense agent.

In another embodiment, the other antiviral agent is a therapeutic vaccine.

In a further embodiment, the other antiviral agent is an virion production inhibitor.

In another embodiment, the other antiviral agent is antibody therapy.

In another embodiment, the other antiviral agents comprise a protease inhibitor and a polymerase inhibitor.

In still another embodiment, the other antiviral agents comprise a protease inhibitor and an immunosuppressive agent.

In yet another embodiment, the other antiviral agents comprise a polymerase inhibitor and an immunosuppressive agent.

In a further embodiment, the other antiviral agents comprise a protease inhibitor, a polymerase inhibitor and an immunosuppressive agent.

In another embodiment the other agent is ribavirin.

HCV polymerase inhibitors useful in the present methods and compositions include, but are not limited to VP-19744 (Wyeth/ViroPharma), HCV-796 (Wyeth/ViroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development,* 7(4):446 (2004); Tan et al., *Nature Reviews,* 1:867 (2002); and Beaulieu et al., *Current Opinion in Investigational Drugs,* 5:838 (2004).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, Calif.).

Antibody therapy agents useful in the present methods and compositions include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but are not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (InterMune/Roche)), amprenavir, atazanavir, fosemprenavir, indinavir, lopinavir, ritonavir, nelfinavir, saquinavir, tipranavir and TMC114.

Viral replication inhibitors useful in the present methods and compositions include, but are not limited to, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhibitors useful in the present methods include, but are not limited to, an HCV protease inhibitor and a NS-3 serine protease inhibitor.

Examples of HCV protease inhibitors useful in the present methods include, but are not limited to, those disclosed in Landro et al., *Biochemistry*, 36(31):9340-9348 (1997); Ingallinella et al., *Biochemistry*, 37(25):8906-8914 (1998); Llinas-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); and
International Publication Nos. WO 98/14181; WO 98/17679, WO 98/17679, WO 98/22496 and WO 99/07734.

Further examples of protease inhibitors useful in the present methods include, but are not limited to, Additional examples of other therapeutic agents useful in the present methods include, but are not limited to, Levovirin™ (ICN Pharmaceuticals, Costa Mesa, Calif.), VP 50406™ (Viropharma, Incorporated, Exton, Pa.), ISIS14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SciClone Pharmaceuticals, San Mateo, Calif.), Maxamine™ (Maxim Pharmaceuticals, San Diego, Calif.), NKB-122 (JenKen Bioscience Inc., North Carolina), mycophenolate mofetil (Hoffman-LaRoche, Nutley, N.J.).

The doses and dosage regimen of the other agents used in the combination therapies of the present invention for the treatment or prevention of a viral infection can be determined by the attending clinician, taking into consideration the approved doses and dosage regimen in the package insert; the age, sex and general health of the patient; and the type and severity of the viral infection or related disease or disorder. When administered in combination, the 2,3-Substituted Azaindole Derivative (s) and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one 2,3-Substituted Azaindole Derivative and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU (12 mcg)/0.5 mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A inteferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the other therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the 2,3-Substituted Azaindole Derivatives are useful in veterinary and human medicine. As described above, the 2,3-Substituted Azaindole Derivatives are useful for treating or preventing a viral infection or a virus-related disorder in a patient in need thereof.

When administered to a patient, the IDs can be administered as a component of a composition that comprises a pharmaceutically acceptable carrier or vehicle. The present invention provides pharmaceutical compositions comprising an effective amount of at least one 2,3-Substituted Azaindole Derivative and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The 2,3-Substituted Azaindole Derivatives of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 2,3-Substituted Azaindole Derivatives are administered orally.

In another embodiment, the one or more 2,3-Substituted Azaindole Derivatives are administered intravenously.

In another embodiment, the one or more 2,3-Substituted Azaindole Derivatives are administered topically.

In still another embodiment, the one or more 2,3-Substituted Azaindole Derivatives are administered sublingually.

In one embodiment, a pharmaceutical preparation comprising at least one 2,3-Substituted Azaindole Derivative is in unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the 2,3-Substituted Azaindole Derivative(s) by weight or volume. In various embodiments, the present compositions can contain, in one embodiment, from about 1% to about 70% or from about 5% to about 60% of the 2,3-Substituted Azaindole Derivative(s) by weight or volume.

The quantity of 2,3-Substituted Azaindole Derivative in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion.

In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 2,3-Substituted Azaindole Derivatives will be regulated according to the judgment of the attending clinician considering such factors as age, condition and size of the patient as well as severity of the symptoms being treated. Generally, a total daily dosage of the 2,3-Substituted Azaindole Derivatives range from about 0.1 to about 2000 mg per day, although variations will necessarily occur depending on the target of the therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 2,3-Substituted Azaindole Derivative or a pharmaceutically acceptable salt, solvate, ester or prodrug thereof; (ii) one or more additional therapeutic agents that are not a 2,3-Substituted Azaindole Derivative; and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one 2,3-Substituted Azaindole Derivative, or a pharmaceutically acceptable salt, solvate, ester or prodrug of said compound and a pharmaceutically acceptable carrier, vehicle or diluent.

In another aspect the present invention provides a kit comprising an amount of at least one 2,3-Substituted Azaindole Derivative, or a pharmaceutically acceptable salt, solvate, ester or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

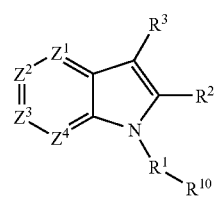

(I)

or a pharmaceutically acceptable salt or ester thereof, wherein:
$Z^1$ is —N—, —N(O)— or —C($R^4$)—;
$Z^2$ is —N—, —N(O)— or —C($R^5$)—;
$Z^3$ is —N—, —N(O)— or —C($R^6$)—;
$Z^4$ is —N—, —N(O)— or —C($R^7$)—, wherein one of $Z^1$, $Z^2$, $Z^3$, and $Z^4$ is —N— and the others are not —N— or —N(O)—;
$R^1$ is —[C($R^{12}$)$_2$]$_r$;
$R^2$ is —[C($R^{12}$)$_2$]$_q$—C(O)N($R^9$)SO$R^{11}$, —[C($R^{12}$)$_2$]$_q$—C(O)N(R)SO$_2R^{11}$, —[C($R^{12}$)$_2$]$_q$—C(O)N($R^9$)SO$_2$N($R^{11}$)$_2$,

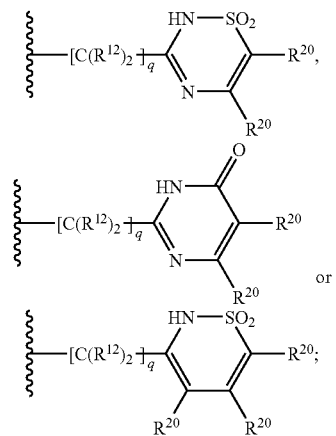

$R^3$ is:

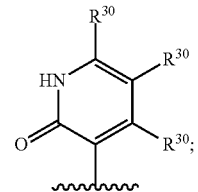

$R^4$, $R^5$, $R^6$ and $R^7$ are each, independently, H, alkyl, alkenyl, alkynyl, aryl, —[C($R^{12}$)$_2$]$_q$cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$hydroxyalkyl, halo, hydroxy, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—NR$^8$C(O)N($R^9$)$_2$, —[C($R^{12}$)$_2$]$_q$—NHSO$_2R^{11}$, —[C($R^{12}$)$_2$]$_q$—S(O)$_pR^{11}$, —[C($R^{12}$)$_2$]$_q$—SO$_2$N($R^9$)$_2$ or —SO$_2$N($R^9$)C(O)N($R^9$)$_2$;

each occurrence of $R^8$ is independently H, alkyl, alkenyl, alkynyl, —[C($R^{12}$)$_2$]$_q$-aryl, —[C($R^{12}$)$_2$]$_q$cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

each occurrence of $R^9$ is independently H, alkyl, alkenyl, alkynyl, —[C($R^{12}$)$_2$]$_q$-aryl, —[C($R^{12}$)$_2$]$_q$cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

$R^{10}$ is aryl or heteroaryl, wherein an aryl or heteroaryl group can be optionally and independently substituted with up to 4 substituents, which are each independently selected from alkyl, alkenyl, alkynyl, aryl, —[C($R^{12}$)$_2$]$_q$-cycloalkyl, —[C($R^{12}$)$_2$]$_q$-cycloalkenyl, —[C (R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

each occurrence of R$^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$-cycloalkyl, —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group;

each occurrence of R$^{30}$ is independently H, alkyl, alkenyl, alkynyl, aryl, —[C(R$^{12}$)$_2$]$_q$cycloalkyl, —[C(R$^{12}$)$_2$]$_q$cycloalkenyl, —[C(R$^{12}$)$_2$]$_q$heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$—[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$, or two adjacent R$^{30}$ groups, together with the carbon atoms to which they are attached, join to form a –3- to 7-membered ring selected from aryl, cycloalkyl, heteroaryl and heterocycloalkyl;

each occurrence of p is independently 0, 1 or 2;

each occurrence of q is independently an integer ranging from 0 to 4; and each occurrence of r is independently an integer ranging from 1 to 4.

2. The compound of claim 1, wherein R$^2$ is —C(O)N(R$^9$)SOR$^{11}$, —C(O)N(R$^9$)SO$_2$R$^{11}$, —C(O)N(R$^9$)SO$_2$N(R$^{11}$)$_2$ or

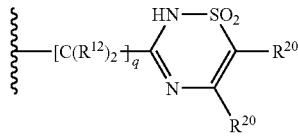

wherein R$^9$ is H, alkyl, aryl, cycloalkyl, heteroaryl or heterocycloalkyl and two R$^{20}$ groups join to form an aryl ring.

3. The compound of claim 2, wherein R$^1$ is —CH$_2$—, —CH$_2$CH$_2$—, —CH(CH$_3$)— or

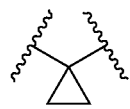.

4. The compound of claim 2, wherein one of Z$^1$, Z$^2$, Z$^3$, and Z$^4$ is —N— and the others are not —N— or —N(O)—; R$^4$ and R$^7$ are each independently H, alkyl, halo or hydroxy, R$^5$ is H, alkyl, —O-alkyl, —O-haloalkyl, cycloalkyl, halo, haloalkyl, hydroxy, hydroxyalkyl, —NH$_2$ or —CN, and R$^6$ is H, alkyl, —O-alkyl, —O-haloalkyl, cycloalkyl, halo, haloalkyl, hydroxy, hydroxyalkyl, —NH$_2$ or —CN.

5. The compound of claim 2, wherein R$^{10}$ is:

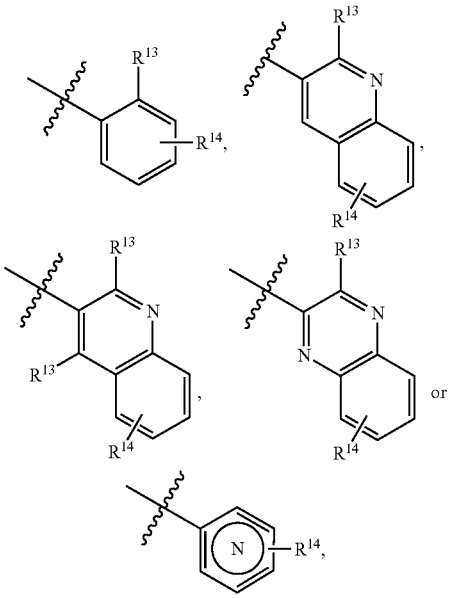

wherein R$^{13}$ is H, F, Br or Cl; R$^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and

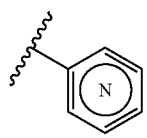

represents a pyridyl group, wherein the ring nitrogen atom can be at any of the five unsubstituted ring atom positions.

6. The compound of claim 5, wherein $R^4$ and $R^7$ are each independently H, halo or hydroxy; $R^5$ is H, alkyl, —O-alkyl, —O-haloalkyl, cycloalkyl, halo, haloalkyl, hydroxy, hydroxyalkyl, —$NH_2$ or —CN; and $R^6$ is H, alkyl, —O-alkyl, —O-haloalkyl, cycloalkyl, halo, haloalkyl, hydroxy, hydroxyalkyl, —$NH_2$ or —CN.

7. A compound of claim 1 having the formula:

(Ia)

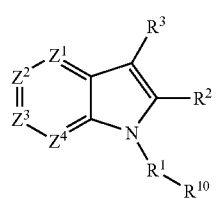

or a pharmaceutically acceptable salt or ester thereof, wherein:

$Z^1$ is —N—, —N(O)— or —C($R^4$)—;

$Z^2$ is —N—, —N(O)— or —C($R^5$)—;

$Z^3$ is —N—, —N(O)— or —C($R^6$)—;

$Z^4$ is —N—, —N(O)— or —C($R^7$)—, such that one of $Z^1$, $Z^2$, $Z^3$ and $Z^4$ is —N— or —N(O)— and the others are not —N— or —N(O)—;

$R^1$ is —$CH_2$—, —$CH_2CH_2$—, —CH($CH_3$)— or

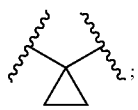 [SMILES: *C1(*)CC1]

$R^2$ is —C(O)N($R^9$)SO$R^{11}$, —C(O)N($R^9$)$SO_2R^{11}$, or —C(O)N($R^9$)$SO_2$N($R^{11}$)$_2$;

$R^3$ is:

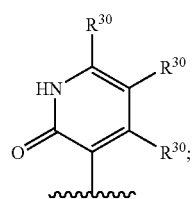

$R^4$, $R^5$, $R^6$ and $R^7$ are each, independently, H, alkyl, -cycloalkyl, -heterocycloalkyl, haloalkyl, halo, hydroxy, -Oalkyl, -Ohaloalkyl-$NH_2$, —NH-alkyl or —N(alkyl)$_2$;

$R^{10}$ is:

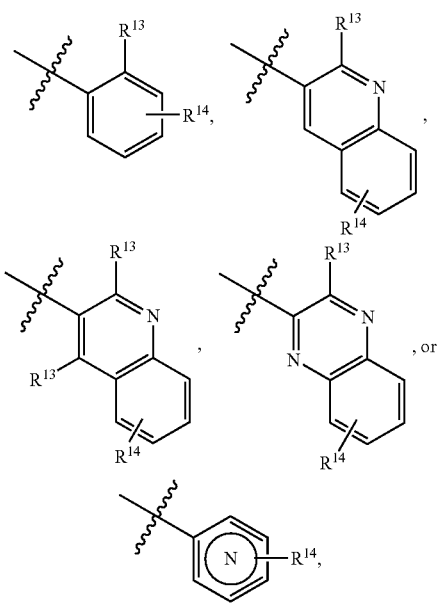

each occurrence of $R^{11}$ is independently alkyl, aryl, cycloalkyl, haloalkyl, heteroaryl, heterocycloalkyl or hydroxyalkyl;

each occurrence of $R^{12}$ is independently H, halo, —N(alkyl)$_2$, —OH, —O-alkyl, alkyl, cycloalkyl or heterocycloalkyl, or two $R^{12}$ groups, together with the carbon atoms to which they are attached, join to form a cycloalkyl, heterocycloalkyl or C=O group;

$R^{13}$ is H, F, Br or Cl;

$R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl;

each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form a –3- to 7-membered ring selected from aryl, cycloalkyl, heteroaryl and heterocycloalkyl; and

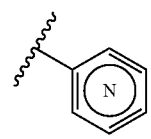

represents a pyridyl group, wherein the ring nitrogen atom can be at any of the five unsubstituted ring atom positions.

8. A compound having the formula:

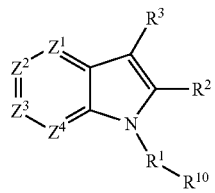

(II)

or a pharmaceutically acceptable salt or ester thereof, wherein:

$Z^1$ is —N—, —N(O)— or —C($R^4$)—;
$Z^2$ is —N—, —N(O)— or —C($R^5$)—;
$Z^3$ is —N—, —N(O)— or —C($R^6$)—;
$Z^4$ is —N—, —N(O)— or —C($R^7$)—, wherein one of $Z^1$, $Z^2$, $Z^3$, and $Z^4$ is —N— and the others are not —N— or —N(O)—;
$R^1$ is —[C($R^{12}$)$_2$]$_r$;
$R^2$ is —C(O)$R^9$, —C(O)O$R^9$, —C(O)OCH$_2$O$R^9$, —C(O)N($R^9$)$_2$, —[C($R^{12}$)$_2$]$_q$—C(O)O$R^9$, —[C($R^{12}$)$_2$]$_q$—C(O)N($R^9$)$_2$, -alkyl, —[C($R^{12}$)$_2$]$_q$aryl, —[C($R^{12}$)$_2$]$_q$cycloalkyl, —[C($R^{12}$)$_2$]$_q$cycloalkenyl, —[C($R^{12}$)$_2$]$_q$heterocycloalkyl, —[C($R^{12}$)$_2$]$_q$-heteroaryl or —[C($R^{12}$)$_2$]$_q$-heterocycloalkenyl, wherein an aryl, cycloalkyl, cycloalkenyl, heterocycloalkyl, heterocycloalkenyl or heteroaryl group can be optionally substituted with up to 4 substituents, which are the same or different, and are selected from alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$—haloalkyl, —[C($R^{12}$)$_2$]$_q$hydroxyalkyl, halo, hydroxy, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ and —SO$_2$N($R^9$)C(O)N($R^9$)$_2$;

$R^3$ is:

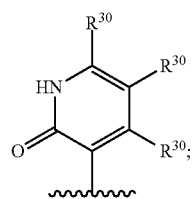

$R^4$, $R^5$, $R^6$ and $R^7$ are each, independently, H, alkyl, alkenyl, alkynyl, aryl, —[C($R^{12}$)$_2$]$_q$cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$hydroxyalkyl, halo, hydroxy, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ or —SO$_2$N($R^9$)C(O)N($R^9$)$_2$;

each occurrence of $R^8$ is independently H, alkyl, alkenyl, alkynyl, —[C($R^{12}$)$_2$]$_q$-aryl, —[C($R^{12}$)$_2$]$_q$cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

each occurrence of $R^9$ is independently H, alkyl, alkenyl, alkynyl, —[C($R^{12}$)$_2$]$_q$-aryl, —[C($R^{12}$)$_2$]$_q$cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

$R^{10}$ is aryl or heteroaryl, wherein an aryl or heteroaryl group can be optionally and independently substituted with up to 4 substituents, which are each independently selected from alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ and —SO$_2$N($R^9$)C(O)N($R^9$)$_2$;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$hydroxyalkyl, halo, hydroxy, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$alkyl, —[C($R^{12}$)$_2$]$_q$—NHSO$_2$cycloalkyl, —[C($R^{12}$)$_2$]$_q$—NHSO$_2$aryl, —[C($R^{12}$)$_2$]$_q$—SO$_2$N($R^9$)$_2$ and —SO$_2$N($R^9$)C(O)N($R^9$)$_2$;

each occurrence of $R^{12}$ is independently H, halo, —N($R^9$)$_2$, —O$R^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two $R^{12}$ groups, together with the carbon atoms to which they are attached, join to form a cycloalkyl, heterocycloalkyl or C=O group;

each occurrence of $R^{30}$ is independently H, alkyl, alkenyl, alkynyl, aryl, —[C($R^{12}$)$_2$]$_q$cycloalkyl, —[C($R^{12}$)$_2$]$_q$cycloalkenyl, —[C($R^{12}$)$_2$]$_q$heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$hydroxyalkyl, halo, hydroxy, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ or —SO$_2$N($R^9$)C(O)N($R^9$)$_2$, or two adjacent R[30] groups, together with the carbon atoms to which they are attached, join to form a –3- to 7-membered ring selected from aryl, cycloalkyl, heteroaryl and heterocycloalkyl;

each occurrence of p is independently 0, 1 or 2;

each occurrence of q is independently an integer ranging from 0 to 4; and each occurrence of r is independently an integer ranging from 1 to 4.

9. The compound of claim 8, wherein R[2] is —C(O)OR[9] or —C(O)N(R[9])$_2$, wherein R[9] is H, alkyl, aryl, cycloalkyl, heteroaryl or heterocycloalkyl.

10. The compound of claim 9, wherein each occurrence of R[30] is independently, H, halo, —N(alkyl)$_2$, —OH, —O-alkyl, —O-haloalkyl, alkyl, cycloalkyl or heterocycloalkyl, or two adjacent R[30] groups, together with the carbon atoms to which they are attached, join to form an aryl, cycloalkyl, heteroaryl or heterocycloalkyl group.

11. The compound of claim 9 wherein R[1] is —CH$_2$—, —CH$_2$CH$_2$—, —CH(CH$_3$)— or

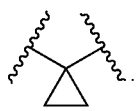

12. The compound of claim 9, wherein one of Z[1], Z[2], Z[3], and Z[4] is —N— and the others are not —N— or —N(O)—; and R[4] and R[7] are each independently H, alkyl, halo or hydroxy, R[5] is H, alkyl, —O-alkyl, —O-haloalkyl, cycloalkyl, halo, haloalkyl, hydroxy, hydroxyalkyl, —NH$_2$ or —CN, and R[6] is H, alkyl, —O-alkyl, —O-haloalkyl, cycloalkyl, halo, haloalkyl, hydroxy, hydroxyalkyl, —NH$_2$ or —CN.

13. The compound of claim 8, wherein R[10] is:

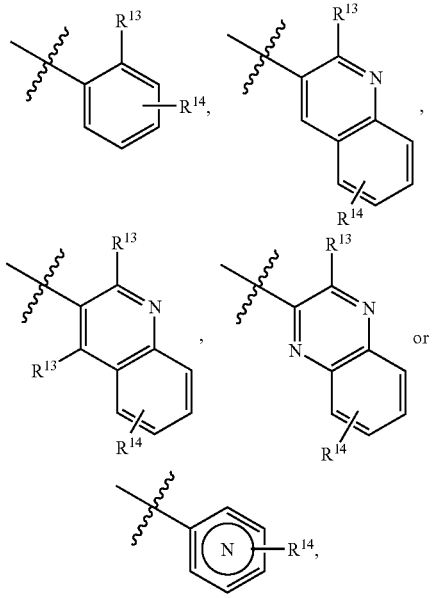

wherein R[13] is H, F, Br or Cl, R[14] represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl, and

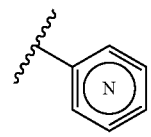

represents a pyridyl group, wherein the ring nitrogen atom can be at any of the five unsubstituted ring atom positions.

14. A compound having the structure:

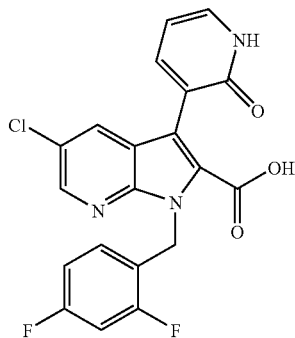

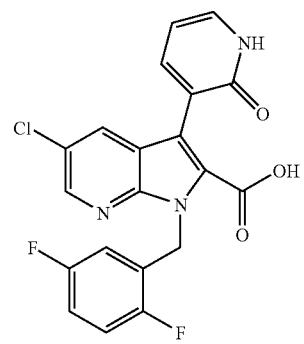

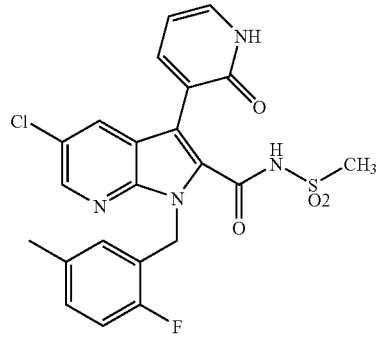

143
-continued
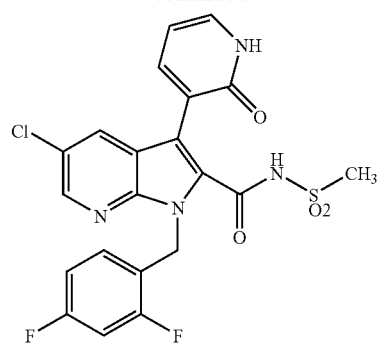
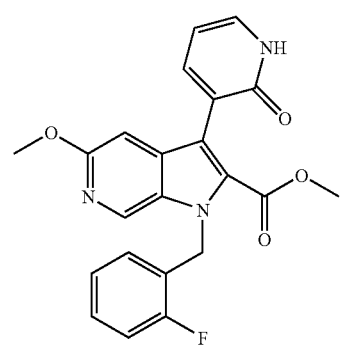
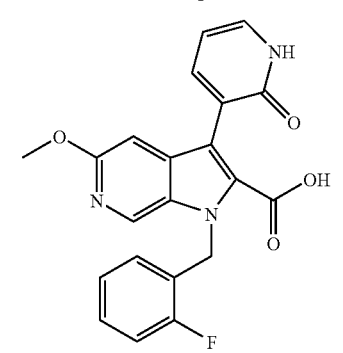
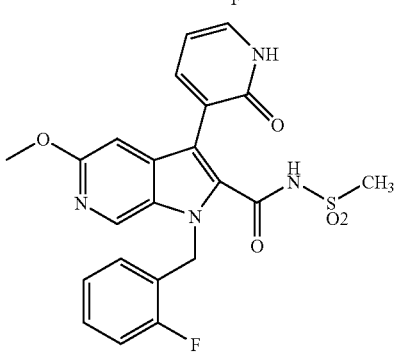
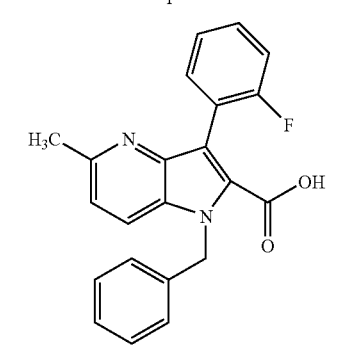
144
-continued
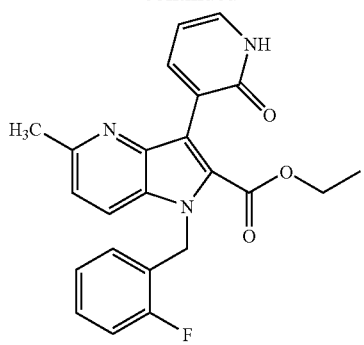
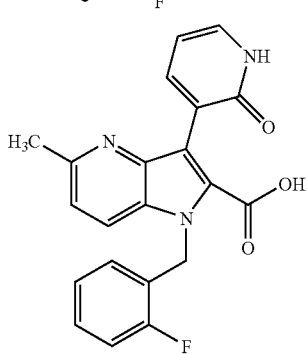
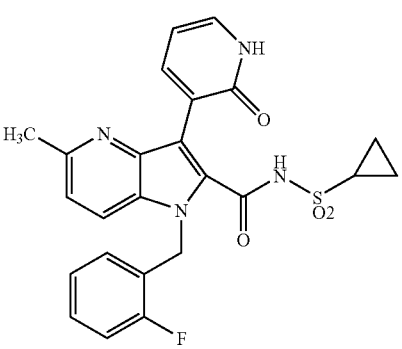
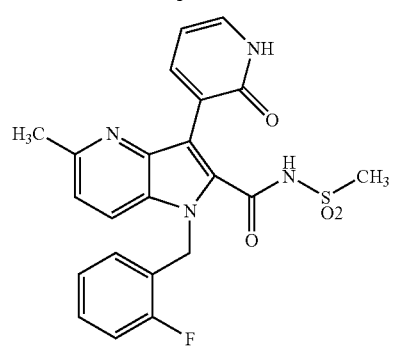
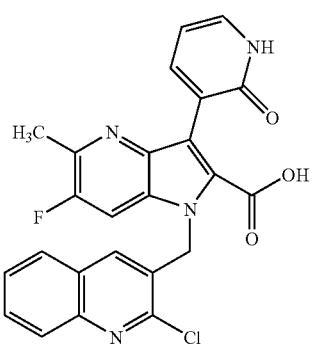

145
-continued
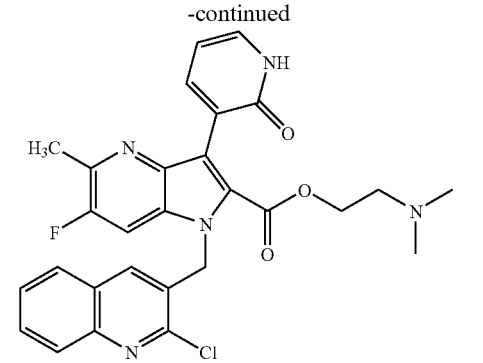
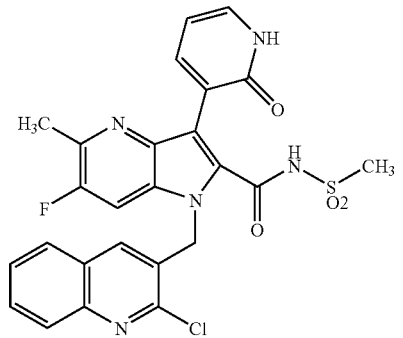
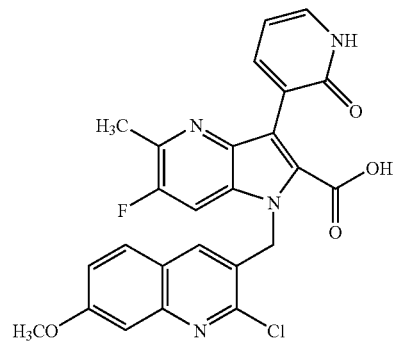
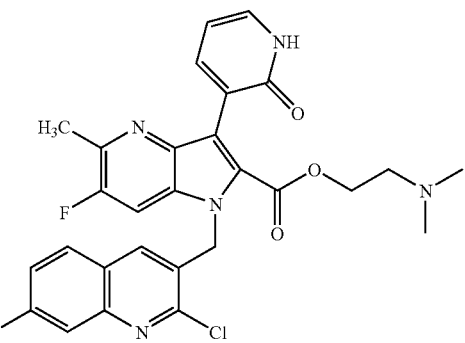
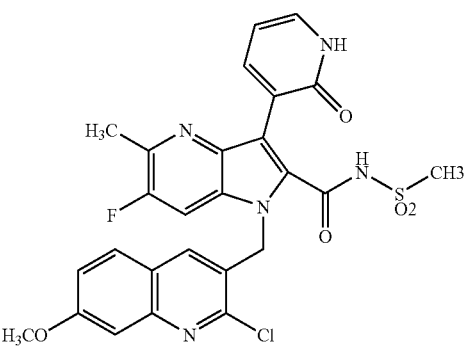
146
-continued
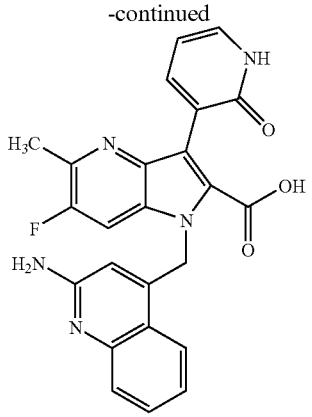
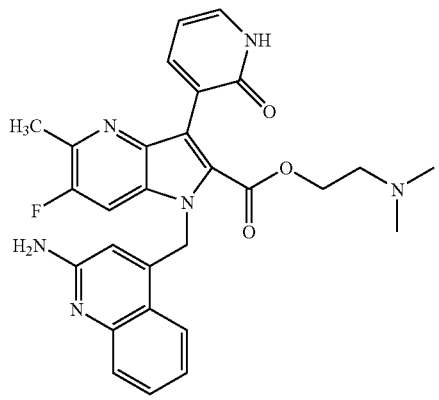
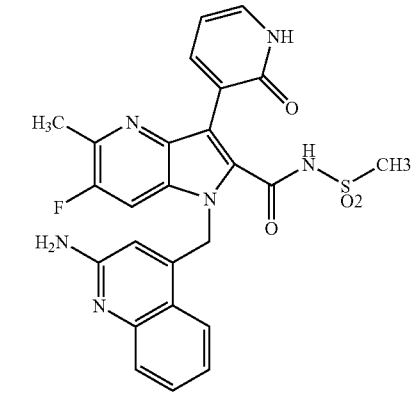
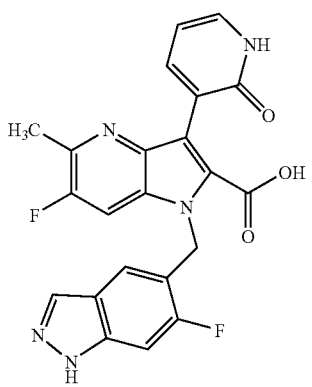

147
-continued
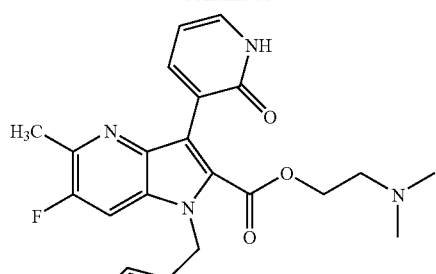
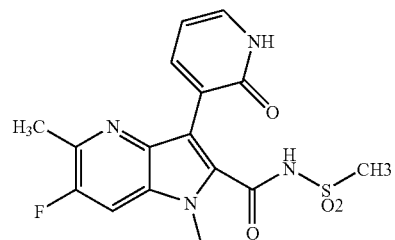
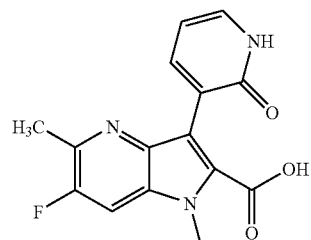
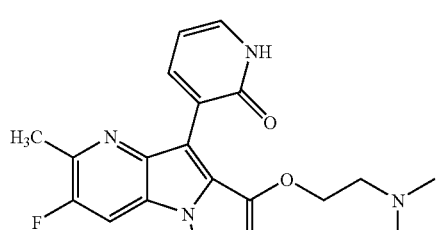
148
-continued
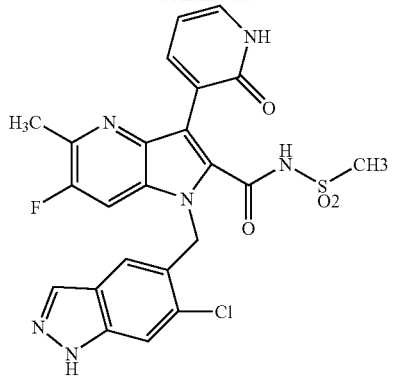
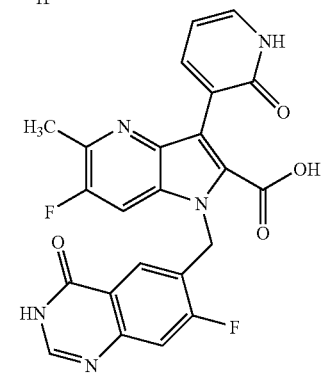
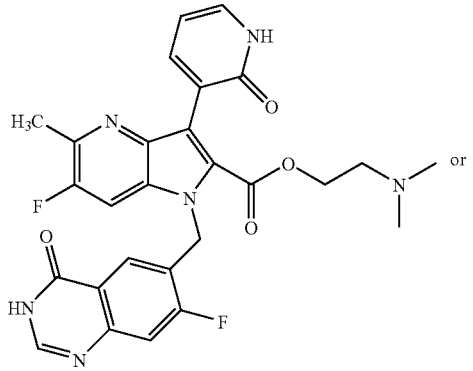 or
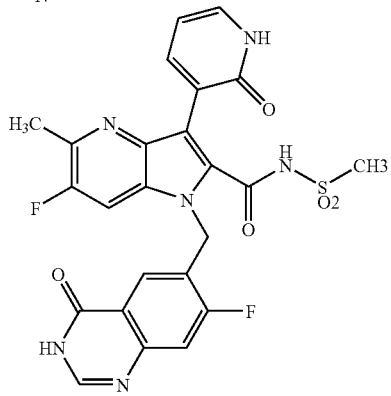
or a pharmaceutically acceptable salt or ester thereof.
15. A composition comprising at least one compound of claim 1 or a pharmaceutically acceptable salt or ester thereof, and at least one pharmaceutically acceptable carrier.
* * * * *

UNITED STATES PATENT AND TRADEMARK OFFICE
CERTIFICATE OF CORRECTION

PATENT NO. : 8,404,845 B2  Page 1 of 1
APPLICATION NO. : 12/675270
DATED : March 26, 2013
INVENTOR(S) : Anilkumar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 329 days.

Signed and Sealed this
First Day of September, 2015

Michelle K. Lee
*Director of the United States Patent and Trademark Office*